US011812936B2

(12) United States Patent
Shinar et al.

(10) Patent No.: US 11,812,936 B2
(45) Date of Patent: Nov. 14, 2023

(54) APPARATUS AND METHODS FOR MONITORING A SLEEPING SUBJECT

(71) Applicant: Hill-Rom Services, Inc., Batesville, IN (US)

(72) Inventors: Zvika Shinar, Binyamina (IL); Guy Meger, Haifa (IL); Avner Halperin, Ramat Gan (IL)

(73) Assignee: Hill-Rom Services, Inc., Batesville, IN (US)

( * ) Notice: Subject to any disclaimer, the term of this patent is extended or adjusted under 35 U.S.C. 154(b) by 1031 days.

(21) Appl. No.: 16/202,586

(22) Filed: Nov. 28, 2018

(65) Prior Publication Data

US 2019/0090860 A1 Mar. 28, 2019

Related U.S. Application Data

(63) Continuation of application No. 14/843,021, filed on Sep. 2, 2015, now Pat. No. 10,172,593, which is a continuation-in-part of application No. 14/726,706, filed on Jun. 1, 2015, now Pat. No. 10,575,829.

(60) Provisional application No. 62/152,902, filed on Apr. 26, 2015, provisional application No. 62/102,031, filed on Jan. 11, 2015, provisional application No. 62/088,697, filed on Dec. 8, 2014, provisional application No. 62/057,250, filed on Sep. 30, 2014, provisional application No. 62/045,237, filed on Sep. 3, 2014.

(51) Int. Cl.
| | |
|---|---|
| *G06F 15/00* | (2006.01) |
| *A61B 10/00* | (2006.01) |
| *A61B 5/00* | (2006.01) |
| *A61B 5/024* | (2006.01) |
| *A61B 5/08* | (2006.01) |
| *G16H 40/20* | (2018.01) |
| *A61B 5/02* | (2006.01) |
| *A61B 5/01* | (2006.01) |
| *A61B 5/11* | (2006.01) |

(52) U.S. Cl.
CPC ...... *A61B 10/0012* (2013.01); *A61B 5/02405* (2013.01); *A61B 5/0816* (2013.01); *A61B 5/4343* (2013.01); *A61B 5/4809* (2013.01); *A61B 5/6892* (2013.01); *A61B 5/7282* (2013.01); *G16H 40/20* (2018.01); *A61B 5/01* (2013.01); *A61B 5/02* (2013.01); *A61B 5/024* (2013.01); *A61B 5/08* (2013.01); *A61B 5/11* (2013.01); *A61B 5/4812* (2013.01); *A61B 5/6891* (2013.01); *A61B 5/7267* (2013.01)

(58) Field of Classification Search
None
See application file for complete search history.

(56) References Cited

U.S. PATENT DOCUMENTS

| | | |
|---|---|---|
| 5,699,038 A | 12/1997 | Ulrich |
| 5,902,250 A | 5/1999 | Verrier |
| 5,976,082 A | 11/1999 | Wong |
| 6,080,106 A | 6/2000 | Lloyd |
| 6,821,258 B2 | 11/2004 | Reed |
| 6,827,670 B1 | 12/2004 | Stark |
| 6,955,647 B2 | 10/2005 | Rice |
| 7,077,810 B2 | 7/2006 | Lange |
| 7,314,451 B2 | 1/2008 | Halperin |
| 7,351,206 B2 | 4/2008 | Suzuki |
| 7,572,225 B2 | 8/2009 | Stahmann |
| 7,610,094 B2 | 10/2009 | Stahmann |
| 7,704,215 B2 | 4/2010 | Lewicke |
| 7,778,851 B2 | 8/2010 | Schoenberg |
| 7,860,583 B2 | 12/2010 | Condurso |
| 8,002,553 B2 | 8/2011 | Hatlestad |
| 8,376,954 B2 | 2/2013 | Lange |
| 8,403,865 B2 | 3/2013 | Halperin |
| 8,491,492 B2 | 7/2013 | Shinar |
| 8,517,953 B2 | 8/2013 | Lange |
| 8,585,607 B2 | 11/2013 | Klap |
| 8,603,010 B2 | 12/2013 | Lange |
| 8,679,030 B2 | 3/2014 | Shinar |
| 8,679,034 B2 | 3/2014 | Halperin |
| 8,731,646 B2 | 5/2014 | Halperin |
| 8,734,360 B2 | 5/2014 | Klap |

(Continued)

FOREIGN PATENT DOCUMENTS

| | | |
|---|---|---|
| EP | 3001864 B1 | 5/2020 |
| JP | 2002224053 A | 8/2002 |

(Continued)

OTHER PUBLICATIONS

Kortelainen, Juha M., Mark Van Gils, and Juha Pärkkä. "Multi-channel bed pressure sensor for sleep monitoring." 2012 Computing in Cardiology. IEEE, 2012.*

Brink, Mark, Christopher H. Müller, and Christoph Schierz. "Contact-free measurement of heart rate, respiration rate, and body movements during sleep." Behavior research methods 38.3 (2006): 511-521.*

Van Der Loos, HF Machiel, Nino Ullrich, and Hisato Kobayashi. "Development of Sensate and Robotic Bed Technologies for Vital Signs Monitoring and Sleep Quality Improvement." Autonomous Robots 15 (2003): 67-79.*

(Continued)

*Primary Examiner* — Anna Skibinsky
(74) *Attorney, Agent, or Firm* — Barnes & Thornburg LLP

(57) ABSTRACT

Apparatus and methods are described including using a sensor to monitor a sleeping subject and generate a signal in response to the monitoring. A control unit is used to accept an input indicative of a person desiring to perform an activity that is potentially disturbing to the sleep of the subject, analyze the sensor signal, in response to the analyzing, identify a time during which the activity is likely to be less disturbing to the sleep of the subject, relative to another time, and generate a notification indicating a suitability of performing the activity at the identified time. Other applications are also described.

20 Claims, 27 Drawing Sheets

(56) References Cited

U.S. PATENT DOCUMENTS

| | | | |
|---|---|---|---|
| 8,821,418 B2 | 9/2014 | Meger | |
| 8,840,564 B2 | 9/2014 | Pinhas | |
| 8,882,684 B2 | 11/2014 | Halperin | |
| 8,942,779 B2 | 1/2015 | Halperin | |
| 8,992,434 B2 | 3/2015 | Halperin | |
| 8,998,830 B2 | 4/2015 | Halperin | |
| 9,026,199 B2 | 5/2015 | Halperin | |
| 2002/0099303 A1 | 7/2002 | Bardy | |
| 2002/0150957 A1 | 10/2002 | Slotman | |
| 2003/0004403 A1 | 1/2003 | Drinan | |
| 2003/0055461 A1 | 3/2003 | Girouard | |
| 2003/0060721 A1 | 3/2003 | Nakazawa | |
| 2003/0125612 A1 | 7/2003 | Fox | |
| 2003/0135127 A1 | 7/2003 | Sackner | |
| 2003/0139678 A1 | 7/2003 | Hoium | |
| 2005/0080349 A1 | 4/2005 | Okada | |
| 2005/0085734 A1 | 4/2005 | Tehrani | |
| 2005/0102165 A1 | 5/2005 | Oshita | |
| 2005/0115561 A1* | 6/2005 | Stahmann | A61B 5/02055 128/204.23 |
| 2005/0163506 A1 | 7/2005 | Ikeda | |
| 2005/0168341 A1 | 8/2005 | Reeder | |
| 2006/0089856 A1 | 4/2006 | Kadhiresan | |
| 2006/0142968 A1 | 6/2006 | Han | |
| 2006/0181424 A1 | 8/2006 | Graves | |
| 2006/0220885 A1 | 10/2006 | Bock | |
| 2007/0083079 A1 | 4/2007 | Lee | |
| 2007/0118054 A1 | 5/2007 | Pinhas | |
| 2007/0299910 A1 | 12/2007 | Fontenot | |
| 2008/0004904 A1 | 1/2008 | Tran | |
| 2008/0033304 A1 | 2/2008 | Dalal | |
| 2008/0114260 A1 | 5/2008 | Lange | |
| 2008/0275349 A1 | 11/2008 | Halperin | |
| 2009/0164239 A1 | 6/2009 | Hayter | |
| 2010/0217618 A1 | 8/2010 | Piccirillo | |
| 2012/0132211 A1 | 5/2012 | Halperin | |
| 2012/0253142 A1 | 10/2012 | Meger | |
| 2013/0006124 A1 | 1/2013 | Eyal | |
| 2013/0245389 A1 | 9/2013 | Schultz | |
| 2013/0245502 A1 | 9/2013 | Lange et al. | |
| 2014/0005502 A1 | 1/2014 | Klap | |
| 2014/0057232 A1 | 2/2014 | Wetmore | |
| 2014/0371635 A1 | 12/2014 | Shinar | |
| 2015/0164433 A1 | 6/2015 | Halperin | |
| 2015/0164438 A1 | 6/2015 | Halperin | |
| 2015/0187038 A1* | 7/2015 | Johnson | G06Q 30/0203 705/2 |
| 2015/0190087 A1 | 7/2015 | Shinar | |
| 2015/0273177 A1 | 10/2015 | Iizuka | |
| 2015/0327792 A1 | 11/2015 | Shinar | |
| 2015/0359481 A1* | 12/2015 | Nyschick | A61B 5/0013 600/301 |
| 2016/0058428 A1 | 3/2016 | Shinar | |
| 2016/0058429 A1 | 3/2016 | Shinar | |
| 2016/0120466 A1 | 5/2016 | Halperin | |
| 2016/0371449 A1 | 12/2016 | Brouse | |
| 2017/0231504 A1 | 8/2017 | Heneghan et al. | |
| 2017/0231545 A1 | 8/2017 | Shinar | |
| 2017/0281017 A1 | 10/2017 | Halperin | |
| 2018/0220897 A1 | 8/2018 | Meger | |
| 2019/0021607 A9 | 1/2019 | Heneghan et al. | |
| 2019/0083044 A1 | 3/2019 | Halperin | |
| 2019/0183353 A1 | 6/2019 | Halperin | |
| 2019/0254570 A1 | 8/2019 | Shinar | |
| 2019/0320987 A1 | 10/2019 | Halperin et al. | |
| 2020/0275876 A1 | 9/2020 | Shinar | |
| 2020/0281523 A1 | 9/2020 | Maidel | |
| 2020/0390403 A1 | 12/2020 | Halperin et al. | |

FOREIGN PATENT DOCUMENTS

| | | |
|---|---|---|
| JP | 2004049838 A | 2/2004 |
| JP | 2004358218 A | 12/2004 |
| JP | 2018047253 A | 3/2018 |
| WO | 0173718 A1 | 10/2001 |
| WO | 2005074361 A2 | 8/2005 |
| WO | 2006137067 A2 | 12/2006 |
| WO | 2007052108 A2 | 5/2007 |
| WO | 2007081629 A2 | 7/2007 |
| WO | 2007143535 A2 | 12/2007 |
| WO | 2008135985 A1 | 11/2008 |
| WO | 2015008285 A1 | 1/2015 |
| WO | 2017138005 A2 | 8/2017 |
| WO | 2019/053719 A1 | 3/2019 |
| WO | 2020183458 A1 | 9/2020 |

OTHER PUBLICATIONS

International Search Report dated Jun. 18, 2020. International Application No. PCT/IL2020/050273. 7 pages.

Written Opinion of the International Searching Authority dated Jun. 18, 2020. International Application No. PCT/IL2020/050273. 5 pages.

Office Action dated Jul. 18, 2019 issued in U.S. Appl. No. 14/726,706. 17 pages.

Boudreau et al., (2013) Circadian variation of heart rate variability across sleep stages. Sleep 36(12): 1919-1928 (10 pages).

Elsenbruch et al., (1999) Heart rate variability during waking and sleep in healthy males and females. Sleep 22(8): 1067-1071 (5 pages).

Shinar et al., (2001) Automatic detection of flow-wave-sleep using heart rate variability. Computers in cardiology 28: 593-596 (4 pages).

\* cited by examiner

APPARATUS AND METHODS FOR MONITORING A SLEEPING SUBJECT

CROSS-REFERENCE TO RELATED APPLICATIONS

The present application is a continuation of U.S. patent application Ser. No. 14/843,021, filed Sep. 2, 2015, entitled "Pregnancy state monitoring," which is a continuation-in-part of U.S. patent application Ser. No. 14/726,706, filed Jun. 1, 2015 (published as US 2016/0058428), entitled "Menstrual state monitoring," which claims the benefit of (i) U.S. Provisional Application 62/045,237, entitled "Monitoring a Sleeping Subject," filed Sep. 3, 2014, (ii) U.S. Provisional Application 62/057,250, entitled "Monitoring a Sleeping Subject," filed Sep. 30, 2014, (iii) U.S. Provisional Application 62/088,697, entitled "Monitoring a Sleeping Subject," filed Dec. 8, 2014, (iv) U.S. Provisional Application 62/102,031, entitled "Monitoring a Sleeping Subject," filed Jan. 11, 2015, and (v) U.S. Provisional Application 62/152,902, filed Apr. 26, 2015, entitled "Monitoring a Sleeping Subject.

The present application is related to International Patent Application PCT IL/2015/050880 to Shinar (published as WO 16/035073), entitled "Monitoring a sleeping subject," filed on Sep. 2, 2015.

Each of the above applications is incorporated herein by reference.

FIELD OF EMBODIMENTS OF THE INVENTION

The present invention relates generally to monitoring a subject in her or his bed, typically in a home setting. Specifically, some applications of the present invention relate to controlling a device or generating an alert or notification in response to the subject's sleep state, and/or for automatically identifying a state of a female subject's menstrual cycle, and/or whether the female subject is in a pregnant or non-pregnant state.

BACKGROUND

There is great variation in the lengths of women's menstrual cycles. It is often the case that women would like to know the current phase of their menstrual cycle. Of particular interest to many is knowledge of when they are in the "fertile window" which occurs from approximately five days before ovulation until two days after ovulation. Typically, urine tests, calendar-based methods, and symptoms-based methods (in which parameters such as cervical mucus, cervical position, and basal body temperature are measured) are used for such determinations.

Quality and duration of sleep plays an important role in overall physical and psychological wellbeing. Unfortunately, many subjects have difficulty falling or staying asleep. In some cases, subjects' sleep may be disrupted by ambient noise from home appliances or other household members.

SUMMARY OF EMBODIMENTS

In accordance with some applications of the present invention, a sensor monitors a female subject and generates a sensor signal in response to the monitoring. A computer processor receives the sensor signal and, in response to analyzing the sensor signal, automatically identifies a menstrual state of the subject, and/or a pregnancy state of the subject (i.e., whether the subject is in a pregnant or a non-pregnant state). For example, the computer processor may identify an aspect of the sensor signal, such as a cardiac-related aspect of the sensor signal, and/or a respiration-related aspect of the sensor signal, and may perform the identification of the subject's state in response thereto. In response to determining the subject's menstrual state, and/or pregnancy state, the computer processor generates an output.

Typically, the sensor performs monitoring of the subject without contacting the subject or clothes the subject is wearing, and/or without viewing the subject or clothes the subject is wearing. For example, the sensor may perform the monitoring without having a direct line of sight of the subject's body, or the clothes that the subject is wearing. Further typically, the sensor performs monitoring of the subject without requiring subject compliance (i.e., without the subject needing to perform an action to facilitate the monitoring that would not have otherwise been performed). It is noted that, prior to the monitoring, certain actions (such as purchasing the sensor and placing the sensor under the subject's bed) may need to be performed by the subject. The term "without requiring subject compliance" should not be interpreted as excluding such actions. Rather the term "without requiring subject compliance" should be interpreted as meaning that, once the sensor has been purchased, placed in a suitable position and activated, the sensor can be used to monitor the subject (e.g., to monitor the subject during repeated monitoring sessions), without the subject needing to perform any actions to facilitate the monitoring that would not have otherwise been performed.

Typically, the sensor is disposed on or within the subject's bed, and configured to monitor the subject automatically, while she is in her bed. For example, the sensor may be disposed underneath the subject's mattress such that the subject is monitored while she is lying upon the mattress, and while carrying out her normal sleeping routine, without the subject needing to perform an action to facilitate the monitoring that would not have otherwise been performed.

For some applications, the sensor is a non-temperature sensor (i.e., the sensor is not configured to measure a temperature of the subject). Typically, the computer processor is configured to identify the subject's menstrual state and/or pregnancy state without determining a temperature of the subject.

In response to determining the subject's menstrual state and/or pregnancy state, the computer processor generates an output. For example, the computer processor may drive an output device (e.g., a monitor, or the screen of a tablet device or a smartphone) to display (or otherwise output) an output that is indicative of the identified menstrual state and/or pregnancy state. Alternatively or additionally, the processor may drive an output device (e.g., a monitor, or the screen of a tablet device or a smartphone) to display (or otherwise output) an output that is indicative of a recommended action to be taken by the user (e.g., "intercourse is recommended within the next 48 hours"), based upon the identified menstrual state and/or pregnancy state. Alternatively or additionally, the processor may drive a device (such as a room-climate-regulation device) in the subject's bedroom to perform a function or to change a parameter of its functioning in response to the identified menstrual state and/or pregnancy state.

Applications of the present invention include apparatus for controlling the playing of music for a subject who is sleeping or is trying to fall asleep. In response to historical data obtained from the subject and to the monitoring of the subject by a sensor, the apparatus controls a property (e.g., a frequency) of the music, e.g., in order to facilitate the slowing of the subject's heart rate and thus help the subject fall asleep.

Applications of the present invention also include apparatus for facilitating the provision of care by a care-provider for a care-receiver. The apparatus monitors sleep of the care-provider and sleep of the care-receiver, and drives an alerting device to wake the care-provider at an opportune time for care-giving, e.g., when both parties are in a light stage of sleep.

Applications of the present invention also include apparatus and methods for facilitating a subject's sleep, such as by controlling noisy home appliances in response to the subject's stage of sleep, and/or by activating a white-noise generator or a noise-cancelation device when a noisy home appliance is activated.

Applications of the present invention also include apparatus for monitoring sleep of a baby in order to facilitate the provision of care to the baby, and/or in order to reduce the baby's disturbances to other members of the household, and/or in order to reduce disturbances to sleep of the baby.

Applications of the present invention also include apparatus for prioritizing care-provision tasks for a plurality of patients in a hospital. The apparatus prioritizes the tasks in response to the respective sleep stages of the patients, such that, for example, a patient who is awake may be provided for before a patient who is asleep.

There is therefore provided, in accordance with some applications of the present invention, apparatus for use with a speaker, the apparatus including:
a sensor configured to monitor a subject and to generate a sensor signal in response thereto; and
a control unit configured to:
analyze the sensor signal,
control a property of a sound signal, in response to (a) the analyzing of the sensor signal, and (b) a historical physiological parameter of the subject that was exhibited in response to a historical sound signal, and
drive the speaker to play the sound signal.

For some applications, the control unit is configured to:
at a first time, set the property of the sound signal to a particular setting, and drive the speaker to play the sound signal, and
at a second time following the first time, in response to (a) the sensor signal indicating that the subject has awakened prematurely, and (b) the subject having fallen asleep at the first time in response to the setting of the property to the particular setting:
set the property of the sound signal to the particular setting, and
drive the speaker to play the sound signal.

For some applications, the apparatus is for use with a mechanism selected from the group consisting of: a vibrating mechanism, and a rocking mechanism, and the control unit is further configured to control the selected mechanism in response to the analyzing of the sensor signal.

For some applications, the control unit is configured to:
at least by analyzing the sensor signal, ascertain that the subject is trying to fall asleep, and
control the property of the sound signal, in response thereto.

For some applications, the control unit is configured to:
by analyzing the sensor signal, ascertain a sleep stage of the subject, and
control the property of the sound signal, in response to the ascertained sleep stage.

For some applications, the historical physiological parameter is selected from the group consisting of: a quality of sleep, a time-to-fall-asleep, a heart-rate-variability, a change in heart rate, a change in respiratory rate, a change in heart-rate-variability, a change in blood pressure, a rate of change in heart rate, a rate of change in respiratory rate, a rate of change in heart-rate-variability, and a rate of change in blood pressure, the control unit being configured to control the property of the sound signal in response to the selected historical physiological parameter.

For some applications, the control unit is configured to select content of the sound signal in response to a manual input.

For some applications, the property is selected from the group consisting of: content, genre, volume, frequency, and phase-shift, the control unit being configured to control the selected property.

For some applications:
the selected property is the frequency, and
the control unit is configured to control the frequency of the sound signal by setting the frequency to be an offset less than a rate selected from the group consisting of: a heart rate of the subject, and a respiratory rate of the subject,
the control unit being configured to control the offset in response to analyzing the sensor signal.

For some applications, the selected property is a phase-shift with respect to a signal selected from the group consisting of: a cardiac signal of the subject, and a respiratory signal of the subject, the control unit being configured to control the phase-shift with respect to the selected signal.

There is additionally provided, in accordance with some applications of the present invention, apparatus for use with an alerting device, the apparatus including:
at least one sensor configured to monitor a care-provider and a care-receiver, and to generate a signal in response thereto; and
a control unit configured to:
analyze the signal,
in response thereto, drive the alerting device to alert the care-provider to provide care for the care-receiver.

For some applications, the at least one sensor is configured to monitor the care-provider and the care-receiver without contacting or viewing the care-provider, without contacting or viewing clothes the care-provider is wearing, without contacting or viewing the care-receiver, and without contacting or viewing clothes the care-receiver is wearing.

For some applications, the control unit is configured to drive the alerting device to alert the care-provider in response to ascertaining, by analyzing the signal, (a) a sleep stage of the care-provider, and (b) a sleep stage of the care-receiver.

For some applications, the control unit is configured to drive the alerting device to alert the care-provider in response to historical sleep-related data of a person selected from the group consisting of: the care-provider, and the care-receiver.

There is further provided, in accordance with some applications of the present invention, apparatus for use with a mechanism selected from the group consisting of: a vibrating mechanism, and a rocking mechanism, the apparatus including:
a sensor configured to monitor a subject and to generate a sensor signal in response thereto; and a control unit configured to:
   analyze the sensor signal, and
   control the selected mechanism in response thereto by sending a control signal to the selected mechanism.

For some applications, in response to analyzing the sensor signal, the control unit is configured to:
   ascertain that the subject is not sleeping, and
   activate the selected mechanism in response thereto.

For some applications, the control unit is configured to control the selected mechanism, further in response to historical sleep-related data of the subject.

For some applications, the control unit is configured to:
   at a first time:
      vary a parameter of the selected mechanism, the parameter being selected from the group consisting of: a vibration frequency, a vibration amplitude, a rocking frequency, and a rocking amplitude, and
      by analyzing the sensor signal, identify a value of the selected parameter that is more conducive to sleep of the subject, relative to other values, and
   at a second time following the first time, set the selected parameter to the identified value.

For some applications, the control unit is configured to:
   at a first time, set a parameter of the selected mechanism to a particular value by sending the control signal to the selected mechanism, and
   at a second time following the first time, in response to (a) the sensor signal indicating that the subject has awakened prematurely, and (b) the subject having fallen asleep at the first time in response to the setting of the parameter to the particular value, set the parameter of the selected mechanism to the particular value.

There is additionally provided, in accordance with some applications of the present invention, a method for use with a home appliance, the method including:
   using a sensor to monitor sleep of a subject and to generate a signal in response thereto; and
   using a control unit:
      analyzing the signal,
      in response thereto, ascertaining a sleep stage of the subject, and
      in response thereto, controlling the home appliance.

For some applications, using the sensor includes using a motion sensor.

For some applications, using the sensor to monitor the sleep of the subject includes using the sensor to monitor the sleep of the subject without contacting or viewing the subject, and without contacting or viewing clothes the subject is wearing.

For some applications, controlling the home appliance includes controlling the home appliance in response to historical sleep-related data of the subject.

For some applications, the home appliance is selected from the group consisting of: a washing machine, a dryer, an air conditioner, a heater, a refrigerator, a freezer, and a dishwasher, the method including controlling the selected home appliance.

For some applications, controlling the home appliance includes inhibiting activation of the home appliance, in response to ascertaining that the sleep stage of the subject is a light-sleep stage.

For some applications, controlling the home appliance includes activating the home appliance, in response to ascertaining that the sleep stage of the subject is a slow-wave sleep stage.

There is further provided, in accordance with some applications of the present invention, apparatus for use with a first noise-making device and a second noise-making device, the apparatus including:
   a sensor configured to monitor sleep of a subject and to generate a sensor signal in response thereto; and
   a control unit configured to:
      analyze the sensor signal,
      receive a device signal from the second noise-making device,
      in response to (a) analyzing the sensor signal, and (b) the device signal, ascertain that the subject is likely to awaken due to an upcoming activation of the second noise-making device, and
      in response thereto, activate the first noise-making device.

There is additionally provided, in accordance with some applications of the present invention, apparatus including:
   a sensor configured to monitor sleep of a baby, and to generate a signal in response thereto;
   an electromechanical arm; and
   a control unit configured to:
      analyze the signal, and
      in response thereto, drive the electromechanical arm to deliver a comfort-inducing object to the baby.

For some applications, the sensor is configured to monitor the sleep of the baby without contacting or viewing the baby, and without contacting or viewing clothes the baby is wearing.

There is further provided, in accordance with some applications of the present invention, apparatus including:
   a sensor configured to monitor a baby, and to generate a signal in response thereto; and
   a control unit configured to:
      analyze the signal,
      in response thereto, ascertain that a mouth of the baby is performing a sucking motion, and
      in response thereto, generate an alert.

For some applications, the sensor is configured to monitor the sleep of the baby without contacting or viewing the baby, and without contacting or viewing clothes the baby is wearing.

There is further provided, in accordance with some applications of the present invention, apparatus including:
   a sensor configured to monitor a baby, and to generate a signal in response thereto;
   an electromechanical arm; and
   a control unit configured to:
      analyze the signal,
      in response thereto, ascertain that a mouth of the baby is performing a sucking motion, and
      in response thereto, drive the electromechanical arm to deliver a comfort-inducing object to the baby.

For some applications, the sensor is configured to monitor the baby without contacting or viewing the baby, and without contacting or viewing clothes the baby is wearing.

There is further provided, in accordance with some applications of the present invention, a method including:
   using a sensor to monitor sleep of a subject, and to generate a signal in response thereto; and
   using a control unit:
      accepting an input indicative of a person desiring to perform an activity that is potentially disturbing to the sleep of the subject, analyzing the signal,
in response to analyzing the signal, identifying a time during which the activity is likely to be less disturbing to the sleep of the subject, relative to another time, and
generating a notification indicating a suitability of performing the activity at the identified time.

For some applications, using the sensor includes using a motion sensor.

There is further provided, in accordance with some applications of the present invention, apparatus for use with a plurality of patients requiring respective care-provision tasks, the apparatus including:
a plurality of sensors configured to monitor sleep of the patients, and to generate a plurality of signals in response thereto; and
a control unit configured to:
analyze the signals,
in response thereto, ascertain respective sleep stages of the patients,
in response to the respective sleep stages, determine a prioritization of at least one of the care-provision tasks over at least one other of the care-provision tasks, and
generate an output indicative of the prioritization.

For some applications, the apparatus further includes a location sensing system that includes a plurality of location sensors, the location sensing system being configured to:
identify respective locations of a plurality of care-providers, and
generate a location-sensing-system signal in response thereto,
the control unit being configured to determine the prioritization further in response to the location-sensing-system signal.

There is further provided, in accordance with some applications of the present invention, apparatus for ascertaining that a subject is likely to be resting on a resting surface, the apparatus including:
a sensor configured to monitor a resting surface and to generate a sensor signal in response thereto; and
a processor configured to:
identify a level of correspondence between the sensor signal and a signal generated by a handheld telecommunications device of the subject, and
in response to the level of correspondence, generate an output that is indicative of whether the subject is likely to be resting on the resting surface.

For some applications, the processor is configured to:
ascertain, for a plurality of time periods, (a) a number N1 of the time periods during which the level of correspondence between the sensor signal and the signal generated by the handheld telecommunications device is greater than a correspondence threshold, and (b) a number N2 of the time periods during which the level of correspondence between the sensor signal and the signal generated by the handheld telecommunications device is not greater than the correspondence threshold, and
generate the output in response to a relationship between N1 and N2.

For some applications, the processor is configured to generate the output in response to a ratio of N1 to N2.

For some applications, the processor is further configured to, by periodically analyzing the signal generated by the telecommunications device, ascertain that the telecommunications device is periodically used by the subject when the subject is not on the resting surface, and the processor is configured to identify the level of correspondence at least partially in response thereto.

For some applications, the telecommunications device includes a device-movement sensor configured to detect movement of the telecommunications device and to generate a device-movement signal in response thereto, and the processor is configured to:
identify the level of correspondence between the sensor signal and the signal generated by the handheld telecommunications device of the subject by identifying a level of correspondence between the sensor signal and the device-movement signal, and
in response to the level of correspondence between the sensor signal and the device-movement signal, generate the output.

For some applications, the processor is configured to:
by analyzing the sensor signal, ascertain that a person is resting on the resting surface,
by analyzing the device-movement signal, ascertain that the telecommunications device is not moving,
in response thereto, ascertain that the subject is likely to be resting on the resting surface, and
in response thereto, generate the output.

For some applications, the processor is configured to:
by analyzing the sensor signal, ascertain that a person is resting on the resting surface,
by analyzing the device-movement signal, ascertain that the telecommunications device is moving,
in response thereto, ascertain that the subject is not likely to be resting on the resting surface, and
in response thereto, generate the output.

For some applications, the signal generated by the handheld telecommunications device includes a usage signal indicative of whether the telecommunications device is being used, and the processor is configured to:
identify the level of correspondence between the sensor signal and the signal generated by the handheld telecommunications device of the subject by identifying a correspondence between the sensor signal and the usage signal, and
in response to the correspondence between the sensor signal and the usage signal, generate the output.

For some applications, the processor is configured to:
by analyzing the sensor signal, ascertain that a person is resting on the resting surface,
by analyzing the usage signal, ascertain that the telecommunications device is not being used,
in response thereto, ascertain that the subject is likely to be resting on the resting surface, and
in response thereto, generate the output.

For some applications, the processor is configured to:
by analyzing the sensor signal, ascertain that a person is on the resting surface,
by analyzing the usage signal, ascertain that the telecommunications device is being used,
in response thereto, ascertain that the subject is not likely to be resting on the resting surface, and
in response thereto, generate the output.

There is further provided, in accordance with some applications of the present invention, apparatus for ascertaining that a subject is likely to be resting on a resting surface, the apparatus including:
a sensor configured to monitor a resting surface and to generate a sensor signal in response thereto; and a processor configured to:
by analyzing the sensor signal, ascertain that a person is resting on the resting surface,
in response to a signal generated by a telecommunications device of the subject, ascertain that the telecommunications device is within a given distance of the resting surface,
in response thereto, ascertain that the subject is likely to be resting on the resting surface, and
in response thereto, generate an output indicating that the subject is likely to be resting on the resting surface.

For some applications:
the processor is further configured to receive an input indicative of coordinates of a location of the resting surface,
the signal generated by the telecommunications device is indicative of coordinates of a location of the telecommunications device, and
the processor is configured to ascertain that the telecommunications device is within the given distance of the resting surface by comparing the location of the telecommunications device with the location of the resting surface.

There is further provided, in accordance with some applications of the present invention, apparatus for controlling a room-climate-regulation device, the apparatus including:
a sensor, configured to monitor a subject and generate a sensor signal in response thereto; and
a control unit, configured to:
analyze the signal,
in response thereto, identify a sleep stage of the subject, and
in response to the identified sleep stage, control the room-climate-regulation device by sending a control signal to the room-climate-regulation device.

For some applications, the sensor includes a motion sensor configured to sense motion of the subject.

For some applications, the sensor is configured to monitor the subject without contacting or viewing the subject, and without contacting or viewing clothes the subject is wearing.

For some applications:
the control unit is further configured to ascertain, in response to analyzing the sensor signal, that a sleep score of the subject is lower than a baseline value,
the apparatus further includes a user interface,
the control unit is configured to drive the user interface to prompt the subject to use the user interface to enter an input that includes at least one factor that may have caused the sleep score to be lower than the baseline value, and
the control unit is configured to control the room-climate-regulation device in response to the input.

For some applications, the control unit is configured to control the room-climate-regulation device by controlling a room-climate-regulation parameter selected from the group consisting of: temperature, humidity, and fan speed.

For some applications, the sensor is configured to monitor the subject by monitoring a parameter of the subject selected from the group consisting of: motion, heart rate, heart rate variability, heartbeat amplitude, respiration rate, respiration amplitude, respiration-cycle variability, tremor, and left ventricular ejection time.

For some applications, the control unit is further configured to:
ascertain, in response to analyzing the sensor signal, a sleep score of the subject, and,
in response to the sleep score, control the room-climate-regulation device.

For some applications, the control unit is further configured to:
ascertain, in response to analyzing the sensor signal, a sleep score of the subject, and,
in response to the sleep score, generate an output that includes a suggested setting for the room-climate-regulation device.

For some applications, the control unit is configured to change a setting of the room-climate-regulation device in response to a premature awakening of the subject.

For some applications, the control unit is configured to:
differentially identify at least two sleep stages selected from the group consisting of: a falling-asleep stage, a beginning-sleep stage, a mid-sleep stage, a premature-awakening stage, an awakening stage, a light sleep stage, a slow-wave sleep stage, and a rapid-eye-movement sleep stage, and
in response to the differentially identified sleep stages, control the room-climate-regulation device by sending the control signal to the room-climate-regulation device.

For some applications, the control unit is configured to, in response to the identified sleep stage, control a noise-emission of the room-climate-regulation device even without adjusting a temperature setting of the room-climate-regulation device.

For some applications, the room-climate-regulation device includes a fan, and the control unit is configured to control the noise-emission of the room-climate-regulation device by controlling a rotating speed of the fan.

For some applications, the control unit is configured to control the noise-emission of the room-climate-regulation device further in response to an ambient noise level.

For some applications, the control unit is configured to reduce a noise level of the room-climate-regulation device in response to the identified sleep stage being a slow-wave sleep stage.

For some applications, the control unit is configured to increase a noise level of the room-climate-regulation device in response to the identified sleep stage being a slow-wave sleep stage.

For some applications, the control unit is configured to reduce a noise level of the room-climate-regulation device in response to the identified sleep stage not being a slow-wave sleep stage.

For some applications, the control unit is configured to increase a noise level of the room-climate-regulation device in response to the identified sleep stage not being a slow-wave sleep stage.

For some applications, the control unit is configured to control a frequency of emitted noise of the room-climate-regulation device in response to (a) the identified sleep stage, and (b) a rate selected from the group consisting of: a heart rate of the subject, and a respiratory rate of the subject.

For some applications, the control unit is configured to, in response to the identified sleep stage, control a temperature setting of the room-climate-regulation device.

For some applications, the control unit is configured to lower the temperature setting of the room-climate-regulation device in response to the identified sleep stage being a rapid-eye-movement sleep stage.

For some applications, the control unit is configured to:
by analyzing the signal, identify an indication of a body temperature of the subject, and in response to the indication, control the temperature setting.

For some applications, the control unit is configured to:
by analyzing the signal, ascertain that the subject is uncomfortable with a current ambient temperature, and
in response to the ascertaining, control the temperature setting.

For some applications, the control unit is configured to ascertain that the subject is uncomfortable with the current ambient temperature by identifying a tremor component of the signal.

For some applications, the apparatus further includes a user interface configured to accept an input from the subject, the input including at least two distinct settings for the room-climate-regulation device corresponding to respective different sleep stages, and
the control unit is configured to control the room-climate-regulation device in response to the input.

For some applications, the control unit is further configured to drive the user interface to prompt the subject to enter the input, in response to a change in a parameter selected from the group consisting of: a season, an ambient temperature, an ambient humidity, and a going-to-sleep time.

For some applications, the sensor is further configured to sense a weight of a blanket of the subject, and the control unit is further configured to drive the user interface to prompt the subject to enter the input, in response to a change in the sensed weight.

For some applications, the control unit is further configured to:
ascertain, in response to analyzing the sensor signal, a sleep score of the subject, and
drive the user interface to prompt the subject to enter the input, in response to the ascertained sleep score being lower than a baseline value.

For some applications, the control unit is configured to ascertain the sleep score by computing a score from at least one parameter selected from the group consisting of: a time to fall asleep, a duration of sleep, a percentage of in-bed time during which the subject is sleeping, and a measure of relaxation of the subject.

For some applications, the control unit is configured to:
for each of a plurality of different settings of the room-climate-regulation device, ascertain, in response to analyzing the sensor signal, a sleep score of the subject; and
in response thereto, generate an output indicative of a setting that is conducive to a higher sleep score, relative to other settings.

For some applications, the apparatus further includes a user interface configured to accept an input from the subject, and the control unit is configured to set the plurality of different settings in response to the input.

For some applications, the control unit is configured to set the plurality of different settings even without any deliberate input from the subject.

For some applications:
the subject is a first subject who shares a room with a second subject,
the apparatus further includes a second sensor, configured to monitor the second subject and generate a second sensor signal in response thereto, and
the control unit is configured to:
analyze the second sensor signal,
in response thereto, identify a sleep stage of the second subject, and
in response to the respective identified sleep stages of the subjects, control the room-climate-regulation device by sending a control signal to the room-climate-regulation device.

For some applications:
the apparatus is for use with a room-climate-regulation device that can simultaneously maintain a first setting in a vicinity of the first subject, and a second setting, which is different from the first setting, in a vicinity of the second subject,
the control unit being configured to control the room-climate-regulation device by communicating the first and second settings to the room-climate-regulation device.

For some applications, the control unit is further configured to:
ascertain, in response to analyzing the sensor signals, respective sleep scores of the subjects, and
in response to the respective sleep scores, control the room-climate-regulation device.

For some applications, the control unit is configured to:
determine a setting of the room-climate-regulation device that facilitates respective sleep scores of the subjects being equal to one another, and
control the room-climate-regulation device by communicating the setting to the room-climate-regulation device.

For some applications, the control unit is configured to:
determine a setting of the room-climate-regulation device, in response to an average sleep score of the subjects, and
control the room-climate-regulation device by communicating the setting to the room-climate-regulation device.

For some applications, the control unit is configured to:
determine a setting of the room-climate-regulation device that maximizes the average sleep score of the subjects, a higher sleep score being indicative of a more restful sleeping session relative to a lower sleep score, and
control the room-climate-regulation device by communicating the setting to the room-climate-regulation device.

For some applications:
the setting is a first setting, and
in response to one of the subjects having fallen asleep, the control unit is configured to communicate a second setting to the room-climate-regulation device, the second setting being different from the first setting.

For some applications, the control unit is configured to:
communicate a first setting to the room-climate-regulation device in response to one of the sensor signals indicating that one of the subjects is trying to fall asleep, the first setting being more conducive to sleep of the one of the subjects, relative to other settings, and
subsequently, in response to the sensor signals indicating that (a) the one of the subjects has fallen asleep, and (b) the other one of the subjects is trying to fall asleep, communicate a second setting to the room-climate-regulation device, the second setting being different from the first setting.

For some applications, the control unit is configured to generate an output to the other one of the subjects, the output indicating that the one of the subjects has fallen asleep.

There is further provided, in accordance with some applications of the present invention, apparatus for controlling a thermoregulation device, the apparatus including:

a motion sensor, configured to monitor a subject and generate a motion signal in response thereto; and
a control unit, configured to:
analyze the motion signal, and
in response thereto, control a temperature setting of the thermoregulation device.

There is additionally provided, in accordance with some applications of the present invention, apparatus for use with a room-climate-regulation device, the apparatus including:
a sensor, configured to monitor a subject and to generate a sensor signal in response thereto; and
a control unit, configured to:
analyze the sensor signal,
in response thereto, identify a rate selected from the group consisting of: a heart rate of the subject, and a respiratory rate of the subject, and
control a property of emitted noise of the room-climate-regulation device in response to the identified rate, the property being selected from the group consisting of: a frequency, and a phase-shift.

There is further provided, in accordance with some applications of the present invention, apparatus for use with a vibrating mechanism, the apparatus including:
a sensor, configured to monitor a subject on a resting surface and generate a sensor signal in response thereto; and
a control unit, configured to:
analyze the sensor signal,
in response thereto, identify a posture of the subject, and
in response to the identified posture, drive the vibrating mechanism to vibrate.

For some applications, the control unit is further configured to, in response to analyzing the sensor signal, identify a sleep stage of the subject, and the control unit is configured to drive the vibrating mechanism to vibrate, further in response to the identified sleep stage.

For some applications, the control unit is configured to drive the vibrating mechanism to vibrate in response to the identified sleep stage being selected from the group consisting of: a sleep stage that is within 5 minutes of an onset of a rapid-eye-movement sleep stage, and a sleep stage that is within 5 minutes of an end of a rapid-eye-movement sleep stage.

For some applications:
the sensor is a first sensor and the sensor signal is a first sensor signal,
the apparatus further includes a second sensor configured to monitor a partner of the subject and generate a second sensor signal in response thereto,
the control unit is further configured to analyze the second sensor signal and, in response thereto, identify a sleep stage of the partner, and
the control unit is configured to drive the vibrating mechanism to vibrate, further in response to the identified sleep stage of the partner.

For some applications:
the control unit is further configured to identify an episode of the subject selected from the group consisting of: a snoring episode, and an apnea episode, and
the control unit is configured to drive the vibrating mechanism to vibrate, further in response to the identified episode.

For some applications, the vibrating mechanism includes a vibrating wristwatch, and the control unit is configured to drive the vibrating mechanism to vibrate by driving the vibrating wristwatch to vibrate.

There is further provided, in accordance with some applications of the present invention, apparatus for use with an adjustable resting surface, the apparatus including:
a sensor, configured to monitor a subject on the resting surface and generate a sensor signal in response thereto; and
a control unit, configured to:
analyze the sensor signal,
in response thereto, identify a posture of the subject, and
in response to the identified posture, adjust a parameter of the resting surface by communicating a signal to the resting surface.

For some applications, the control unit is configured to, in response to the identified posture, adjust an angle of the resting surface.

For some applications, the control unit is further configured to, in response to analyzing the sensor signal, identify a sleep stage of the subject, and the control unit is configured to adjust the parameter of the resting surface, further in response to the identified sleep stage.

For some applications, the control unit is configured to adjust the parameter of the resting surface in response to the identified sleep stage being selected from the group consisting of: a sleep stage that is within 5 minutes of an onset of a rapid-eye-movement sleep stage, and a sleep stage that is within 5 minutes of an end of a rapid-eye-movement sleep stage.

For some applications:
the sensor is a first sensor and the sensor signal is a first sensor signal,
the apparatus further includes a second sensor configured to monitor a partner of the subject and generate a second sensor signal in response thereto,
the control unit is further configured to analyze the second sensor signal and, in response thereto, identify a sleep stage of the partner, and
the control unit is configured to adjust the parameter of the resting surface, further in response to the identified sleep stage of the partner.

For some applications:
the control unit is further configured to identify an episode of the subject selected from the group consisting of: a snoring episode, and an apnea episode, and
the control unit is configured to adjust the parameter of the resting surface, further in response to the identified episode.

For some applications:
the control unit is further configured to identify a coughing episode of the subject, and
the control unit is configured to adjust the parameter of the resting surface, further in response to the identified coughing episode.

For some applications, the adjustable resting surface includes an inflatable pillow, and the control unit is configured to adjust a parameter of the resting surface by adjusting a parameter of the inflatable pillow.

There is further provided, in accordance with some applications of the present invention, a method for monitoring a subject, the method including:
using a motion sensor located in a vehicle, in a seat of the subject, sensing physiological activity of the subject, and generating a motion signal in response thereto; and
using a control unit:
analyzing the motion signal; and
generating an output in response thereto.

For some applications, the vehicle is an airplane, the method including using the motion sensor in the airplane.

For some applications, analyzing the motion signal includes identifying a likelihood of a clinical event of the subject, and generating the output includes generating an alert in response to the identified likelihood.

For some applications, analyzing the motion signal includes identifying a likelihood that the subject is a carrier of a disease, and generating the output includes generating an alert in response to the identified likelihood.

For some applications, analyzing the motion signal includes identifying that the subject is drowsy, and generating the output includes generating an alert in response to identifying that the subject is drowsy.

For some applications, analyzing the motion signal includes identifying that the subject is sleeping, and generating the output includes generating the output in response to identifying that the subject is sleeping.

For some applications, analyzing the motion signal includes identifying an elevated stress level of the subject, and generating the output includes generating an alert in response to the elevated stress level.

For some applications, the vehicle includes a multi-person vehicle,
the method further including:
using at least one other motion sensor located in the vehicle, in a seat of another subject, sensing physiological activity of the other subject, and generating another motion signal in response thereto; and
using the control unit, analyzing the other motion signal, and, in response thereto, identifying an elevated stress level of the other subject,
generating the output including generating an alert in response to each of the subjects having an elevated stress level.

There is additionally provided, in accordance with some applications of the present invention, a method for monitoring a subject, the method including:
using a motion sensor located in a casino, in a seat of the subject, sensing physiological activity of the subject, and generating a motion signal in response thereto; and
using a control unit:
analyzing the motion signal; and
generating an alert in response thereto.

For some applications, analyzing the motion signal includes identifying an elevated stress level of the subject, and generating the alert includes generating an alert in response to the elevated stress level.

For some applications, the method further includes:
using at least one other motion sensor located in the casino, in a seat of another subject, sensing physiological activity of the other subject, and generating another motion signal in response thereto; and
using the control unit, analyzing the other motion signal, and, in response thereto, identifying an elevated stress level of the other subject,
generating the alert including generating an alert in response to each of the subjects having an elevated stress level.

There is further provided, in accordance with some applications of the present invention, apparatus for use with (i) a plurality of subjects sharing a common area, and (ii) a controllable mechanism, the apparatus including:
one or more physiological sensors configured to monitor conditions of the subjects and to generate, in response thereto, a respective sensor signal for each one of the subjects; and
a control unit configured to:
analyze the sensor signals,
in response to analyzing the sensor signals, determine a prioritization of the condition of one of the subjects over the condition of another one of the subjects,
in response to the prioritization, decide whether to control the controllable mechanism, and
in response to (i) the prioritization, and (ii) deciding to control the controllable mechanism, control the controllable mechanism by communicating a control signal to the controllable mechanism.

For some applications, the controllable mechanism is a room-climate-regulation device, the control unit being configured to control the room-climate-regulation device.

For some applications, the controllable mechanism is an adjustable resting surface, the control unit being configured to control the adjustable resting surface.

For some applications, the controllable mechanism is a sound-playing device, the control unit being configured to control the sound-playing device.

For some applications, the controllable mechanism is an illumination device, the control unit being configured to control the illumination device.

For some applications, the control unit is configured to determine the prioritization in response to determining that (a) one of the subjects is sleeping, and (b) another one of the subjects is not sleeping.

For some applications, the control unit is configured to determine the prioritization in response to a health condition of at least one of the subjects.

For some applications, the apparatus further includes at least one body-temperature sensor configured to (i) detect a body temperature of the at least one of the subjects, and (ii) generate a body-temperature signal in response thereto, the control unit being further configured to determine the health condition of the at least one of the subjects in response to the body-temperature signal.

For some applications, the apparatus further includes a user interface configured to accept an input from a user, the control unit being configured to determine the prioritization further in response to the input.

For some applications:
the physiological sensors are configured to monitor comfort of the subjects, and
the control unit is configured to determine the prioritization by determining a prioritization of comfort of one of the subjects over comfort of another one of the subjects.

For some applications:
the physiological sensors are configured to monitor sleep of the subjects, and
the control unit is configured to determine the prioritization by determining a prioritization of sleep of one of the subjects over sleep of another one of the subjects.

For some applications:
controlling the controllable mechanism in a particular manner is (i) facilitative to sleep of a first one of the subjects, and (ii) at least potentially detrimental to sleep of a second one of the subjects, and
the control unit is configured to control the controllable mechanism in the particular manner only if the prioritization indicates that the sleep of the first one of the subjects is to be prioritized over sleep of the second one of the subjects.

For some applications, the controllable mechanism is a vibrating mechanism, the control unit being configured to control the vibrating mechanism.

For some applications:
the control unit is configured to, in response to analyzing the sensor signals, determine that (i) one of the subjects is snoring, and (ii) another one of the subjects may be disturbed by the snoring,
controlling the controllable mechanism includes activating a snoring-inhibition mechanism that is disruptive to sleep of the snoring subject, and
the control unit is configured to activate the snoring-inhibition mechanism, unless the prioritization indicates that sleep of the snoring subject is to be prioritized over sleep of the other one of the subjects.

For some applications, the control unit is configured to:
identify respective sleep stages of the subjects in response to analyzing the sensor signals, and
determine the prioritization in response to identifying the respective sleep stages.

For some applications:
controlling the controllable mechanism in a particular manner is (i) facilitative to sleep of a first one of the subjects, and (ii) at least potentially detrimental to sleep of a second one of the subjects, and
the control unit is configured to control the controllable mechanism in the particular manner only if the second one of the subjects is not sleeping deeply.

For some applications:
each of the respective sleep stages is selected from the group consisting of: a slow-wave sleep stage, a rapid-eye-movement sleep stage, a light sleep stage, and an awake sleep stage,
the control unit is configured to assign:
  a first rank to a sleep stage selected from the group consisting of: a slow-wave sleep stage, and a rapid-eye-movement sleep stage,
  a second rank, which is greater than the first rank, to a sleep stage that is not assigned the first rank and that is selected from the group consisting of: the slow-wave sleep stage, and the rapid-eye-movement sleep stage,
  a third rank, which is greater than the second rank, to a light sleep stage, and
  a fourth rank, which is greater than the third rank, to an awake sleep stage, and
a likelihood of the control unit prioritizing the sleep of a first subject over the sleep of a second subject increases with the rank of the sleep stage of the first subject.

For some applications:
each of the respective sleep stages is selected from the group consisting of: a slow-wave sleep stage, a rapid-eye-movement sleep stage, a light sleep stage, and an awake sleep stage,
the control unit is configured to assign:
  a first rank to a sleep stage selected from the group consisting of: a slow-wave sleep stage, and a rapid-eye-movement sleep stage,
  a second rank, which is greater than the first rank, to a sleep stage that is not assigned the first rank and that is selected from the group consisting of: the slow-wave sleep stage, and the rapid-eye-movement sleep stage,
  a third rank, which is greater than the second rank, to a light sleep stage, and
  a fourth rank, which is greater than the third rank, to an awake sleep stage, and
a likelihood of the control unit prioritizing the sleep of a first subject over the sleep of a second subject decreases with the rank of the sleep stage of the first subject.

For some applications, the control unit is configured to:
in response to analyzing the sensor signals over a plurality of sleeping sessions, identify, for each of the subjects, a sleep-sensitivity of the subject to at least one phenomenon that is generally detrimental to sleep, and
determine the prioritization in response to the identified sleep-sensitivities.

For some applications, the control unit is configured to identify the sleep-sensitivity of each of the subjects by identifying an effect of the phenomenon on a parameter selected from the group consisting of: a duration of sleep of the subject, and a quality of sleep of the subject.

For some applications, the control unit is configured to be more likely to prioritize the sleep of a first one of the subjects over the sleep of a second one of the subjects if the sleep-sensitivity of the first subject is higher than the sleep-sensitivity of the second subject, relative to if the sleep-sensitivity of the first subject were not higher than the sleep-sensitivity of the second subject.

For some applications, the control unit is configured to:
in response to analyzing the sensor signals, calculate, at a particular time, a sleep score for each of the subjects, the sleep score being based on a parameter selected from the group consisting of: a duration of sleep during an interval preceding the particular time, and a quality of sleep during an interval preceding the particular time, and
determine the prioritization in response to the respective sleep scores.

For some applications, at the particular time, the control unit is configured to be more likely to prioritize sleep of a first one of the subjects over sleep of a second one of the subjects if the sleep score of the first one of the subjects is lower than the sleep score of the second one of the subjects, relative to if the sleep score of the first one of the subjects were not lower than the sleep score of the second one of the subjects.

For some applications, controlling the controllable mechanism in a particular manner is (i) facilitative to sleep of a first one of the subjects, and (ii) at least potentially detrimental to sleep of a second one of the subjects, and
the control unit is configured to control the controllable mechanism in the particular manner and at the particular time, in response to the sleep score of the first one of the subjects being lower than a threshold.

For some applications, the control unit is configured to:
identify respective sleep stages of the subjects in response to analyzing the sensor signals, and
control the controllable mechanism in the particular manner and at the particular time in response to the sleep score of the first one of the subjects being lower than the threshold, only if the first one of the subjects is not sleeping deeply.

For some applications, the control unit is configured to control the controllable mechanism in the particular manner and at the particular time in response to the sleep score of the first one of the subjects being lower than the threshold, only if (i) the first one of the subjects is not sleeping deeply, and (ii) the second one of the subjects is not sleeping deeply.

There is additionally provided, in accordance with some applications of the present invention, apparatus for use with an alarm clock for waking a subject, the apparatus including:
a sensor configured to monitor a resting surface, and to generate a signal in response thereto; and a control unit configured to:
  analyze the signal,
  in response thereto, determine that, even if the resting surface is occupied by someone, the resting surface is likely not being occupied by the subject, and
  in response thereto, inhibit the alarm clock from generating an alarm.

For some applications, the control unit is further configured to stop inhibiting the alarm clock from generating an alarm, in response to determining that the resting surface is likely being occupied by the subject.

There is further provided, in accordance with some applications of the present invention, apparatus for use with an alarm clock for waking a subject, the apparatus including:
  a sensor configured to monitor a resting surface, and to generate a signal in response thereto; and
  a control unit, separate from the alarm clock, and configured, following a first alarm generated by the alarm clock, to:
    analyze the signal,
    in response to analyzing the signal, determine that the resting surface is likely being occupied by the subject, and
    in response thereto, drive the alarm clock to generate a second alarm.

There is additionally provided, in accordance with some applications of the present invention, apparatus for use with (i) a first subject and a second subject sharing a common sleep area, and (ii) an alarm clock, the apparatus including:
  a sensor configured to monitor the second subject and to generate a sensor signal in response thereto; and
  a control unit configured to:
    accept an input indicative of (i) an earliest desired awakening time, and (ii) a latest desired awakening time, for the first subject, and
    at a time between the earliest desired awakening time and the latest desired awakening time:
      analyze the sensor signal,
      in response thereto, determine a sleep stage of the second subject,
      in response to the sleep stage of the second subject, determine whether to drive the alarm clock to generate an alarm at the time, and
      in response to determining to drive the alarm clock to generate an alarm, drive the alarm clock to generate an alarm.

For some applications, the control unit is configured to:
  in response to analyzing the sensor signal over a plurality of sleeping sessions, identify a sleep-sensitivity of the second subject to at least one phenomenon that is generally detrimental to sleep, and
  in response to the identified sleep-sensitivity, determine whether to drive the alarm clock to generate the alarm.

For some applications, the control unit is configured to identify the sleep-sensitivity of the second subject by identifying an effect of the phenomenon on a parameter selected from the group consisting of: a duration of sleep of the second subject, and a quality of sleep of the second subject.

For some applications, the control unit is configured to:
  in response to analyzing the sensor signal, calculate a sleep score for the second subject, the sleep score being based on a parameter selected from the group consisting of: a duration of sleep during an interval preceding the particular time, and a quality of sleep during an interval preceding the particular time, and
  in response to the sleep score, determine whether to drive the alarm clock to generate the alarm.

For some applications, the control unit is configured to determine whether to drive the alarm clock to generate the alarm, in response to a health condition of the second subject.

There is further provided, in accordance with some applications of the present invention, apparatus including:
  a sensor configured to measure a clinical parameter of a patient, and to generate a signal in response thereto;
  a control unit configured to:
    receive the signal from the sensor,
    compare the clinical parameter to a threshold, and
    in response to the comparison, generate an alert to a clinician; and
  a user interface configured to receive an input from the clinician, the input indicating whether the clinician believes the alert to have been justified,
  the control unit being configured to adjust the threshold in response to the input.

There is additionally provided, in accordance with some applications of the present invention, apparatus for use with (i) a common area that is shared by a plurality of subjects, and (ii) a controllable mechanism, the apparatus including:
  at least one sensor configured to monitor the common area and to generate a sensor signal in response thereto; and
  a control unit configured to:
    analyze the sensor signal,
    in response to analyzing the sensor signal, determine which subjects of the plurality of subjects are present in the common area, and
    in response to the determining, control the controllable mechanism by communicating a control signal to the controllable mechanism.

For some applications, the controllable mechanism is a room-climate-regulation device, the control unit being configured to control the room-climate-regulation device.

For some applications, the common area is a common sleeping area, the control unit being configured, in response to analyzing the sensor signal, to determine which subjects of the plurality of subjects are present in the common sleeping area.

For some applications:
  the plurality of subjects consists of a first subject and a second subject,
  the controllable mechanism has at least three settings that are distinct from one another, and
  the control unit is configured to:
    in response to determining that the first subject, but not the second subject, is present in the common area, set the controllable mechanism to a first of the settings by communicating the control signal to the controllable mechanism,
    in response to determining that the second subject, but not the first subject, is present in the common area, set the controllable mechanism to a second of the settings by communicating the control signal to the controllable mechanism, and
    in response to determining that the first and second subjects are present in the common area, set the controllable mechanism to a third of the settings by communicating the control signal to the controllable mechanism.

For some applications, the third of the settings is an intermediate setting between the first and second settings, the control unit being configured to set the controllable mechanism to the intermediate setting in response to determining that the first and second subjects are present in the common area.

For some applications, the control unit is further configured to establish the first of the distinct settings, the second of the distinct settings, and the third of the distinct settings, in response to analyzing the sensor signal.

There is additionally provided, in accordance with some applications of the present invention, apparatus for monitoring a subject, the apparatus including:
 a sensor, configured to monitor the subject during a sleeping session of the subject, and to generate a sensor signal in response to the monitoring; and
 a control unit, configured to:
  analyze the sensor signal,
   in response to analyzing the sensor signal, identify an end of a chronologically-first sleep cycle of the subject during the sleeping session,
   in response to analyzing the sensor signal, identify an aspect of the sensor signal exhibited following the end of the chronologically-first sleep cycle,
   identify a physiological condition of the subject (i) in response to the aspect of the sensor signal that is exhibited following the end of the chronologically-first sleep cycle, and (ii) substantially not in response to any aspect of the sensor signal that is exhibited before the end of the chronologically-first sleep cycle, and
   generate an output indicative of the physiological condition.

For some applications, the control unit is configured to:
 in response to analyzing the sensor signal, identify an end of a chronologically-second sleep cycle of the subject during the sleeping session,
 in response to analyzing the sensor signal, identify an aspect of the sensor signal exhibited following the end of the chronologically-second sleep cycle, and
 identify the physiological condition of the subject (i) in response to the aspect of the sensor signal that is exhibited following the end of the chronologically-second sleep cycle, and (ii) substantially not in response to any aspect of the sensor signal that is exhibited before the end of the chronologically-second sleep cycle.

There is further provided, in accordance with some applications of the present invention, apparatus for monitoring a female subject, the apparatus including:
 a sensor, configured to monitor the subject without contacting the subject or clothes the subject is wearing, and without viewing the subject or clothes the subject is wearing, and to generate a sensor signal in response to the monitoring; and
 a computer processor, configured to:
  receive the sensor signal,
  analyze the sensor signal,
  in response to the analyzing, identify a menstrual state of the subject, and
  generate an output in response thereto.

For some applications, the computer processor is configured to identify the subject's menstrual state without determining a temperature of the subject.

For some applications, the computer processor is configured to identify the subject's menstrual state by identifying a current menstrual state of the subject.

For some applications, the computer processor is configured to identify the subject's menstrual state by predicting an occurrence of a future menstrual state of the subject.

For some applications, the computer processor is configured to identify the menstrual state of the subject, using a machine-learning algorithm.

For some applications, the computer processor is configured to identify the menstrual state of the subject by identifying that the subject is likely to ovulate in less than 10 days.

For some applications, the computer processor is further configured, in response to identifying the menstrual state of the subject, to identify that the subject is likely to experience premenstrual syndrome (PMS) in less than three days, the computer processor being configured to generate the output in response thereto.

For some applications, the computer processor is configured:
 in response to the analyzing, to identify an aspect of the sensor signal selected from the group consisting of: a cardiac-related aspect of the sensor signal, and a respiration-related aspect of the sensor signal, and
 to identify the menstrual state of the subject, in response to the identified aspect.

There is additionally provided, in accordance with some applications of the present invention, apparatus for monitoring a female subject and for use with a bed, the apparatus including:
 a sensor configured to be disposed upon or within the bed, to automatically monitor the subject while the subject is in the bed, and to generate a sensor signal in response to the monitoring; and
 a computer processor, configured to:
  receive the sensor signal,
  analyze the sensor signal,
  in response to the analyzing, identify a menstrual state of the subject, and
  generate an output in response thereto.

For some applications, the bed includes a mattress, and the sensor is configured to be disposed underneath the mattress and to automatically monitor the subject while the subject is lying upon the mattress.

For some applications, the computer processor is configured to identify the subject's menstrual state without determining a temperature of the subject.

For some applications, the computer processor is configured to identify the subject's menstrual state by identifying a current menstrual state of the subject.

For some applications, the computer processor is configured to identify the subject's menstrual state by predicting an occurrence of a future menstrual state of the subject.

For some applications, the computer processor is configured to identify the menstrual state of the subject, using a machine-learning algorithm.

For some applications, the computer processor is configured to identify the menstrual state of the subject by identifying that the subject is likely to ovulate in less than 10 days.

For some applications:
 the computer processor is further configured, in response to identifying the menstrual state of the subject, to identify that the subject is likely to experience premenstrual syndrome (PMS) in less than three days,
 the computer processor being configured to generate the output in response thereto.

For some applications, the computer processor is configured:
 in response to the analyzing, to identify an aspect of the sensor signal selected from the group consisting of: a cardiac-related aspect of the sensor signal, and a respiration-related aspect of the sensor signal, and
 to identify the menstrual state of the subject, in response to the identified aspect.

There is further provided, in accordance with some applications of the present invention, apparatus for monitoring a female subject, the apparatus including:

a sensor, configured to monitor the subject and to generate a sensor signal in response to the monitoring; and a computer processor, configured to:

receive the sensor signal, derive a cardiac-related aspect of the sensor signal by analyzing the sensor signal, based upon the derived cardiac-related aspect of the sensor signal, identify a menstrual state of the subject, and generate an output in response thereto.

For some applications, the computer processor is configured to identify the subject's menstrual state without determining a temperature of the subject.

For some applications, the computer processor is configured to identify the subject's menstrual state by identifying a current menstrual state of the subject.

For some applications, the computer processor is configured to identify the subject's menstrual state by predicting an occurrence of a future menstrual state of the subject.

For some applications, the computer processor is configured to identify the menstrual state of the subject, using a machine-learning algorithm.

For some applications, the computer processor is configured to identify the menstrual state of the subject by identifying that the subject is likely to ovulate in less than 10 days.

For some applications, the computer processor is further configured, in response to identifying the menstrual state of the subject, to identify that the subject is likely to experience premenstrual syndrome (PMS) in less than three days, the computer processor being configured to generate the output in response thereto.

For some applications, the cardiac-related aspect of the sensor signal includes a heart rate variability (HRV) signal, the computer processor being configured to identify the menstrual state of the subject in response to the HRV signal.

There is further provided, in accordance with some applications of the present invention, apparatus for monitoring a female subject, the apparatus including:

a sensor, configured to monitor the subject without requiring compliance of the subject, and to generate a sensor signal in response to the monitoring; and a computer processor, configured to:

receive the sensor signal, analyze the sensor signal, in response to the analyzing, identify whether the subject is in a pregnant state or a non-pregnant state, and generate an output in response thereto.

For some applications, the computer processor is configured to identify whether the subject is in the pregnant state or the non-pregnant state without determining a temperature of the subject.

For some applications, the sensor is configured to be disposed upon or within a bed of the subject, and is configured to monitor the subject automatically while the subject is in her bed.

For some applications, the computer processor is configured to identify whether the subject is in the pregnant state or the non-pregnant state, using a machine-learning algorithm.

For some applications, the computer processor is configured:

in response to the analyzing, to identify an aspect of the sensor signal selected from the group consisting of: a cardiac-related aspect of the sensor signal, and a respiration-related aspect of the sensor signal, and to identify whether the subject is in the pregnant state or the non-pregnant state, in response to the identified aspect.

The present invention will be more fully understood from the following detailed description of applications thereof, taken together with the drawings, in which:

DETAILED DESCRIPTION OF EMBODIMENTS

Figure 1:
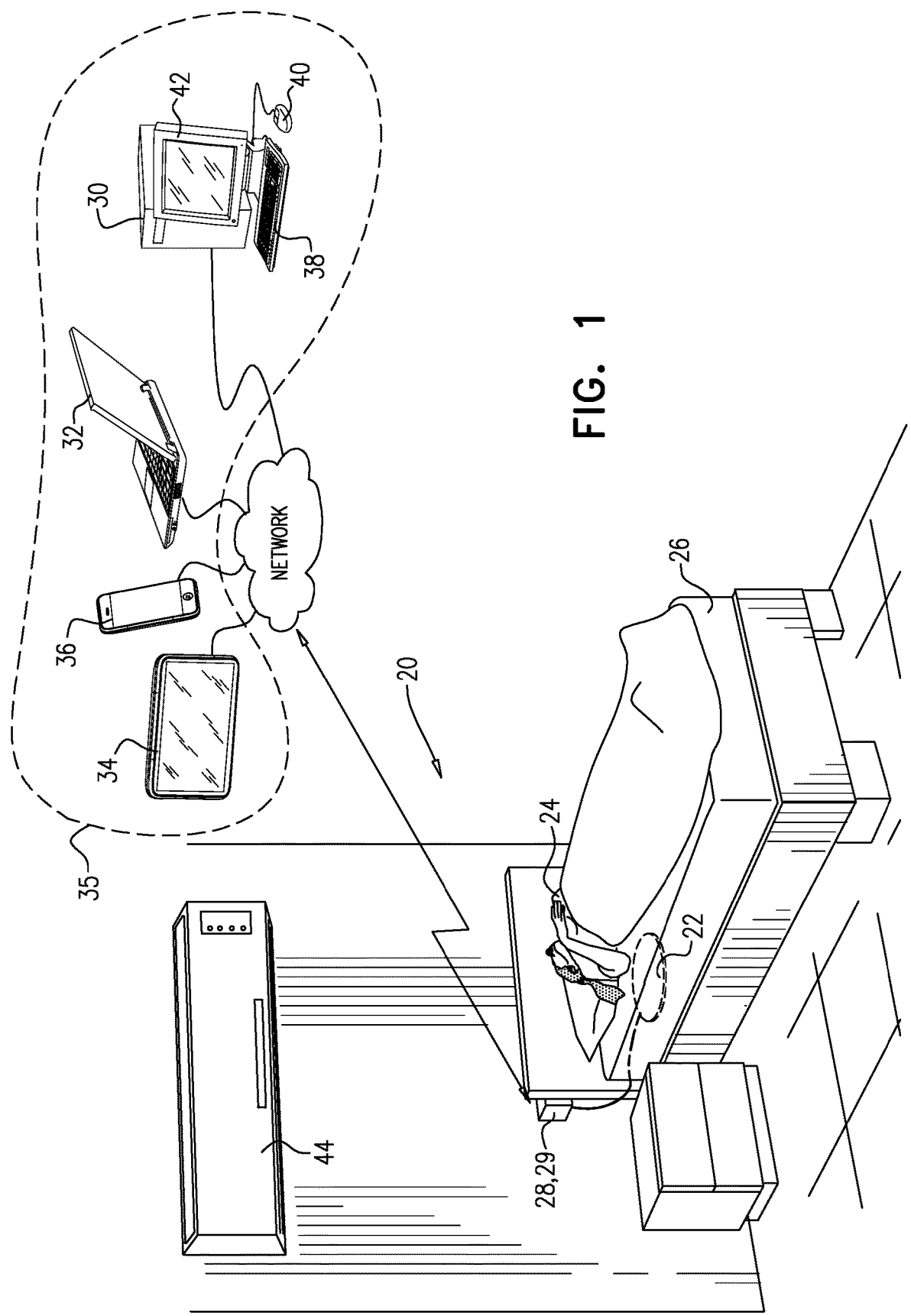
FIG. 1 is a schematic illustration of apparatus for monitoring a subject, in accordance with some applications of the present invention.

Reference is made to FIG. 1, which is a schematic illustration of subject-monitoring apparatus 20, in accordance with some applications of the present invention. Apparatus 20 is generally used to monitor a subject 24, while he or she is in his or her bed in a home setting. For the applications described with reference to FIGS. 2-5, subject 24 is typically female. For some applications (e.g., as described with reference to FIG. 29), the subject-monitoring apparatus is used in a hospital setting.

Subject-monitoring apparatus 20 comprises a sensor 22 (e.g., a motion sensor) that is configured to monitor subject 24. Sensor 22 may be a motion sensor that is similar to sensors described in U.S. Pat. No. 8,882,684 to Halperin, which is incorporated herein by reference. The term "motion sensor" refers to a sensor that senses the subject's motion (e.g., motion due to the subject's cardiac cycle, respiratory cycle, or large-body motion of the subject), while the term "sensor" refers more generally to any type of sensor, e.g., a sensor that includes an electromyographic sensor and/or an imaging sensor.

Typically, sensor 22 includes a sensor that performs monitoring of the subject without contacting the subject or clothes the subject is wearing, and/or without viewing the subject or clothes the subject is wearing. For example, the sensor may perform the monitoring without having a direct line of sight of the subject's body, or the clothes that the subject is wearing. Further typically, the sensor performs monitoring of the subject without requiring subject compliance (i.e., without the subject needing to perform an action to facilitate the monitoring that would not have otherwise been performed). It is noted that, prior to the monitoring, certain actions (such as purchasing the sensor and placing the sensor under the subject's mattress) may need to be performed. The term "without requiring subject compliance" should not be interpreted as excluding such actions. Rather the term "without requiring subject compliance" should be interpreted as meaning that, once the sensor has been purchased, placed in a suitable position and activated, the sensor can be used to monitor the subject (e.g., to monitor the subject during repeated monitoring sessions), without the subject needing to perform any actions to facilitate the monitoring that would not have otherwise been performed.

For some applications, sensor 22 is disposed on or within the subject's bed, and configured to monitor the subject automatically, while she is in her bed. For example, sensor 22 may be disposed underneath the subject's mattress 26, such that the subject is monitored while she is lying upon the mattress, and while carrying out her normal sleeping routine, without the subject needing to perform an action to facilitate the monitoring that would not have otherwise been performed.

A computer processor 28, which acts as a control unit that performs the algorithms described herein, analyzes the signal from sensor 22. Typically, computer processor 28 communicates with a memory 29. For some applications, computer processor 28 is embodied in a desktop computer 30, a laptop computer 32, a tablet device 34, a smartphone 36, and/or a similar device that is programmed to perform the techniques described herein (e.g., by downloading a dedicated application or program to the device), such that the computer processor acts as a special-purpose computer processor. For some applications, as shown in FIG. 1, computer processor 28 is a dedicated computer processor that receives (and optionally analyzes) data from sensor 22, and communicates with computer processors of one or more of the aforementioned devices, which act as external devices.

For some applications, the subject (or another person, such as a care-giver) communicates with (e.g., sends data to and/or receives data from) computer processor 28 via a user interface device 35. As described, for some applications, computer processor is embodied in a desktop computer 30, a laptop computer 32, a tablet device 34, a smartphone 36, and/or a similar device that is programmed to perform the techniques described herein. For such applications, components of the device (e.g., the touchscreen, the mouse, the keyboard, the speakers, the screen) typically act as user interface device 35. Alternatively, as shown in FIG. 1, computer processor 28 is a dedicated computer processor that receives (and optionally analyzes) data from sensor 22. For some such applications, the dedicated computer processor communicates with computer processors of one or more of the aforementioned external devices (e.g., via a network), and the user interfaces of the external devices (e.g., the touchscreen, the mouse, the keyboard, the speakers, the screen) are used by the subject, as user interface device 35, to communicate with the dedicated computer processor and vice versa. For some applications, in order to communicate with computer processor 28, the external devices are programmed to communicate with the dedicated computer processor (e.g., by downloading a dedicated application or program to the external device).

For some applications, user interface includes an input device such as a keyboard 38, a mouse 40, a joystick (not shown), a touchscreen device (such as smartphone 36 or tablet device 34), a touchpad (not shown), a trackball (not shown), a voice-command interface (not shown), and/or other types of user interfaces that are known in the art. For some applications, the user interface includes an output device such as a display (e.g., a monitor 42, a head-up display (not shown) and/or a head-mounted display (not shown), such as Google Glass®), and/or a different type of visual, text, graphics, tactile, audio, and/or video output device, e.g., speakers, headphones, smartphone 36, or tablet device 34. For some applications, the user interface acts as both an input device and an output device. For some applications, the processor generates an output on a computer-readable medium (e.g., a non-transitory computer-readable medium), such as a disk, or a portable USB drive.

Figure 2:
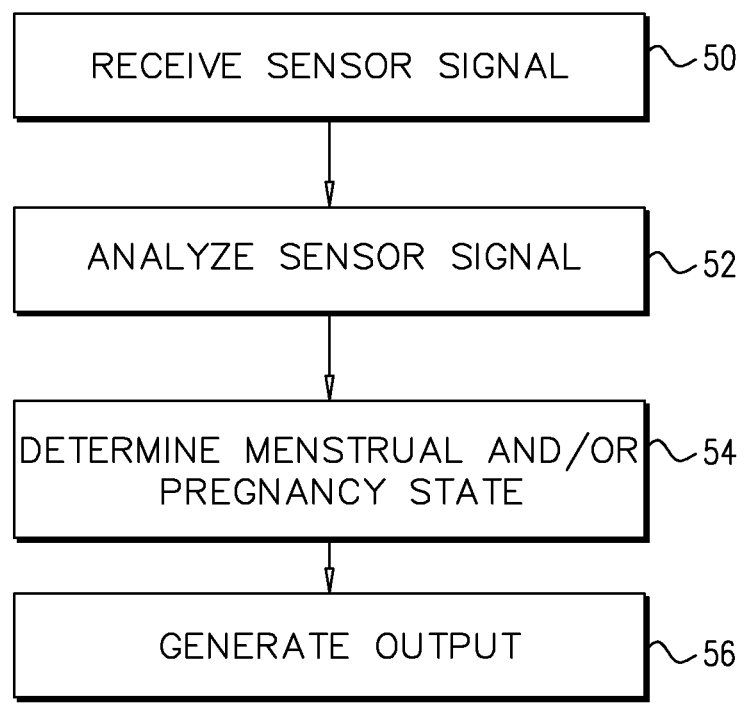
FIG. 2 is a flowchart showing steps of a method for automatically determining a menstrual state and/or a pregnancy state of a female subject, in accordance with some applications of the present invention.

Reference is now made to FIG. 2, which is a flowchart showing steps that are performed by computer processor 28, in accordance with some applications of the present invention. In a first step 50, the computer processor receives the sensor signal from sensor 22. In a second step 52, the computer processor analyzes the signal. For example, the computer processor may identify an aspect of the sensor signal, such as a cardiac-related aspect of the sensor signal, a respiration-related aspect of the sensor signal. In a third step 54, based upon the analysis of the sensor signal, the computer processor identifies a menstrual state and/or a pregnancy state (e.g., a current menstrual state and/or pregnancy state, or a predicted future state) of the subject. For example, the computer processor may (i) identify that the subject is in a pregnant state or a non-pregnant state, and/or (ii) identify a current phase of the subject's menstrual cycle, and/or (iii) identify that the subject is likely to ovulate soon.

In a fourth step 56, the computer processor generates an output in response to the identified menstrual state and/or pregnancy state. For example, the computer processor may drive an output device (e.g., as described above) to display (or otherwise output) an output that is indicative of the identified menstrual state and/or pregnancy state (for example, a smartphone application, running on smartphone 36, may be driven to display such an output). Alternatively or additionally, the processor may drive an output device (e.g., as described above) to display (or otherwise output) an output that is indicative of a recommended action to be taken by the user (e.g., "intercourse is recommended within the next 48 hours"), based upon the identified menstrual state and/or pregnancy state. Alternatively or additionally, the processor may drive a device (such as a room-climate-regulation device 44) in the subject's bedroom to perform a function or to change a parameter of its functioning in response to the identified menstrual state and/or pregnancy state, as described in further detail hereinbelow.

For some applications, sensor 22 is a non-temperature sensor (i.e., the sensor is not configured to measure a temperature of the subject). (For some of the applications described hereinbelow, sensor 22 may include temperature-sensing capabilities.) Typically, the computer processor is configured to identify the subject's menstrual state and/or pregnancy state without determining a temperature of the subject.

Figure 3:
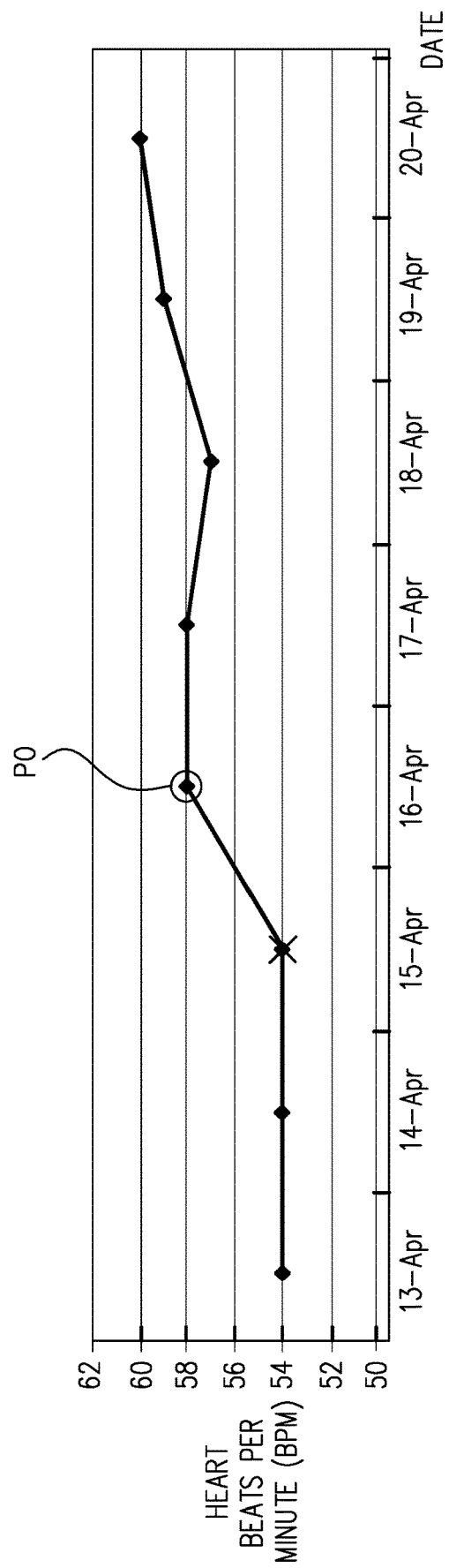
FIG. 3 is an exemplary plot of data with which the apparatus may be used, in accordance with some applications of the present invention.

Reference is now made to FIG. 3, which is an exemplary plot of data with which apparatus 20 may be used, in accordance with some applications of the present invention. In particular, the plot shows experimental data collected from a particular female subject using a non-contact sensor (i.e., a sensor that performs sensing of the subject without contacting the subject or clothes the subject is wearing). The plot shows a set of data points corresponding to the average heart rate, measured in heartbeats-per-minutes (BPM), for the subject, over a sequence of consecutive sleeping sessions. The approximate time of the subject's ovulation, as reported by the subject, is marked in the plot with an enlarged X (at 15 April). As can be seen in the plot, an increase in the average heart rate of the subject was observed post-ovulation. The plot of data thus demonstrates that, in response to observing an increased heart rate, it may be possible to identify that ovulation recently took place. In accordance with the data shown in FIG. 3, in some cases, a subject may experience an increased heart rate, and/or experience other physiological changes (e.g., a change in cardiac pattern) shortly before ovulating; thus, it may also be possible to predict an upcoming ovulation in response to observing an increased heart rate.

Based upon the above-noted observations, in some applications, step 52 of FIG. 2 is performed using the following algorithm. The subject's heart rate is identified. For example, an average heart rate over a period of time (e.g., an average heart rate over a sleeping session) may be identified. The identified heart rate is then compared to a baseline heart rate. For some applications, step 54 of FIG. 2 (determination of the subject's menstrual state and/or pregnancy state) is performed in response to the aforementioned comparison. For example, in response to ascertaining that the identified heart rate is greater than the baseline heart rate, the computer processor may identify that the subject is within a given amount of time (e.g., less than two days) of ovulation. In other words, the computer processor may identify that less than the given amount of time has transpired since the subject ovulated, or identify that it is likely that the subject will ovulate within the given amount of time. In general, this output may help the subject with her fertility planning.

In some applications, the computer processor uses the average heart rate of a previous sleeping session as a baseline, and in response to the identified average heart rate being greater than this baseline, the computer processor identifies the recent ovulation or predicts the upcoming ovulation.

The relatively flat portion of the plot of FIG. 3 that precedes the ovulation of the subject demonstrates that, for a subject who is generally healthy, "normal" variation in average heart rate is relatively small. Thus, even a relatively small increase in average heart rate, e.g., an increase of 1-5 heartbeats-per-minute (BPM), may be indicative of a recent or upcoming ovulation. Hence, in some applications, the computer processor identifies the recent ovulation, or predicts the upcoming ovulation, even in response to the identified heart rate being less than five heartbeats-per-minute greater than the baseline heart rate.

Typically, if the subject becomes pregnant, the heart rate of the subject remains elevated, relative to the pre-ovulation heart rate. (Although, as noted above, typically the heart rate of the subject may increase shortly before ovulation. Therefore, in this context, the "pre-ovulation heart rate" refers to the normal heart rate of the subject, prior to the increase.) If the subject does not become pregnant, on the other hand, the heart rate of the subject drops back to its pre-ovulation level. Hence, in some applications, the computer processor performs step 54 of FIG. 2, by identifying that the subject is pregnant by ascertaining that the identified heart rate is not lower than a post-ovulation baseline heart rate, the post-ovulation baseline heart rate typically being based on a previously-identified elevated heart rate. For example, with reference to FIG. 3, the post-ovulation baseline heart rate might be based on the data point labeled as P0. (For example, the post-ovulation baseline might be two BPM less than the BPM of P0, i.e., approximately 56 BPM.) If, several days after P0 was observed, the average heart rate of the subject drops below this baseline, the computer processor may identify that the subject is not pregnant. Conversely, if, several days after P0 was observed, the average heart rate of the subject has not dropped below this baseline, the computer processor may identify that the subject is pregnant. Alternatively or additionally, the computer processor may identify whether the subject is pregnant by comparing the current heart rate of the subject to the subject's pre-ovulation heart rate.

Typically, the post-ovulation baseline heart rate to which the average heart rate is compared is based on a previously-identified heart rate from the same menstrual cycle as the currently-identified heart rate. For example, the computer processor may identify the post-ovulation baseline heart rate in response to a heart rate of the subject that was identified less than fourteen days prior to identifying the currently-identified heart rate.

As noted above, alternatively or additionally to identifying a cardiac-related aspect of the sensor signal, the computer processor may identify a respiration-related aspect of the sensor signal, such as a respiratory rate of the subject. (For example, the computer processor may identify an average respiratory rate of the subject during a sleeping session of the subject.) In general, respiratory rate, like heart rate, typically rises to an elevated level at around the time of ovulation, and typically remains at the elevated level only if the subject becomes pregnant. Hence, the computer processor may perform step 52 of FIG. 2 as described above with respect to heart rate, but in response to the identified respiratory rate, mutatis mutandis. For example, the computer processor may identify the current phase of the menstrual cycle of the subject (e.g., the computer processor may identify that ovulation recently occurred), and/or identify whether the subject is pregnant, by comparing the identified respiratory rate to a baseline respiratory rate. The use of the respiration-related aspect of the sensor signal for step 52 of FIG. 2 may supplement, or alternatively, take the place of, the use of the cardiac-related aspect of the sensor signal.

In some applications, the identified aspect of the sensor signal includes a heart rate variability (HRV) signal, and the computer processor performs step 54 of FIG. 2 in response to the HRV signal. For example, in response to the HRV signal, the computer processor may identify that the current phase of the subject's menstrual cycle is a late follicular phase. In general, a woman's greatest chances for conceiving begin prior to ovulation, starting with the late follicular phase of her menstrual cycle. (In general, the late follicular phase begins before ovulation, sometime within five days of ovulation.) Thus, it is generally advantageous for a woman who desires to become pregnant to know that she is in her late follicular phase. In some applications, the late follicular phase is identified in response to an aspect of a component of the power spectrum of the HRV signal, e.g., in response to the component of the power spectrum of the HRV signal having an amplitude that exceeds a threshold. In some applications, the component of the power spectrum of the HRV signal that is used for identifying the late follicular phase lies between 0.1 and 0.5 Hz. Alternatively or additionally, a component that lies between 0.04 and 0.15 Hz, and/or a component that lies between 0.008 and 0.04 Hz, may be used to identify the late follicular phase. In some applications, the computer processor identifies the late follicular phase in response to a ratio of power-spectrum amplitudes; for example, the computer processor may identify the late follicular phase in response to a ratio of (i) the amplitude of a 0.04-0.15 Hz component of the spectrum, to (ii) the amplitude of a 0.008-0.04 Hz component.

In some cases, alternatively or additionally to knowing that she is in her late follicular phase, a subject may wish to know her anticipated date of ovulation. Thus, in some applications, the computer processor performs step 54 of FIG. 2, by predicting that it is likely that the subject will ovulate within a given period of time, e.g., in less than 10 days, e.g., in 0.5-5 days. As described hereinabove, the computer processor may predict the upcoming ovulation in response to an elevated heart rate of the subject. Alternatively or additionally to basing the prediction on an elevated heart rate, the computer processor may predict the upcoming ovulation in response to the HRV signal (e.g., in response to the power spectrum of the HRV signal).

For some applications, in response to determining the current stage of the subject's menstrual cycle (e.g., using techniques described herein), the computer processor generates an output indicative of when it is advisable for the subject to have intercourse such as to increase her chances of conceiving a baby. Furthermore, there is evidence that having intercourse close to ovulation or shortly thereafter (e.g., on the day of ovulation or subsequent thereto) favors conceiving a male baby, while having intercourse several days (e.g., 2-5 days) prior to ovulation favors conceiving a female baby. Therefore, for some applications, the subject (or a person related to the subject, such as the subject's partner) communicates an input to computer processor 28 (e.g., via user interface device 35) that is indicative of a desire to have a child of a given gender. In response to determining the current stage of the subject's menstrual cycle (e.g., using techniques described herein), the computer processor generates an output indicative of when it is advisable for the subject to have intercourse such as to increase her chances of conceiving a baby of the desired gender.

In some applications, the computer processor identifies that the subject is likely to experience premenstrual syndrome (PMS) within a given period of time, e.g., in more than 0.5 days and/or less than three days. For example, the computer processor may predict the upcoming episode of PMS in response to the HRV signal (e.g., in response to the power spectrum of the HRV signal).

In the context of the claims and description of the present application, a phrase such as "within a given amount of time" or "within a given period of time" includes within its scope different levels of specificity. For example, for a prediction that the subject will likely ovulate within two days, the computer processor may generate a less specific output such as "You will likely ovulate within two days," or a more specific output such as "You will likely ovulate in approximately 1.5 days." Similarly, a phrase such as "in less than three days" includes within its scope different levels of specificity. For example, for a prediction that PMS will likely occur in less than three days, the computer processor may generate a less specific output such as "You will likely experience PMS in less than three days," or a more specific output such as "You will likely experience PMS in approximately two days."

Figure 4:
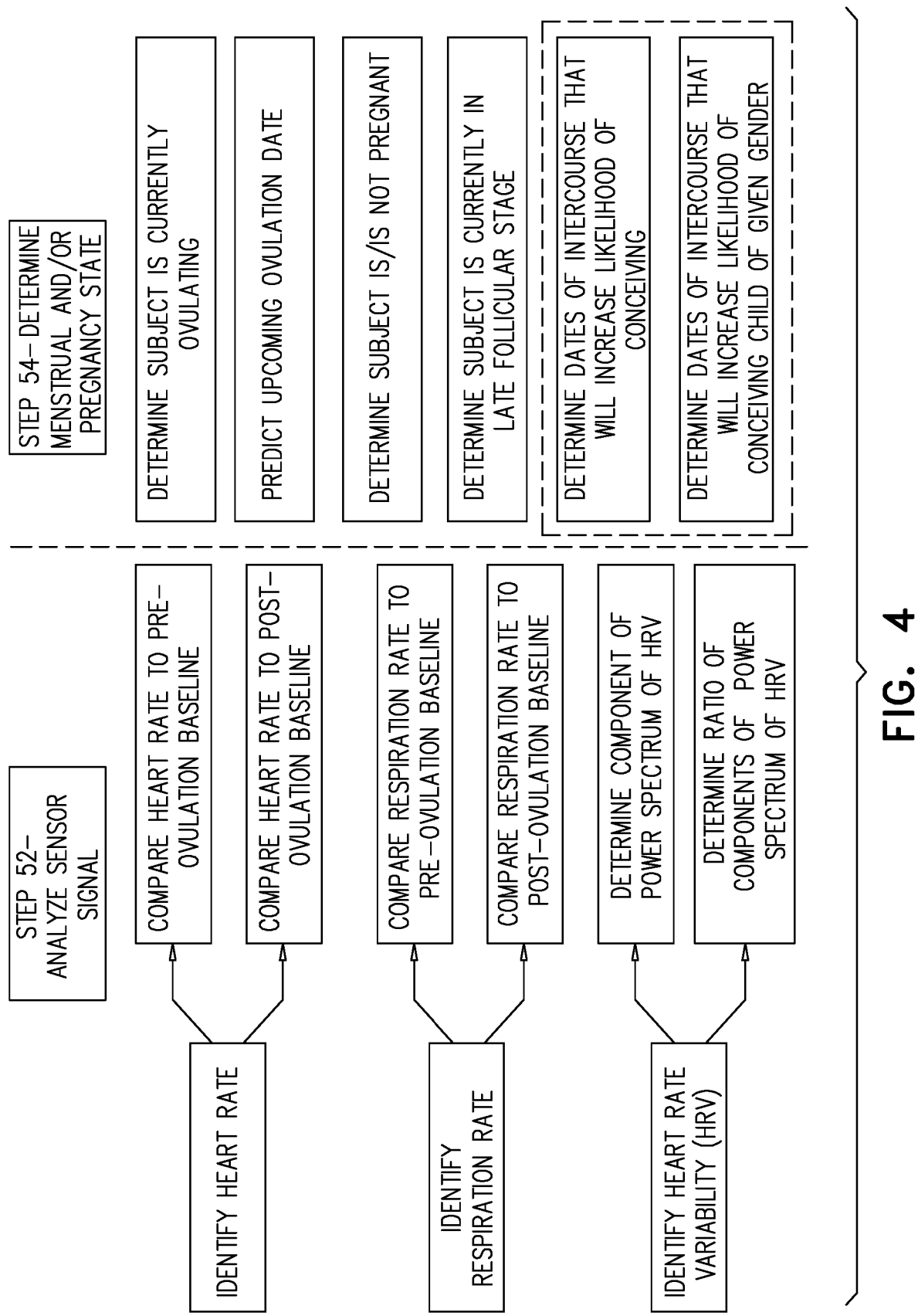
FIG. 4 is a schematic illustration showing steps of a method for automatically determining a menstrual state and/or a pregnancy state of the female subject, in accordance with some applications of the present invention.

Reference is now made to FIG. 4, which is a flowchart showing algorithms that are performed by computer processor 28, in accordance with some applications of the present invention. The left side of FIG. 4 shows some of the above-described algorithms, via which step 52 of FIG. 2 is performed, in accordance with some applications of the present invention. The right side of FIG. 4 shows examples of menstrual states and/or pregnancy states that are identified in step 54 of FIG. 2, and/or (inside the dashed box on the right side of FIG. 4) examples of data that are derived based upon the identified menstrual state and/or pregnancy state, in accordance with some applications of the present invention. It is noted the scope of the present invention is not limited to the examples shown in FIG. 4.

Figure 5:
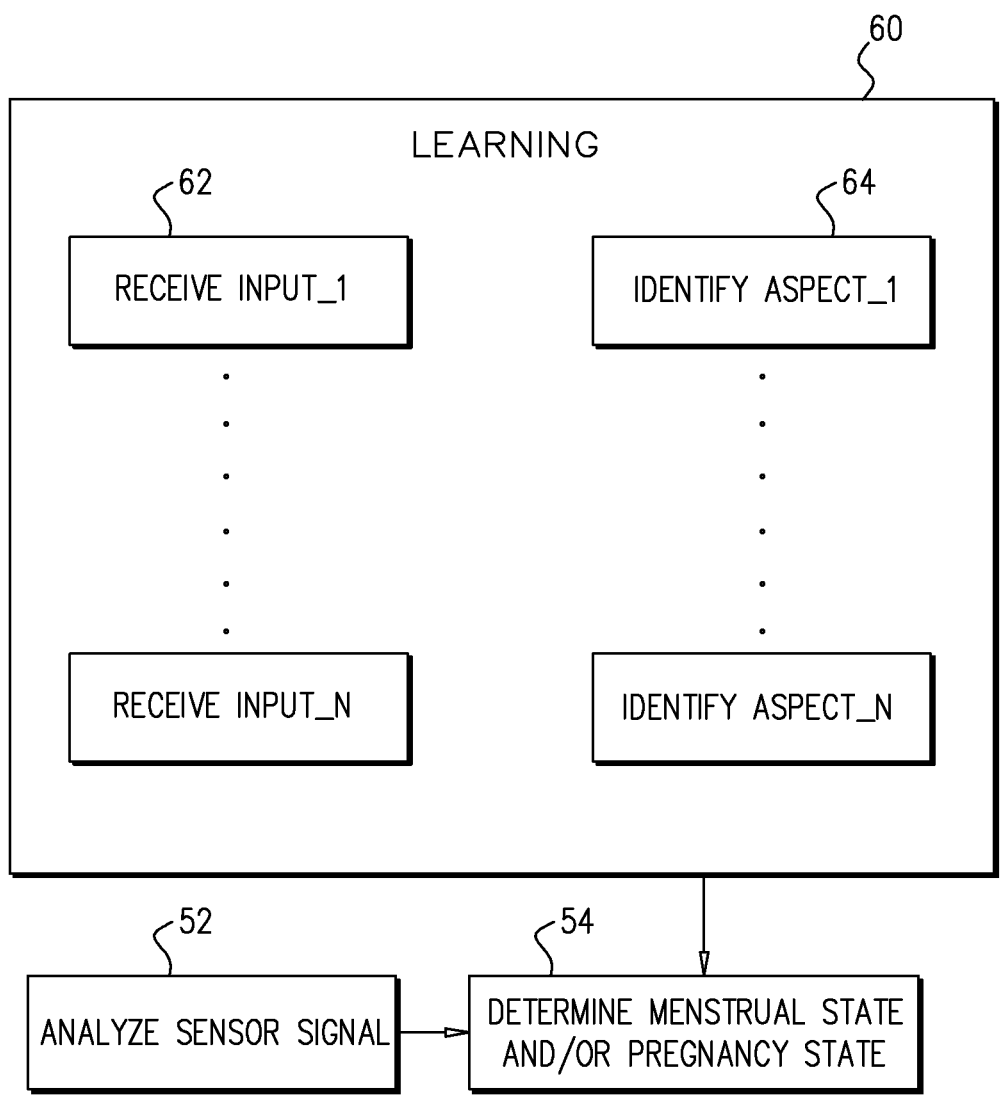
FIG. 5 is a flowchart showing steps of a method for automatically determining a menstrual state and/or a pregnancy state of the female subject that incorporate machine-learning techniques, in accordance with some applications of the present invention.

Reference is again made to FIG. 1. Reference is also made to FIG. 5, which is a flowchart showing steps of a procedure that is performed by computer processor 28, in accordance with some applications of the present invention. As described hereinabove, in some applications, apparatus 20 comprises a user interface. For some applications, at a learning step 60 (which includes a plurality of sub-steps, as described hereinbelow), computer processor 28 uses input from the user interface to learn a rule for identifying the condition of the subject. In particular, at least once (and typically more than once) prior to the identification of the currently-identified aspect of the sensor signal, the computer processor (i) receives, via the user interface, at an input-receiving step 62, an input that is indicative of the condition of the subject (e.g., the current menstrual state of the subject), and (ii) identifies an aspect of the sensor signal, at an aspect-identifying step 64. The computer processor then learns, at a rule-learning step 66, a condition-identification rule, or a condition-prediction rule, to facilitate the performance of step 54 of FIG. 2 (determining the subject's menstrual state and/or pregnancy state).

For example, FIG. 5 shows the computer processor receiving the input, and identifying the aspect of the sensor signal, a plurality of times, such that the computer processor collects a set of data points {(Aspect_i, Input_i)} for i=1 . . . N, i.e., {(Aspect_1, Input_1) . . . (Aspect_N, Input_N)}. Based at least on the plurality of data points, the computer processor implements a machine-learning algorithm to learn the rule, at rule-learning step 66. For example, the computer processor may implement a supervised learning algorithm to learn the rule. In some applications, the number of identified aspects is greater than the number of inputs (i.e., at least one "Aspect_i" does not have a corresponding "Input_i"), and the computer processor implements a semi-supervised learning algorithm to learn the rule.

In some applications, the computer processor continually improves the learned rule, based on feedback from the user. For example, if the computer processor identified that the subject was pregnant, and the identification was later found to be incorrect, the subject may report the incorrect identification to the computer processor, and the computer processor may modify the rule accordingly.

For some applications, computer processor is configured to incorporate non-subject-specific data into a machine learning-algorithm, in order to identify the subject's menstrual state and/or pregnancy state, generally in accordance with techniques described herein. For example, the computer processor may be configured to receive data (e.g., via a network) regarding measured parameters of other females, and the corresponding menstrual state(s) and/or pregnancy state(s) of those females. The computer processor is configured to use these data as additional inputs in a machine-learning algorithm, in order to identify the subject's menstrual and/or pregnancy state.

As shown in FIG. 5, for some applications, computer processor 28 performs the step of determining the subject's menstrual state and/or pregnancy state in response to the learned rule, in combination with the analysis of the sensor signal.

In general, learning step 60 may be applied to any of the menstrual state and/or pregnancy state identification applications described hereinabove, as well as to other similar applications. For example:

(i) The subject may provide one or more inputs indicative of whether she is pregnant, and the computer processor may identify the aspect of the sensor signal associated with each of the inputs. The computer processor may then learn a pregnancy-identification rule in response to the inputs and the identified aspects. The pregnancy-identification rule may then be used to identify, in response to the current sensor signal, whether the subject is pregnant.

(ii) The subject may provide one or more inputs indicative of the current phase of her menstrual cycle, and the computer processor may identify the aspect of the sensor signal associated with each of the inputs. The computer processor may then learn a phase-identification rule, and/or an ovulation-prediction rule, in response to the inputs and the identified aspects. The learned rule may then be used, in response to the current sensor signal, to identify the current phase of the subject's menstrual cycle, and/or predict an upcoming ovulation.

(iii) The subject may provide one or more inputs indicative of an occurrence of PMS, and the computer processor may identify the aspect of the sensor signal associated with each of the inputs. The computer processor may then learn a PMS-prediction rule in response to the inputs and the identified aspects. The PMS-prediction rule may then be used to predict, in response to the current sensor signal, an upcoming occurrence of PMS.

Reference is again made to FIG. 1. For some applications, computer processor 28 communicates with room-climate-regulation device 44, which may be an air-conditioning unit. For some women, changes from one phase in the menstrual cycle to another phase are accompanied by changes in climate sensitivity. Hence, in some applications, computer processor 28 performs step 56 of FIG. 2 (generating an output) by communicating a control signal to the room-climate-regulation device in response to the identified phase of the menstrual cycle. (Similarly, the computer processor may communicate the control signal in response to identifying whether the subject is pregnant.) For some applications, computer processor 28 receives an input from the subject (e.g., via user interface device 35) to facilitate the control of the room-climate-regulation device. For example, the subject may define a "profile" that covers different stages of the menstrual cycle, such that each stage is mapped to an appropriate temperature setting (e.g., using techniques that are generally similar to those described hereinbelow with reference to FIGS. 12-15). The computer processor then control the room-climate-regulation device based upon the defined profile, and in response to the current sensor signal.

In some applications, the computer processor is further configured, in response to analyzing the sensor signal, to identify a sleep stage of the subject during the subject's sleeping session. (To identify the sleep stage of the subject, the computer processor may utilize techniques described in US 2007/0118054 to Pinhas (now abandoned), which is incorporated herein by reference.) The identification or prediction of the subject's condition is then performed in response to an aspect of the sensor signal that is exhibited while the identified sleep stage is a particular sleep stage, and substantially not in response to any aspect of the sensor signal that is exhibited while the identified sleep stage is not the particular sleep stage.

For example, the computer processor may substantially restrict the analysis to slow-wave (i.e., deep) sleep, i.e., the computer processor may identify or predict the subject's condition substantially only in response to an aspect of the sensor signal that was exhibited during slow-wave sleep. In some cases, it may be advantageous to substantially exclude REM sleep from the analysis. For example, during REM sleep, dreaming of the subject may cause changes in heart rate which, with respect to the identification of the subject's menstrual stage, constitute unwanted "noise". On the other hand, in some applications, the analysis is substantially restricted to the REM sleep stage. For example, the HRV signal during REM sleep may, in some cases, be particularly indicative of the subject's current or upcoming condition.

While the scope of the present invention includes using data from the particular sleep stage, to the complete exclusion of all other sleep stages, the scope of the present invention also includes using data from sleep stages other than the particular sleep stage, to a certain limited extent. This is indicated, in the relevant portions of the claims and description of the present application, by the word "substantially." In particular, "substantially not in response to any aspect of the sensor signal that is exhibited while the identified sleep stage is not the particular sleep stage" means that even if data that is not from the particular sleep stage is used for the analysis, this data is used to a relatively small extent, such that it does not have a significant influence on the outcome of the analysis. For example:

(i) For a non-numeric output (e.g., an output indicative of whether the subject is pregnant), or a numeric output having a relatively small number of possible values, the "substantially excluded" data might not change the outcome in more than 5% of cases. In other words, in at least 95% of cases, the computer processor would output the same value, regardless of whether the substantially excluded data is used for the analysis.

(ii) For a numeric output having a relatively large number of possible values (e.g., an output that is generally continuous-valued, such as an expected amount of time until ovulation), the substantially excluded data might not change the value of the output by more than 5%. For example, if, when completely excluding the data, a value of 2.0 days were output, including the data in the analysis would not change the output by more than 0.1 days.

It is noted that the scope of the present invention includes restricting the analysis to more than one sleep stage. For example, the analysis may be restricted to all sleep stages except for REM sleep.

In some applications, in response to analyzing the sensor signal, the computer processor identifies the end of the chronologically-first or chronologically-second sleep cycle of the subject during the sleeping session. (For example, to identify the end of a sleep cycle, the computer processor may utilize techniques described above with respect to sleep-stage identification.) In such applications, alternatively or additionally to substantially restricting the analysis to a particular sleep stage, the computer processor may substantially restrict the analysis to data collected after the end of the chronologically-first or chronologically-second sleep cycle. (In this context, as before, the word "substantially" is to be understood to indicate that the computer processor does not necessarily completely exclude from the analysis data that is collected outside the specified portion of the sleeping session.) The inventors have observed that in some cases, data collected during the first and/or second sleep cycle may contain "artifacts," i.e., the data may reflect activities (e.g., eating) that the subject performed before going to sleep, and may thus "mislead" the computer processor. Hence, by substantially excluding the first and/or second sleep cycle from the analysis, these artifacts are substantially filtered out. Alternatively or additionally, the computer processor may substantially restrict the analysis to data collected at least a particular amount of time from the beginning of the sleeping session. For example, the computer processor may substantially exclude from the analysis any data that is collected less than two hours from the beginning of the sleeping session.

Alternatively or additionally to the above, in some applications, the computer processor may, in response to analyzing the sensor signal, determine a level of motion of the subject while the subject sleeps. In such applications, the computer processor may substantially restrict the analysis to data collected while the level of motion does not exceed a threshold. (Again, the word "substantially" is to be understood as explained above.) In this manner, motion artifacts in the sensor signal are substantially excluded from the analysis.

The scope of the present invention includes "substantial exclusion" of the first or second sleep cycle of the subject in any relevant context. In other words, the computer processor may identify or predict any physiological condition (i) in response to an aspect of the sensor signal that is exhibited following the end of the chronologically-first or chronologically-second sleep cycle, and (ii) substantially not in response to any aspect of the sensor signal that is exhibited before the end of the chronologically-first or chronologically-second sleep cycle. Furthermore, the analysis in which the first and/or second sleep cycle are excluded may be in response to a signal from any type of sensor, including those sensors that require compliance of the subject to monitor the subject.

Figure 6:
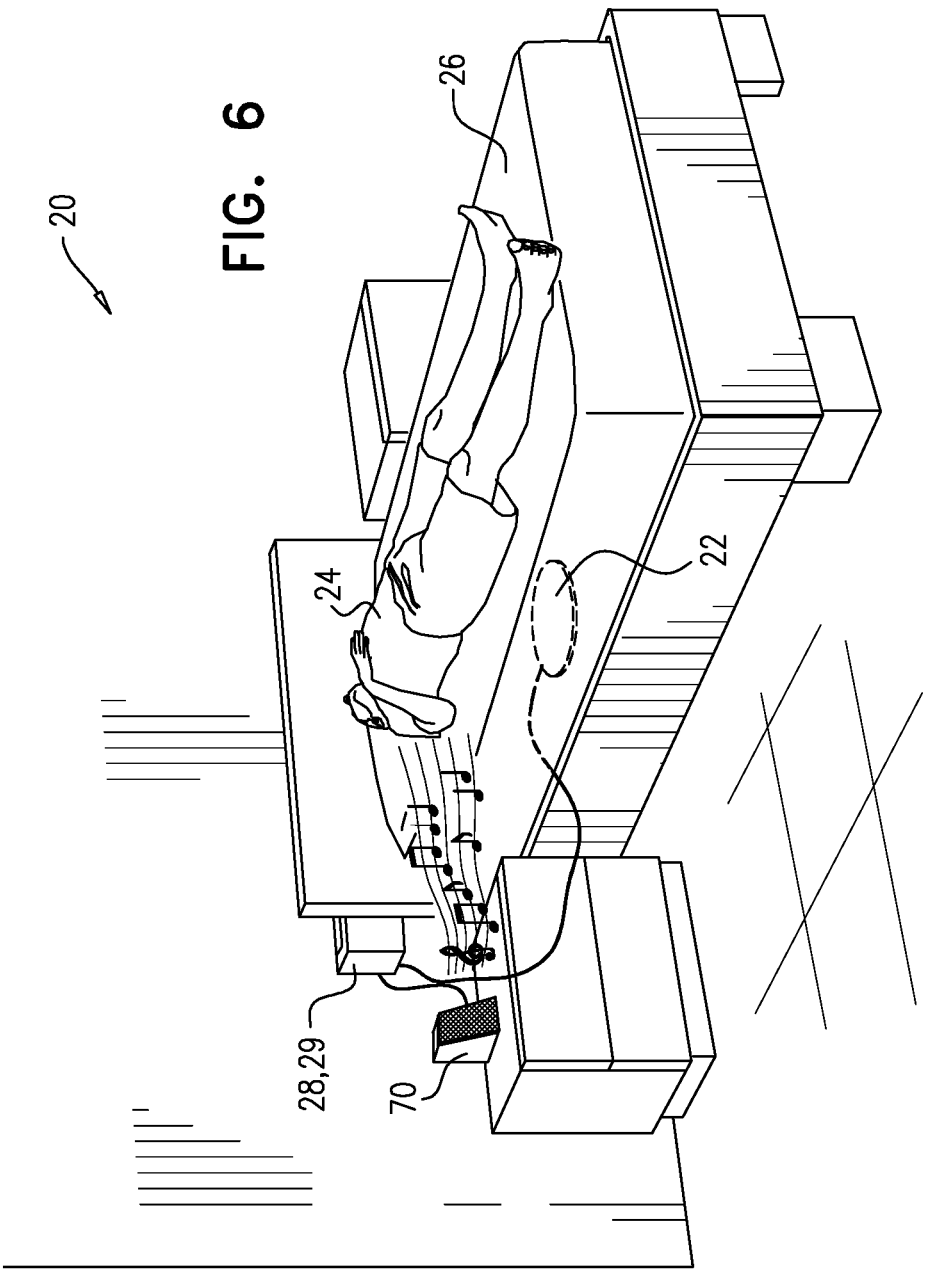
FIG. 6 is a schematic illustration of subject-monitoring apparatus, in accordance with some applications of the present invention.

Reference is now made to FIG. 6, which is a schematic illustration of subject-monitoring apparatus 20, in accordance with some applications of the present invention. Components of subject-monitoring apparatus 20 are as described hereinabove with reference to FIG. 1. Subject-monitoring apparatus 20 comprises a sensor 22, which is generally as described hereinabove, and is configured to monitor subject 24. It is noted that, in the applications described with reference to FIGS. 6-29, the subjects are typically male or female subjects. Subject-monitoring apparatus 20 includes a control unit, which is typically a computer processor, such as computer processor 28 described hereinabove. As described hereinabove, computer processor typically communicates with a memory 29. The computer processor is typically a control unit that performs the algorithms described herein, including analyzing the signal from sensor 22. It is noted that, in general, in the specification and claims of the present application, the terms "computer processor" and "control unit" are used interchangeably, since steps of the techniques described herein are typically performed by a computer processor that functions as a control unit. Therefore, the present application refers to component 28 both as a "computer processor" and a "control unit."

In response to the analyzing, control unit 28 controls a property (e.g., the content, genre, volume, frequency, and/or phase-shift) of a sound signal, and drives a speaker 70 to play the sound signal. Typically, as described hereinbelow, the property of the sound signal is controlled such as to help the subject fall asleep or remain asleep.

For example, if the subject is trying to fall asleep, the control unit may select a sound signal of the "relaxing nature sounds" genre, and may further select the content of the signal to be the sound of waves hitting the seashore. The control unit may further set the frequency of the sound signal (e.g., the frequency of the waves) to an offset less than the subject's current heart rate or respiratory rate, in order to facilitate slowing of the subject's heart rate and/or respiratory rate. In some applications, the control unit controls the offset, in response to analyzing the sensor signal; for example, as the heart rate of the subject approaches a target "relaxed" heart rate, the control unit may reduce the offset, such that the frequency of the sound signal is very close to or identical with the subject's heart rate. As the subject begins to fall asleep, the control unit may reduce the volume of the sound signal.

In some applications, the control unit controls a phase-shift of the sound signal with respect to a cardiac signal and/or a respiratory signal of the subject. For example, the control unit may cause the sound of a wave hitting the seashore to occur a given amount of time (e.g., 300 milliseconds) before or after each heartbeat of the subject, or a given amount of time (e.g., 1 second) after each expiration of the subject.

In some applications, the control unit ascertains that the subject is trying to fall asleep, at least in response to analyzing the sensor signal. For example, by analyzing the sensor signal, the control unit may ascertain that the subject is awake and is exhibiting a large amount of movement indicative of restlessness in bed. Alternatively or additionally, the ascertaining is in response to one or more other factors, such as a signal from a light sensor that indicates a low level of ambient light in the room, and/or the time of day. In response to ascertaining that the subject is trying to fall asleep, the control unit controls the property of the sound signal, as described hereinabove.

In some applications, by analyzing the sensor signal, the control unit ascertains a sleep stage of the subject, and controls the property of the sound signal in response to the ascertained sleep stage. For example, in response to ascertaining that the subject has entered a slow-wave (i.e., deep) sleep stage, the volume of the sound signal may be reduced to a relatively low level (e.g., zero). In identifying a sleep stage of a subject, as described throughout the present application, the control unit may use one or more of the techniques described in (a) US 2007/0118054 to Pinhas (now abandoned), (b) Shinar et al., Computers in Cardiology 2001; Vol. 28: 593-596, and (c) Shinar Z et al., "Identification of arousals using heart rate beat-to-beat variability," Sleep 21(3 Suppl):294 (1998), each of which is incorporated herein by reference. For example, as described by paragraphs [0073], [0181], and [0185]-[0187] of US 2007/0118054 to Pinhas:

[paragraph 0073 of Pinhas] Other embodiments of the invention include methods and systems for monitoring a clinical condition including monitoring clinical parameters during sleep and identifying sleep stages and comparing the clinical parameters in at least one sleep stage to baseline clinical parameters for that sleep stage. The methods and device for identifying sleep stages may include a motion acquisition module, a pattern analysis module and an output module, as described below.

[Paragraph 0181 of Pinhas] In an embodiment of the present invention, system 10 is adapted to monitor parameters of the patient including breathing rate, heart rate, coughing counts, expiration/inspiration ratios, augmented breaths, deep inspirations, tremor, sleep cycle, and restlessness patterns, among other parameters. These parameters are defined herein as "clinical parameters."

[Paragraph 0185 of Pinhas] Although system 10 may monitor breathing and heartbeat patterns at any time, for some conditions it is generally most effective to monitor such patterns during sleep at night. When the subject is awake, physical and mental activities unrelated to the monitored condition often affect breathing and heartbeat patterns. Such unrelated activities generally have less influence during most night sleep. For some applications, system 10 monitors and records patterns throughout all or a large portion of a night. The resulting data set generally encompasses typical long-term respiratory and heartbeat patterns, and facilitates comprehensive analysis. Additionally, such a large data set enables rejection of segments contaminated with movement or other artifacts, while retaining sufficient data for a statistically significant analysis.

[Paragraph 0186 of Pinhas] Reference is again made to FIG. 2. Data acquisition module 20 typically comprises circuitry for processing the raw motion signal generated by motion sensor 30, such as at least one pre-amplifier 32, at least one filter 34, and an analog-to-digital (A/D) converter 36. Filter 34 typically comprises a band-pass filter or a low-pass filter, serving as an anti-aliasing filter with a cut-off frequency of less than one half of the sampling rate. The low-passed data is typically digitized at a sampling rate of at least 10 Hz and stored in memory. For example, the anti-aliasing filter cut-off may be set to 10 Hz and the sampling rate set to 40 Hz. For some applications, filter 34 comprises a band-pass filter having a low cutoff frequency between about 0.03 Hz and about 0.2 Hz, e.g., about 0.05 Hz, and a high cutoff frequency between about 1 Hz and about 10 Hz, e.g., about 5 Hz. Alternatively or additionally, the output of motion sensor 30 is channeled through several signal-conditioning channels, each with its own gain and filtering settings tuned according to the desired signal. For example, for breathing signals, a relatively low gain and a frequency passband of up to about 5 Hz may be used, while for heartbeat signals, a moderate gain and a slightly higher frequency cutoff of about 10 Hz may be used. For some applications, motion sensor 30 is additionally used for registration of acoustic signals, for which a frequency passband of about 100 Hz to about 8 kHz is useful.

Figure 26:
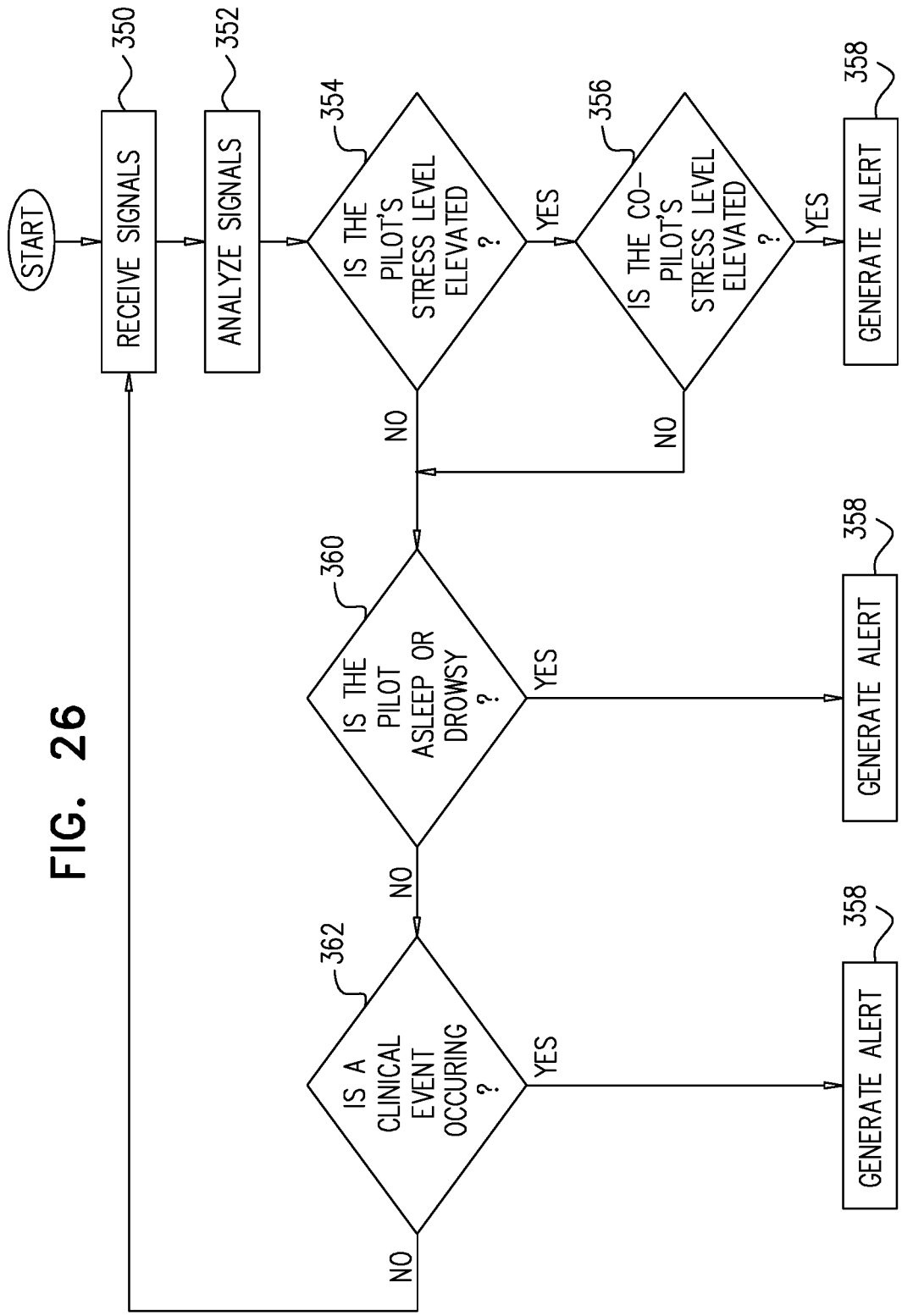
FIG. 26 shows a flow chart depicting aspects of a method for monitoring a subject in a vehicle, in accordance with some applications of the present invention.
Figure 27:
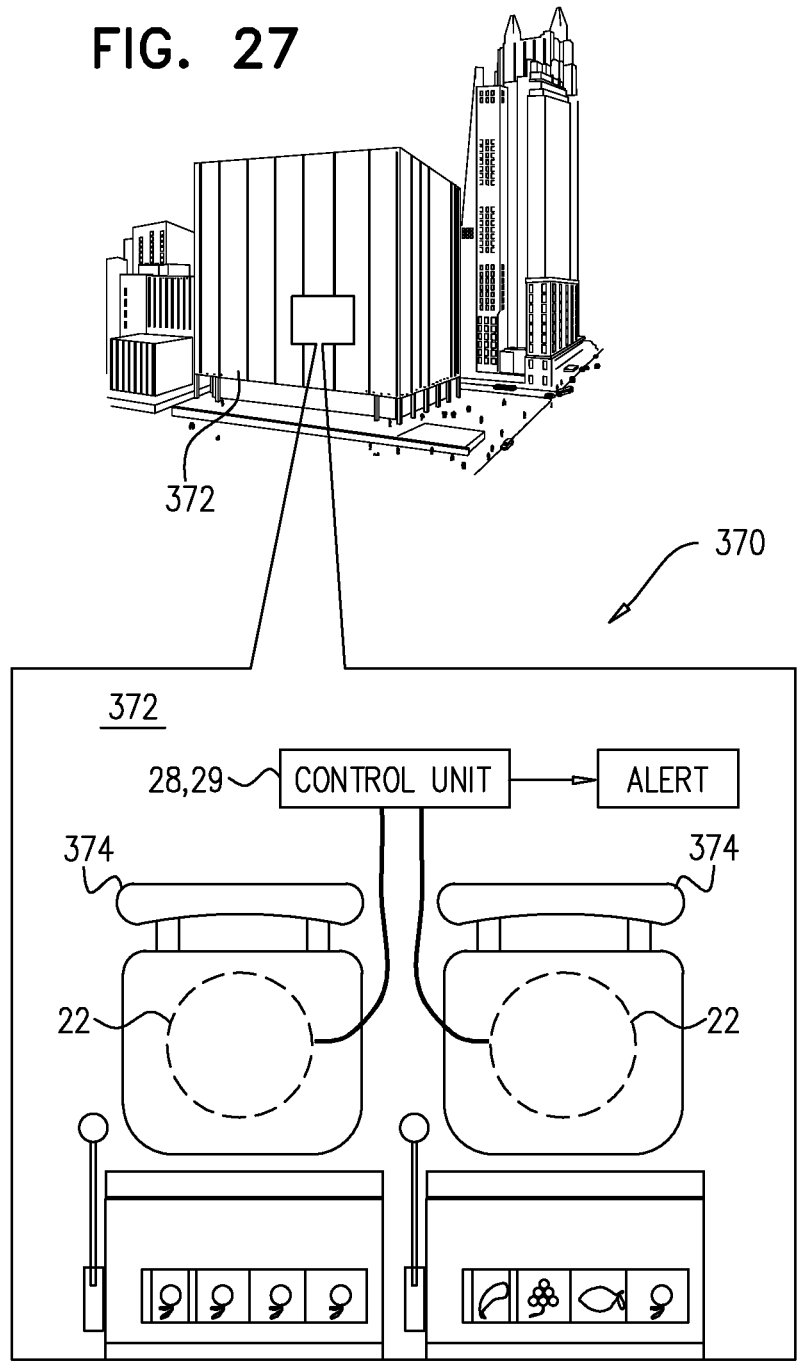
FIG. 27 is a schematic illustration of apparatus for monitoring a subject in a casino, in accordance with some applications of the present invention.

[Paragraph 0187 of Pinhas] Chronic conditions often affect sleep cycles. For example, asthma affects the sleep cycle and the quality of sleep as described by Fitzpatrick and Engleman in Thorax, Vol. 46, pp. 569-573, which is incorporated herein by reference. In an embodiment of the present invention, system 10 is adapted to monitor heartbeat patterns of subject 12. The heart beat pattern is analyzed to identify peaks and measure distance between the peaks. FIG. 26 shows a typical signal measured by an embodiment of the present invention. Line 510 denotes the signal after a filter for the heartbeat signal (0.8-2.0 Hz). As is known in the art, the "R-R interval" is a characteristic of a heart beat signal, for example, an ECG trace. The R-R interval is the time period between successive R waves of the heart beat signal. According to aspects of the present invention, the R-R signal is calculated by measuring the time distance between each pair of peak, e.g., 511 to 512 and 513 to 514, and then dividing 60 seconds by that distance to receive the instantaneous heart rate in beats per minute (that is, 60 [secs./min.]/(R-R) [secs./beat]=60/(R-R) [beats/min.]). A sample result is shown in FIG. 27. This data is used to identify sleep stages using for example algorithms as described by Shinar et al. in Computers in Cardiology 2001, Vol. 28: 593-596 which is incorporated herein by reference.

Typically, the control unit controls the property of the sound signal further in response to a historical physiological parameter of the subject that was exhibited in response to a historical sound signal. For example, the control unit may "learn" the subject's typical responses to particular sound-signal properties, and control the sound signal in response thereto. Thus, for example, if the subject has historically responded well to a "relaxing nature sounds" genre, but less so to a "classical music" genre, the control unit may select the former genre for the subject. To determine whether the subject has historically responded well to particular properties of the sound signal, the control unit looks at some or all of historical physiological parameters such as a quality of sleep, a time-to-fall-asleep, a heart-rate-variability, a change in heart rate, a change in respiratory rate, a change in heart-rate-variability, a change in blood pressure, a rate of change in heart rate, a rate of change in respiratory rate, a rate of change in heart-rate-variability, and a rate of change in blood pressure.

In some applications, the control unit controls the frequency of the sound signal by synthesizing the sound signal, or by selecting a pre-recorded sound signal that has the desired frequency; in other words, the control unit selects the content of the signal, without the user's input. In other applications, the control unit selects content of the sound signal in response to a manual input, e.g., an input entered via user interface device 35 (FIG. 1). For example, the subject may select a particular piece of classical music, and the control unit may then control properties (such as the frequency, i.e., the tempo) of that particular piece. This may be done, for example, using appropriate software, such as Transcribe!™ by Seventh String Software of London, UK.

Figure 7:
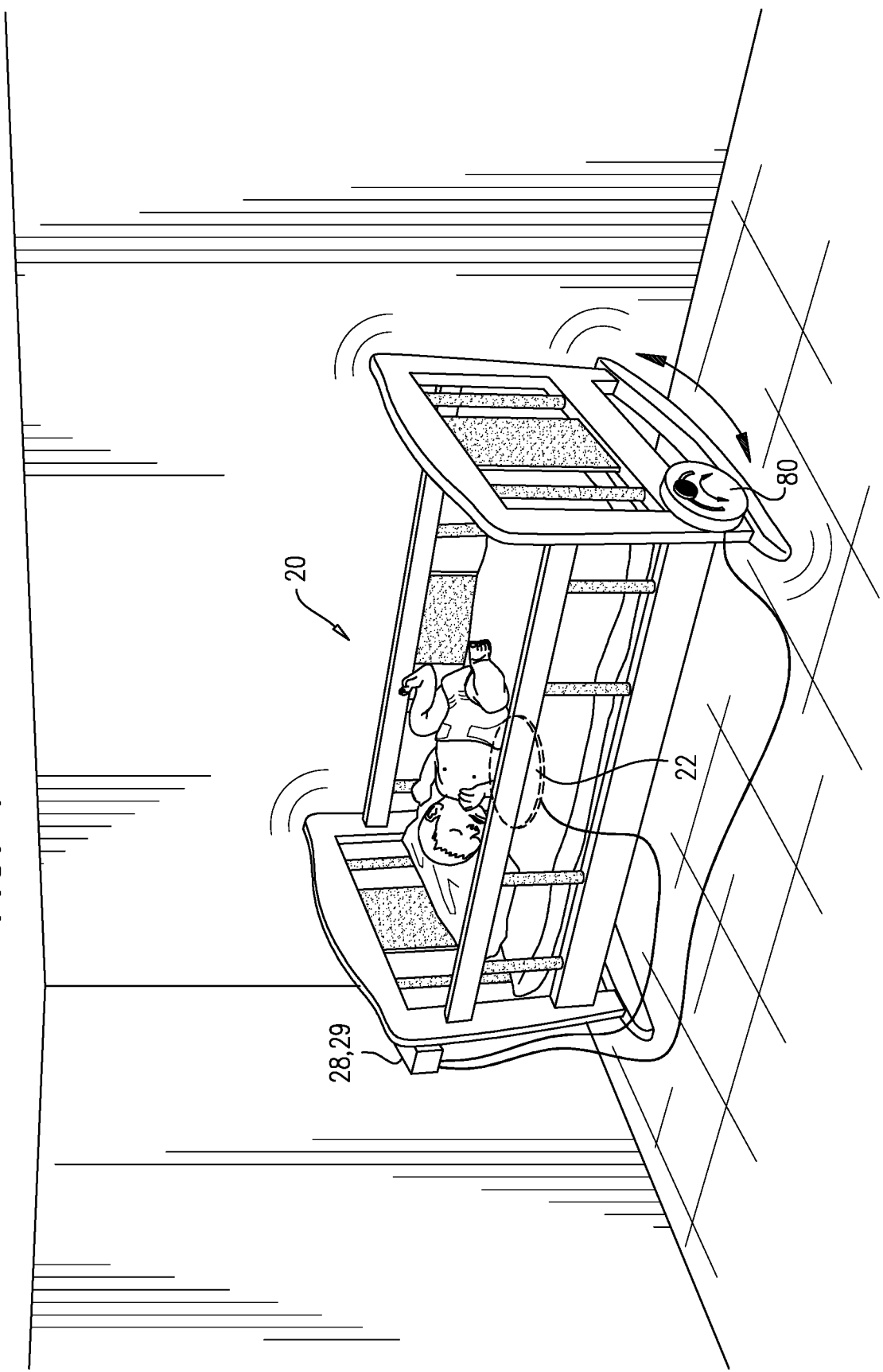
FIG. 7 is a schematic illustration of subject-monitoring apparatus, in accordance with some applications of the present invention.

Reference is now made to FIG. 7, which is a schematic illustration of apparatus 20, in accordance with some applications of the present invention. Components of subject-monitoring apparatus 20 are as described hereinabove with reference to FIG. 1. Subject-monitoring apparatus 20 comprises a sensor 22, which is generally as described hereinabove, and is configured to monitor subject 24. Subject-monitoring apparatus 20 includes a control unit, which is typically a computer processor, such as computer processor 28 described hereinabove. As described hereinabove, computer processor typically communicates with a memory 29. The computer processor is typically a control unit that performs the algorithms described herein, including analyzing the signal from sensor 22.

In some applications, e.g., with an infant subject, the control unit drives a vibrating or rocking mechanism 80 by sending a control signal to the mechanism, alternatively or additionally to driving the speaker to play the sound signal. For example, in response to analyzing the sensor signal, the control unit may ascertain that the infant is not sleeping. In response to the ascertaining, the control unit may control a device such as the Lullabub Cot Rocker™ by Babyhugs Pty of Mermaid Beach, Australia, in order to help the infant fall asleep. In some applications, the controlling of the vibrating or rocking mechanism is also in response to historical sleep-related data of the subject. For example, if the infant has historically responded well to vibrations at a particular frequency, the control unit may select that particular frequency. (The historical sleep-related data may include any of the parameters described above, such as time-to-fall-asleep or heart-rate-variability.)

In some applications, in response to the subject awakening prematurely, the control unit "recreates" the environment that originally helped the subject fall asleep. For example, if a particular sound and/or rocking setting helped the infant fall asleep at the beginning of the night, the same setting may be used to help the infant fall asleep, upon the infant waking up prematurely.

In some applications, the control unit performs a "sweep" (or "optimization routine") over various sound and/or vibration and/or rocking settings, in order to learn which settings are more conducive to sleep of the subject, relative to other settings. For example, over the course of one or more sleeping sessions, the control unit may vary a parameter such as a sound frequency, a sound amplitude, a vibration frequency, a vibration amplitude, a rocking frequency, or a rocking amplitude. By analyzing the sensor signal, the control unit identifies a value of the parameter that is more conducive to sleep of the subject, relative to other values. Subsequent to the learning, the control unit sets the selected parameter to the identified value. The sweep may be performed before every sleeping session, or alternatively, at less frequent intervals, depending on how well the subject is responding to the identified "optimal" settings.

Figure 8:
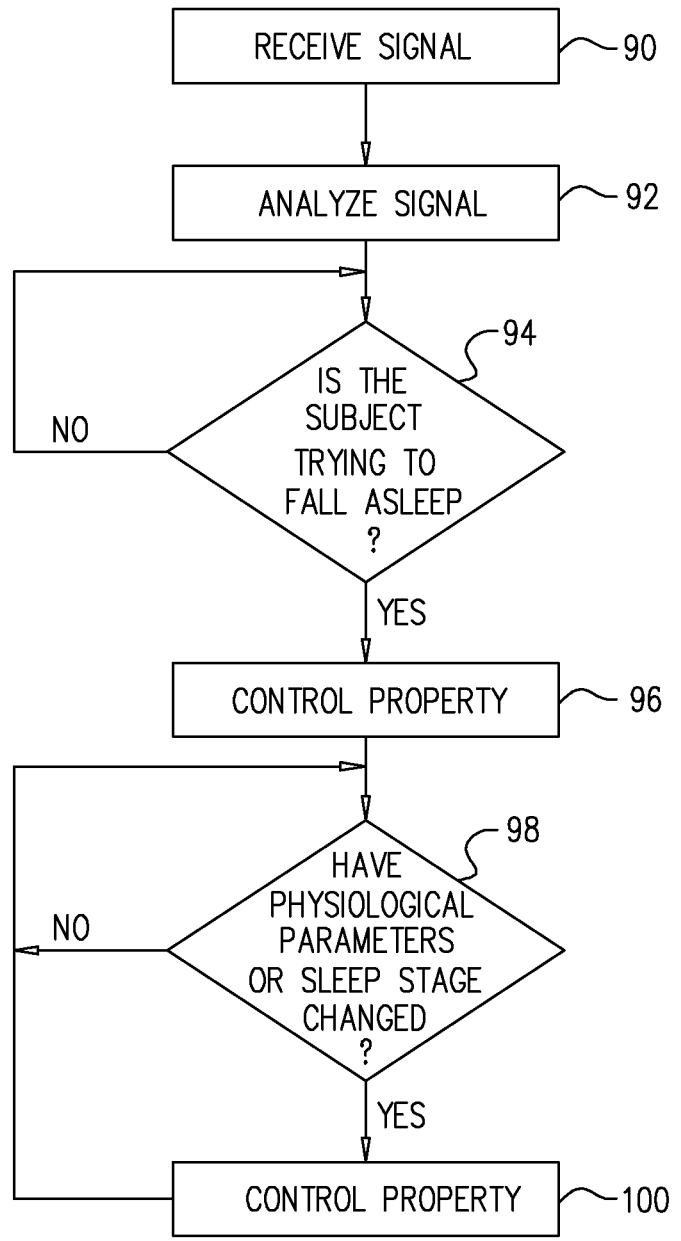
FIG. 8 shows a flow chart depicting aspects of the functioning of subject-monitoring apparatus, in accordance with some applications of the present invention.

FIG. 8 shows a flow chart depicting aspects of the functioning of subject-monitoring apparatus 20, as described hereinabove with reference to FIGS. 6-7, in accordance with some applications of the present invention. At a signal-receiving step 90, the control unit receives the signal from the sensor. At a signal-analyzing step 92, the control unit analyzes the signal. Then, at an is-subject-trying-to-fall-asleep step 94, the control unit ascertains whether the subject is trying to fall asleep. (In the context of the claims and description of the present application, the phrase "trying to fall asleep" does not necessarily connote a conscious attempt to sleep. For example, in the case of a young child, e.g., an infant, "trying to fall asleep" may simply indicate that the child is lying in bed.) If the control unit ascertains that the subject is trying to fall asleep, the control unit controls (i.e., sets) a property of the sound signal and/or vibration/rocking mechanism, at a property-controlling step 96. Then, the control unit repeatedly checks for changes in physiological parameters (e.g., a slowing of heart rate), and/or changes in the sleep stage of the subject, at a checking step 98. In response to identifying a change, the control unit again controls a property of the sound signal and/or vibration/rocking mechanism, in step 100.

Figure 9:
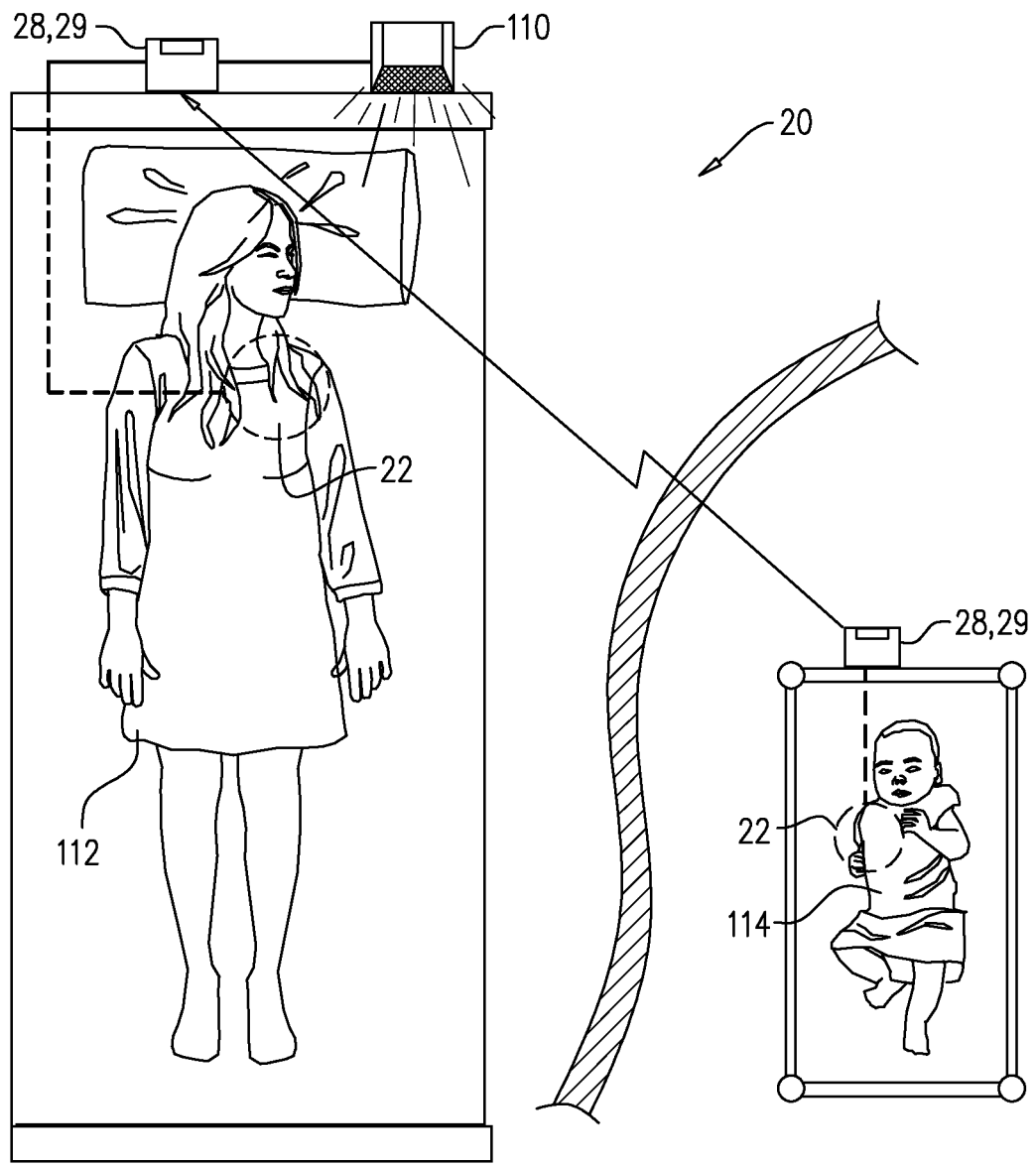
FIG. 9 is a schematic illustration of apparatus for use with an alerting device, in accordance with some applications of the present invention.

Reference is now made to FIG. 9, which is a schematic illustration of subject-monitoring apparatus 20 for use with an alerting device 110, in accordance with some applications of the present invention. Components of subject-monitoring apparatus 20 are as described hereinabove with reference to FIG. 1. Subject-monitoring apparatus 20 comprises one or more sensors 22, which are generally as described hereinabove, and are configured to monitor a care-provider 112 and a care-receiver 114 (the care-provider and care-receiver corresponding to subject 24 in FIG. 1). Subject-monitoring apparatus 20 includes a control unit, which is typically a computer processor, such as computer processor 28 described hereinabove. As described hereinabove, computer processor typically communicates with a memory 29. The computer processor is typically a control unit that performs the algorithms described herein, including analyzing the signal from sensor 22.

Apparatus 20, as shown in FIG. 9, generally facilitates the provision of care by care-provider 112 for care-receiver 114. As shown in FIG. 9, at least one sensor 22 monitors sleep of care-provider 112 and sleep of care-receiver 114, and generates a signal in response thereto. For example, one sensor 22 may monitor sleep of care-provider 112, while another sensor 22 monitors sleep of care-receiver 114. (The two sensors may be directly in communication with a single control unit 28, or alternatively, as shown in the figure, may communicate with respective control units that are in communication with each other.) Control unit 28 analyzes the signal, and in response thereto, drives alerting device 110 to alert (e.g., wake) the care-provider, in order for the care-provider to provide care to the care-receiver. In some situations, the care-receiver may wish to receive advance warning of the upcoming care-providing, rather than have the care-provider suddenly intrude. Thus, in some applications, the control unit drives a second alerting device to alert the care-receiver.

A typical scenario, in which care-provider 112 is a mother and care-receiver 114 is a newborn baby, is depicted in FIG. 9. A newborn baby is generally fed several times a night; these multiple feedings are typically disruptive to the sleep of both the mother and the baby. Apparatus 20 generally reduces this disruption, by timing the feedings in accordance with the sensor signal(s). For example, the control unit may ascertain, by analyzing the signal(s), a sleep stage of both the mother and the baby. If both the mother and the baby are sleeping lightly or are awake, the control unit may identify the current time as an opportune feeding time, and may consequently drive the alerting device to alert the mother. (In general, the "best" sleep stage is "awake"; next, in order of preference, are light sleep, REM, and slow-wave sleep, i.e., deep sleep.) Identifying an opportune feeding time typically involves taking into account one or more additional factors such as a desired number of feedings per night, a minimum spacing between feedings, and a maximum spacing between feedings. (These factors may be received as inputs, e.g., via user interface device 35 (FIG. 1).) Control unit 28 is configured to take these factors into account.

Control unit 28 is also configured to handle complex scenarios in which identifying an "optimal alerting time" is more difficult, such as where the sleep cycles of the two parties are generally not in synch with each other. (For example, one of the parties may typically be in a deep sleep whenever the other party is in a light sleep.) To handle these scenarios, the control unit may make use of historical sleep-related data of the care-provider and/or the care-receiver, e.g., using techniques as described hereinbelow. For example, if the historical data shows that the care-provider typically takes longer to fall asleep than the care-receiver, the control unit may give greater weight to the sleep stage of the care-provider, relative to the sleep stage of the care-receiver. (Thus, for example, the control unit may alert the care-provider if the care-provider is awake, even if the care-receiver is in a deep sleep.) The control unit may also use the historical data to predict upcoming changes. For example, the control unit may predict that the deep-sleeping party will, within a given period of time, move into an REM sleep-stage or a light sleep-stage, while the other party will remain in a light sleep-stage. In response to this prediction, the control unit may withhold the alert for the given period of time, rather than unnecessarily disturb the deep-sleeping party. Statistical averages based on age, gender, etc. may be used, alternatively or additionally to the historical data.

Figure 10:
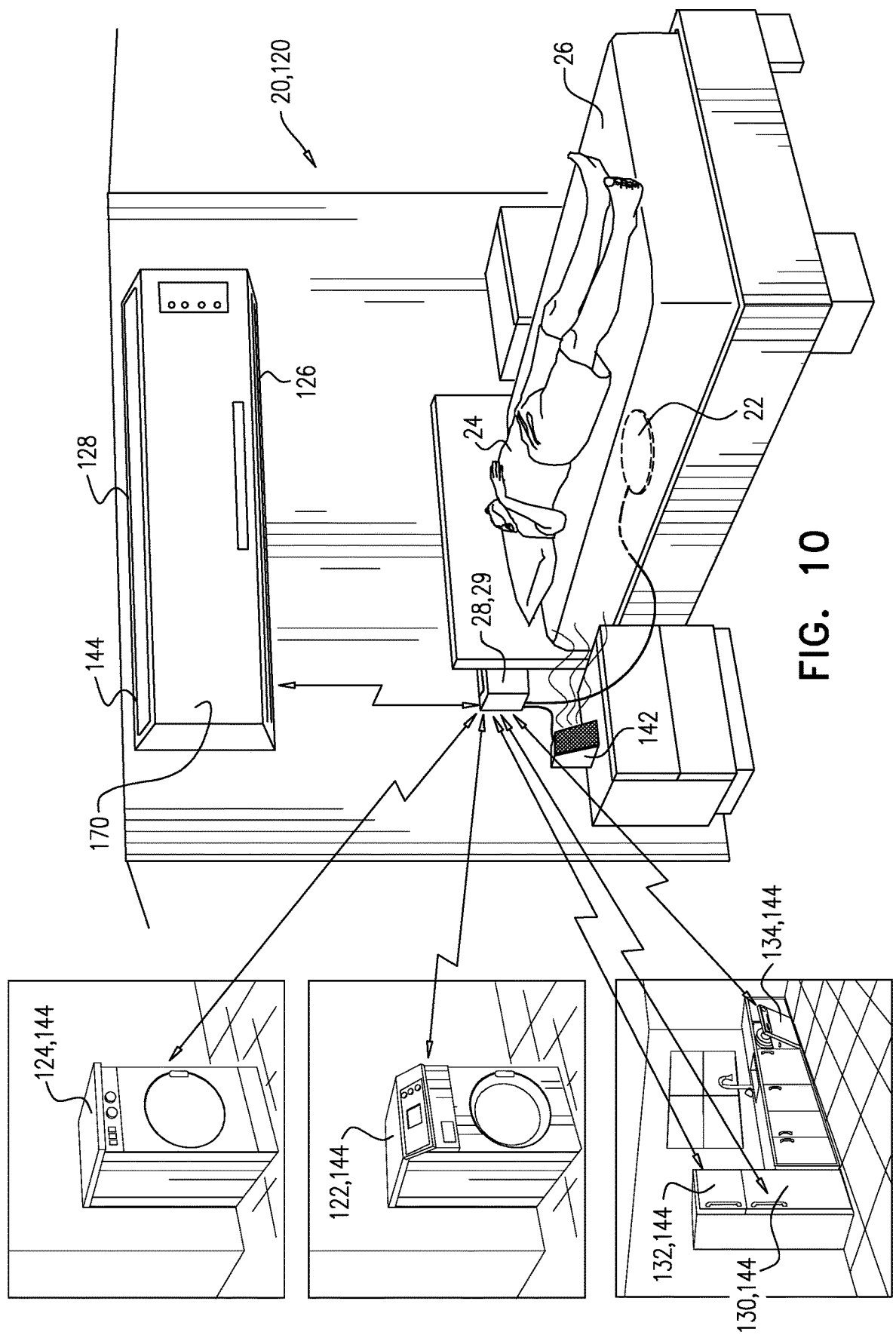
FIG. 10 is a schematic illustration of subject-monitoring apparatus being used with a noise-making device, such as a home appliance, in accordance with some applications of the present invention.

Reference is now made to FIG. 10, which is a schematic illustration of subject-monitoring apparatus 20 being used with a noise-making device, such as a home appliance, in accordance with some applications of the present invention. Components of subject-monitoring apparatus 20 are as described hereinabove with reference to FIG. 1. Subject-monitoring apparatus 20 comprises a sensor 22, which is generally as described hereinabove, and is configured to monitor subject 24. Subject-monitoring apparatus 20 includes a control unit, which is typically a computer processor, such as computer processor 28 described hereinabove. As described hereinabove, computer processor typically communicates with a memory 29. The computer processor is typically a control unit that performs the algorithms described herein, including analyzing the signal from sensor 22.

Sensor 22 is used to monitor sleep of subject 24 and to generate a signal in response thereto. By analyzing the signal, control unit 28 ascertains a sleep stage of the subject, and in response thereto, controls the home appliance. Sensor 22 and control unit are typically generally similar to sensor 22 and control unit 28 described hereinabove. Typically, a method 120 (depicted in FIG. 10) is practiced in order to reduce the extent to which noise from the appliance disturbs the sleep of the subject. Thus, for example, the control unit may activate the home appliance in response to ascertaining that the sleep stage of the person is a slow-wave (i.e., deep) sleep stage, and/or inhibit activation of the home appliance in response to ascertaining that the sleep stage of the subject is a light-sleep stage. Method 120 is typically for use with one or more noise-making home appliances such as a washing machine 122, a dryer 124, an air conditioner 126, a heater 128, a refrigerator 130, a freezer 132, and a dishwasher 134. (For some applications, as shown, an air conditioner and a heater may be combined into a single room-climate-regulation device 170.)

In some applications, the home appliance is controlled in response to historical sleep-related data of the subject. For example, the control unit may "learn" the subject's tolerance to noise, and control the appliance in response thereto. Thus, for example, if the control unit learns that the subject is particularly tolerant to noise, the control unit may activate the appliance even if the subject is not in a deep sleep.

As shown in FIG. 10, subject-monitoring apparatus 20 may include a first noise-making device 142 (e.g., a noise-cancelation speaker or white-noise-generating speaker) and the apparatus is used with a second noise-making device 144, in accordance with some applications of the present invention. Second noise-making device 144 may include, for example, any of the home appliances shown in FIG. 10. For some subjects, particularly light sleepers in small domiciles, activation of one or more of these appliances is likely to be disturbing to sleep. Apparatus 140 generally reduces this disturbance, by activating first noise-making device 142 to cancel or drown out the noise from the second noise-making device 144.

Figure 11:
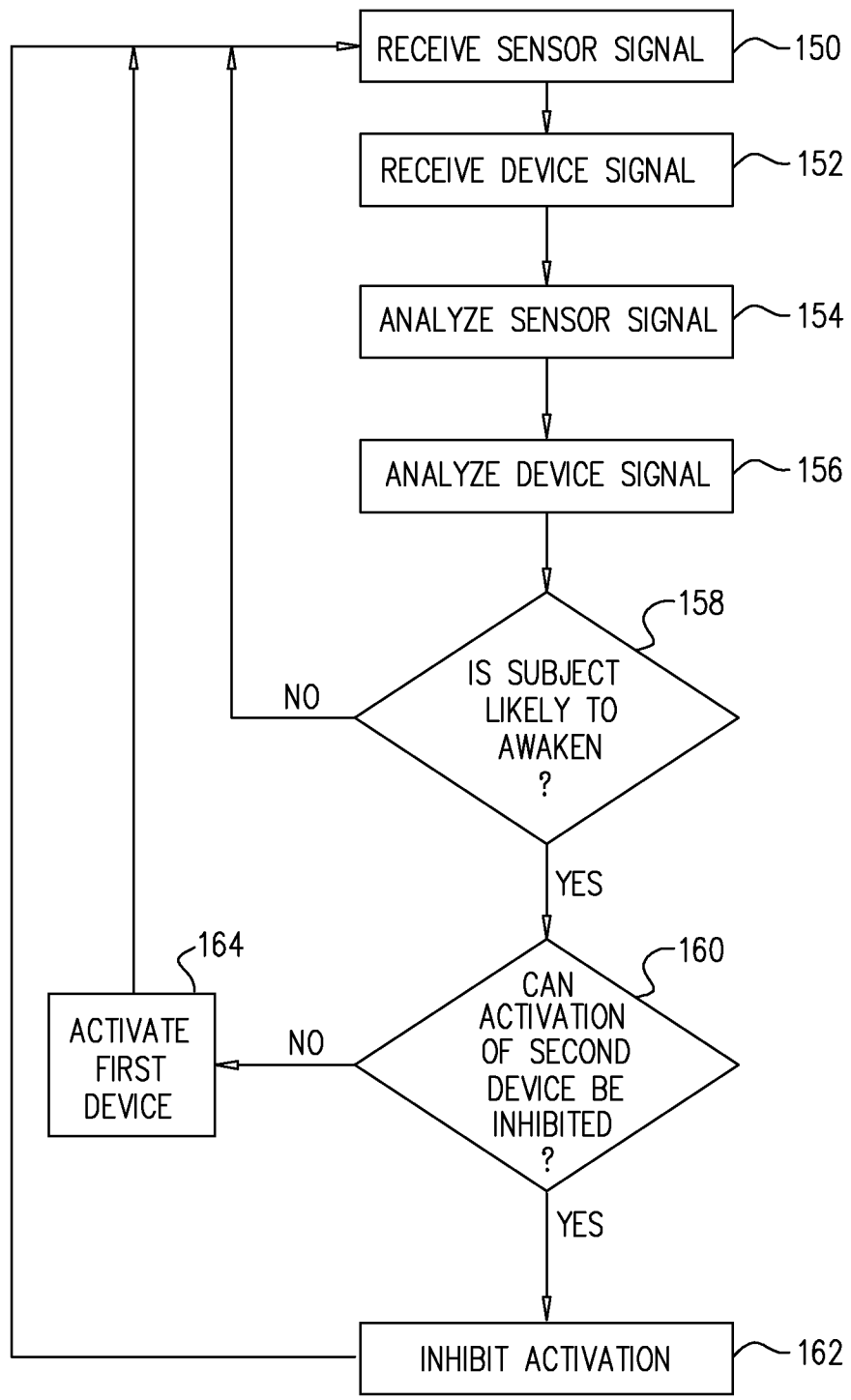
FIG. 11 shows a flow chart depicting aspects of the functioning of apparatus for use with noise-making devices, in accordance with some applications of the present invention.

Reference is now additionally made to FIG. 11, which shows a flow chart depicting aspects of the functioning of apparatus 20, in accordance with some applications of the present invention. At a sensor-signal-receiving step 150, the control unit receives the signal from the sensor. At a device-signal-receiving step 152, the control unit receives a device signal from the second noise-making device. In response to analyzing (a) the sensor signal at a sensor-signal-analyzing step 154, and (b) the device signal at a device-signal-analyzing step 156, the control unit, at an ascertaining step 158, ascertains if the subject is likely to awaken due to an upcoming activation of the second noise-making device. In a decision-making step 160, the control unit determines whether it is advisable to inhibit the activation of the second noise-making device. In response to the decision-making step, the control unit may "prefer" to inhibit activation of the second noise-making device, at an inhibiting step 162. However, if it is not prudent to do so (e.g., the food in refrigerator 138 will begin to spoil if the activation of the refrigerator is inhibited), the control unit will activate first noise-making device 146 instead, in activation step 164.

Referring again to FIG. 10, room-climate-regulation device 170 (e.g., a thermoregulation device such as heater 128 and/or an air conditioner 126) is shown, in accordance with some applications of the present invention. For some applications of the present invention, in response to analyzing the sensor signal from sensor 22, control unit 28 identifies a sleep stage of subject 24. In response to the identified sleep stage, the control unit controls room-climate-regulation device 170 by sending a control signal (e.g., wirelessly) to the room-climate-regulation device. For example, the control unit may control a noise-emission of the room-climate-regulation device (e.g., by controlling the rotating speed of a fan, such as an air conditioner fan), and/or adjust a temperature and/or humidity setting of the room-climate-regulation device. (Typically, the control unit is configured to control the noise-emission of the room-climate-regulation device even without adjusting a temperature setting of the room-climate-regulation device.)

In some cases, the control unit may increase a noise level of the room-climate-regulation device in response to the identified sleep stage not being a slow-wave (i.e., deep) sleep stage. A subject who is awake or is sleeping lightly may desire "white noise" in order to drown out other ambient noise and/or lull the subject to sleep; in such cases, the control unit increases the noise level of the room-climate-regulation device. Conversely, the control unit may decrease the noise level in response to the identified sleep stage being a slow-wave sleep stage, since a deep-sleeping subject typically requires less white noise.

In other cases, the control unit may increase the noise level of the room-climate-regulation device (e.g., by turning the device on) in response to the identified sleep stage being a slow-wave sleep stage, and/or decrease the noise level of the room-climate-regulation device (e.g., by turning the device off) in response to the identified sleep stage not being a slow-wave sleep stage. This may be appropriate, for example, if the subject is easily disturbed by noise, and prefers that the room-climate-regulation device makes noise only when the subject is in a deep sleep. (In other words, the subject may want to defer the regulation of temperature until the subject is sleeping deeply.)

In some applications, the control unit is configured to control the noise-emission of the room-climate-regulation device further in response to an ambient noise level. For example, the control unit may increase the white noise emission of the device only if the level of ambient noise is greater than a threshold.

In some applications, the apparatus shown in FIG. 10 performs at least some of the functions of apparatus 20 as shown in FIG. 6, with room-climate-regulation device 170 taking the place of speaker 70. For example, the control unit may be configured to control a frequency and/or a phase-shift of emitted noise of the room-climate-regulation device in response to a heart rate and/or a respiratory rate of the subject. Such applications typically require that the room-climate-regulation device be specially configured. For example, an air conditioner fan may be configured such that the rotating speed of its blades can automatically vary in a regular (e.g., sinusoidal) fashion, such that the amplitude of the emitted noise also varies in a regular fashion. The amplitude of the emitted noise can thus be made to have a particular frequency (e.g., slightly less than the heart rate of the subject), and/or a particular phase-shift (e.g., such that the highest fan-speed is reached at a particular offset from each heartbeat of the subject).

In some applications, the control unit controls the frequency and/or phase-shift of the emitted noise further in response to the identified sleep stage of the subject. For example, in response to the subject being awake, the control unit may set the frequency of the speed oscillations of the fan (and hence, the frequency of the emitted noise) to be slightly less than the heart rate of the subject, in order to help the subject fall asleep. In general, apparatus 20 as shown in FIG. 10 may be used in combination with techniques described hereinabove with reference to FIGS. 6-8, mutatis mutandis.

Studies show that dynamically regulating the temperature of a subject's sleep environment may improve the subject's sleep quality. For example, maintaining a steady temperature may increase the slow-wave-sleep (SWS) ratio, and cooling the bed during rapid-eye-movement (REM) sleep may increase the REM sleep share rate. In some applications, the control unit is configured, in response to the identified sleep stage, to control a temperature setting of the room-climate-regulation device. For example, the control unit may be configured to lower the temperature setting of the room-climate-regulation device in response to the identified sleep stage being an REM sleep stage. Examples of room-climate-regulation devices the temperatures of which may be controlled include air-conditioning units (e.g., room-climate-regulation device 170 as shown in FIG. 10, which includes a heater and an air conditioner), electric heaters, radiators, bed coolers, and electric blankets.

In some applications, the control unit is configured, by analyzing the sensor signal, to identify an indication of a body temperature of the subject, and/or ascertain that the subject is uncomfortable with the current ambient temperature. The control unit then controls the temperature setting in response thereto. For example, the control unit may identify a tremor component of the signal, i.e., a component of the signal indicative of shivering of the subject, and in response thereto, raise the temperature setting of the room-climate-regulation device. Alternatively or additionally, the control unit may control a setting (e.g., a temperature setting) of the room-climate-regulation device in response to identifying changes in parameters of the subject from their baseline values. Such parameters include motion of the subject, respiratory rate, respiratory patterns, respiration amplitude, respiration-cycle variability, heart rate, heart rate variability, heartbeat amplitude, pulse transfer time, left ventricular ejection time, and vasoconstriction. In some applications, the control unit controls the temperature setting of the room-climate-regulation device irrespective of the sleep stage of the subject.

In some applications, control unit 28 is adaptive to a particular subject, in that the control unit "learns" from previous responses of the subject to changes in the noise level or temperature setting of the room-climate-regulation device. For example, the control unit may modify the magnitude or timing of the change in response to a previous change not having been fully effective, or in response to a previous change having been disruptive to the subject's sleep.

Figure 12:
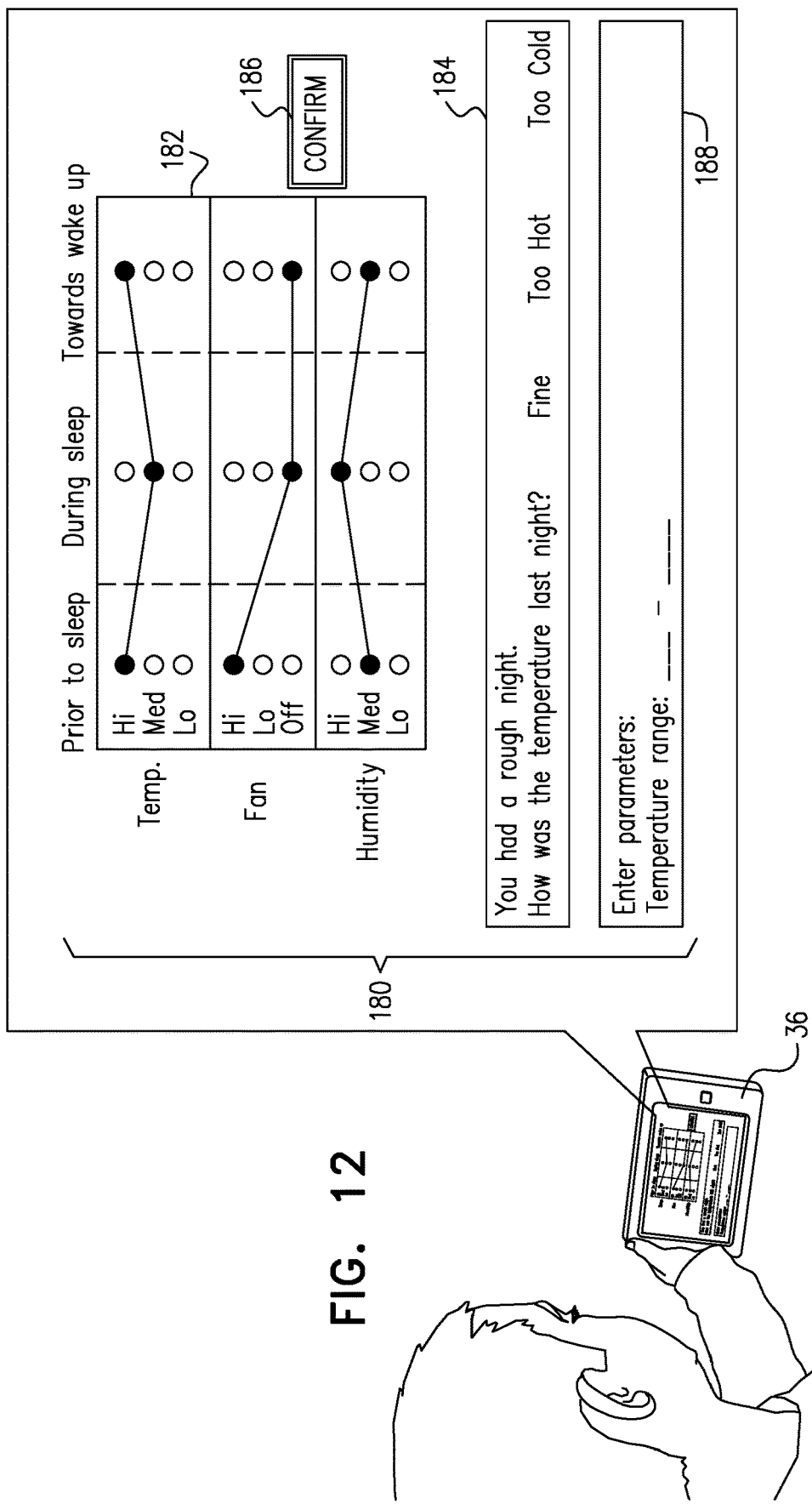
FIG. 12 is a schematic illustration of a user interface, in accordance with some applications of the present invention.

Reference is now additionally made to FIG. 12, which is a schematic illustration of a user interface 180, which is typically for use with a room-climate-regulation device 170

(e.g., as shown in FIG. 10), in accordance with some applications of the present invention. In some applications, user interface 180 (which may be embodied in any one of the user interface devices 35 described with reference to FIG. 1, for example, in smartphone 36 or tablet device 34) is configured to accept an input from the subject that facilitates the control of the room-climate-regulation device. For example, user interface 180 may include a setting-entry interface 182, which allows the subject to input at least two distinct settings for the room-climate-regulation device corresponding to respective different sleep stages, i.e., a "room-climate-control profile". In general, a room-climate-control profile is a function that maps two or more different sleep stages to respective settings of the device. For example, the profile may map a light sleep stage to a first temperature setting, a slow-wave (i.e., deep) sleep stage to a second temperature setting, and an REM sleep stage to a third temperature setting. Alternatively or additionally, the profile may map different "macro stages" of sleep to different settings. Thus, for example, in a wintertime scenario, the profile may indicate that:

(a) As the subject is falling asleep (i.e., is in a falling-asleep stage, prior to sleep), the heat should be set to a high setting.

(b) As the subject begins to sleep (i.e., is in a beginning-sleep stage), the heat should be lowered to a medium setting.

(c) While the subject continues to sleep (i.e., is in a mid-sleep stage), the heat should be lowered to a low setting, or maintained at the medium setting.

(d) As the subject is awakening at a normal time (i.e., is in an awakening stage), and/or is awakening prematurely (i.e., is in a premature-awakening stage), the heat should be raised back to the high setting.

The control unit differentially identifies the relevant sleep stages, and controls the room-climate-regulation device in accordance with the subject's input. For example, upon ascertaining that the subject is in an awakening stage and/or a light sleep stage, rather than a mid-sleep stage and/or a deep sleep stage, the control unit may raise the temperature in the room. In some applications, the control unit also controls another device, such as an alarm clock, in response to the differentially identified sleep stages. For example, upon reaching the subject's desired awakening time, the control unit may wait until the subject is in an awakening stage, and then activate the alarm clock.

In some applications, the control unit drives the user interface to prompt the subject to enter the input, in response to a change in a relevant parameter. For example, in response to a change in season, an ambient temperature, an ambient humidity, and/or a going-to-sleep time (e.g., the subject is going to bed at an unusual time), the control unit may drive the user interface to prompt the subject to re-enter his room-climate preferences. (The control unit may identify the change of the relevant parameter in a variety of ways, such as, for example, by receiving input from a sensor, or by checking the Internet.) In some applications, sensor 22 senses a weight of a blanket of the subject, and the control unit drives the user interface to prompt the subject to enter the input, in response to a change in the sensed weight. For example, the subject may be prompted to enter the input upon the subject switching to a heavy winter blanket.

Aspects of the control of the room-climate-regulation device, as described above, are depicted in FIG. 13, which is a device-control flow chart, in accordance with some applications of the present invention. At a prompting step 190, the subject is prompted to input his room-climate preferences. The input is accepted at an input-accepting step 192. At a device-setting step 194, the room-climate-regulation device is set in response to the input. At a parameter-change-detection step 196, the control unit checks for a change in a relevant parameter, such as an ambient temperature. If the control unit detects a change, the control unit may reset the device (e.g., by communicating a new room-climate-control profile to the device) at device-setting step 194. (Prior to setting the device, the control unit may first prompt the user, at prompting step 190, to confirm that a suggested setting is acceptable, and/or to input relevant parameters.)

Figure 14:
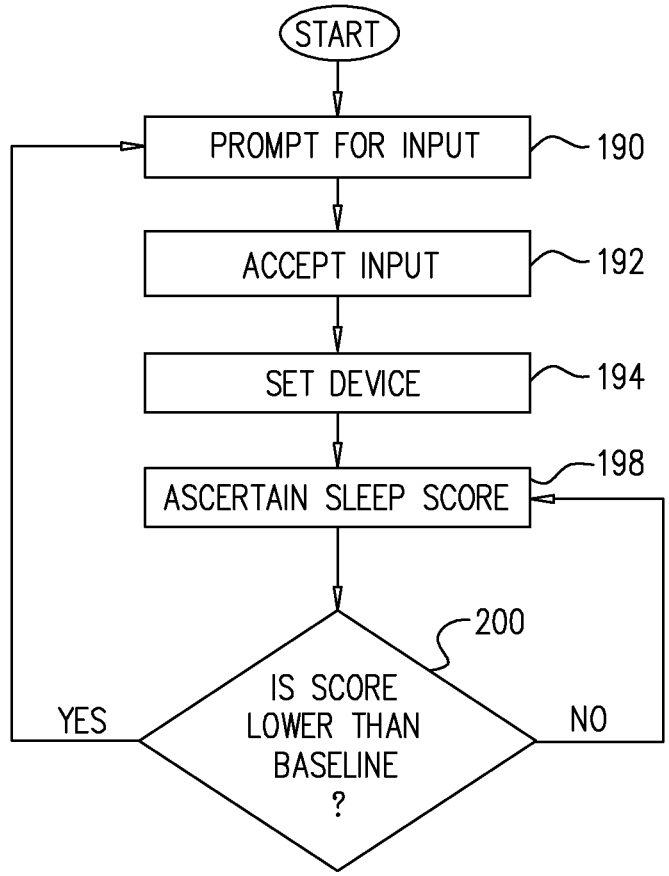

Reference is now made to FIG. 14, which is another device-control flow chart, in accordance with some applications of the present invention. In some applications, at a sleep-score-ascertaining step 198, the control unit ascertains, in response to analyzing the sensor signal, a sleep score of the subject. For example, the control unit may compute a score from one or more parameters such as a time to fall asleep, duration of sleep, or "sleep efficiency," which is the percentage of in-bed time during which the subject is sleeping. For some applications, the score is calculated using one or more of the aforementioned parameters, such that a higher sleep score is indicative of more restful sleeping session relative to a lower sleep score. At a score-comparison step 200, the control unit compares the sleep score to a baseline value, e.g., an average sleep score over a previous period of time. In response to the ascertained sleep score being lower than the baseline value, the control unit may drive the user interface to prompt the subject, at prompting step 190, to re-enter his room-climate preferences, since it is possible that the room climate was a contributing factor in the subject's low sleep score. Alternatively or additionally, at prompting step 190, the control unit may drive user interface 180 (FIG. 12) to prompt the subject to use a factor-entry interface 184 to input at least one factor that may have caused the low sleep score. The control unit then controls the room-climate-regulation device in response to the input.

In some applications, the control unit computes a measure of relaxation, i.e., a relaxation score, for the subject, one or more times during a sleeping session. For example, a high relaxation score may be computed if the subject shows little movement, and little variation in both respiration rate and respiration amplitude. The relaxation score may be used to compute the sleep score. Alternatively or additionally, in response to a low relaxation score, the control unit may immediately adjust the room climate.

In some applications, the control unit controls the room-climate-regulation device in response to the low sleep score, even without any input from the user. For example, if, in the summer, the subject woke up shivering in the middle of the night, the control unit may ascertain that the strength of the air conditioning was not lowered quickly enough. In response thereto, the control unit may adjust the subject's room-climate-control profile, such that, for example, the temperature in the room rises soon after the subject falls asleep. In some applications, in response to the low sleep score, the control unit generates an output (e.g., via user interface 180) that includes a suggested setting for the room-climate-regulation device. For example, with reference to FIG. 12, setting-entry interface 182 may display, at prompting step 190, a suggested room-climate-control profile, which the subject may edit and/or confirm by hitting a confirm button 186.

It is noted that in the context of the claims and description of the present application, the word "setting" has a broad definition, in that it encompasses at least (a) a particular mapping in a room-climate-control profile (e.g., a room-climate-control profile may specify a high temperature "setting" for the falling-asleep stage), and (b) the room-climate-control profile itself. Thus, depending on the particular context, the word "setting" may refer to (a), or (b), or both.

In some applications, in response to a premature awakening of the subject, the control unit is configured to change a setting of the room-climate-regulation device, to facilitate the subject falling asleep again. For example, the control unit may set the room-climate-regulation device to whichever setting helped the subject fall asleep at the beginning of the night.

Figure 15:
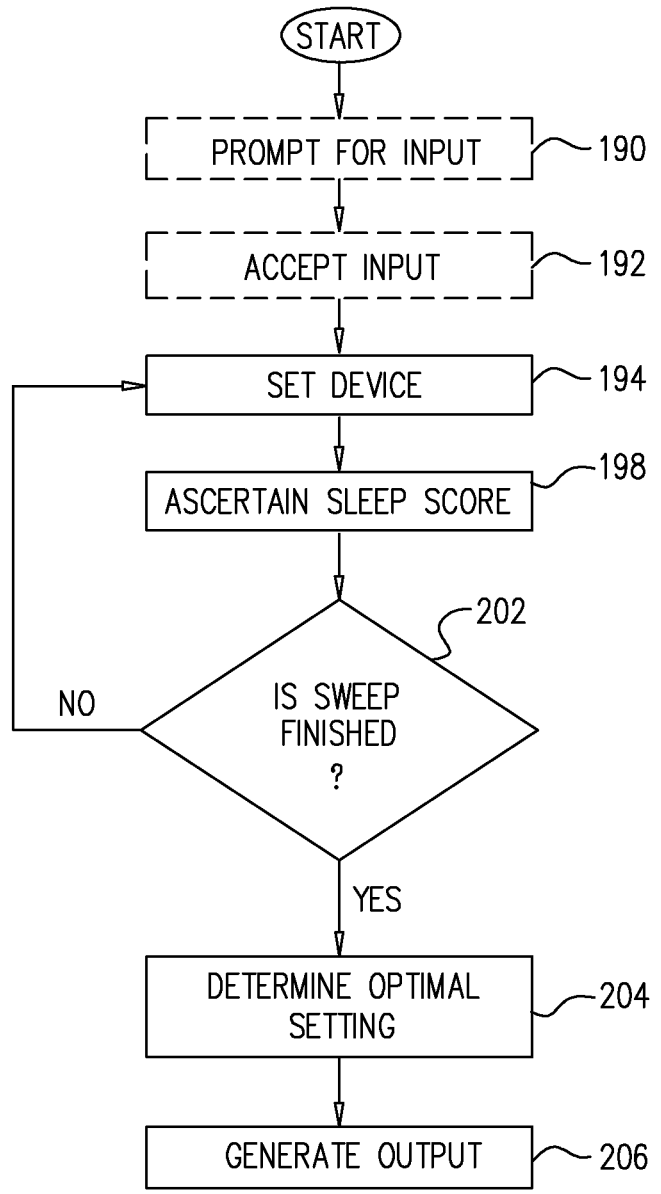
FIG. 15 is a setting-optimization flow chart, in accordance with some applications of the present invention.

Reference is now made to FIG. 15, which is a setting-optimization flow chart, in accordance with some applications of the present invention. In some applications, the control unit is configured to perform a "sweep" (or "optimization routine") over a plurality of different settings (e.g., a plurality of different room-climate-control profiles), in order to ascertain which setting is conducive to a higher sleep score, relative to other settings, e.g., which setting maximizes the sleep score. For example, over the course of several sleeping sessions, the control unit may change the room-climate-control profile in different ways, and in response thereto, determine the optimal room-climate-control profile.

Before each sleeping session, the control unit sets the device at device-setting step 194. After the sleeping session, the control unit ascertains the sleep score, at sleep-score-ascertaining step 198. At an is-sweep-finished-determination step 202, the control unit determines whether more settings should be tried. If the control unit determines that no more settings should be tried (since, for example, a local maximum of the sleep score was attained), the control unit ascertains, at an optimal-setting-determination step 204, which setting maximizes the sleep score, i.e., which setting yields at least a local maximum of the sleep score. At an output-generating step 206, the control unit generates an output indicative of this "optimal" setting. For example, the output may include a control signal to the room-climate-regulation device that drives the device to use the optimal room-climate-control profile on subsequent nights. Alternatively or additionally, the output may include a signal to the user interface to display the optimal room-climate-control profile to the subject, and the subject may then edit and/or approve this profile, as described hereinabove.

In some applications, user interface 180 (FIG. 12) includes a parameter-entry interface 188, which allows the subject to enter a range for one or more parameters. At prompting step 190, the subject is prompted to input this information, and the control unit accepts this input at an input-accepting step 192. The control unit then sets the plurality of different settings in response to the input, i.e., the control unit then performs the sweep over the range. (FIG. 15 indicates (using dashed boxes to indicate optional steps) that prompting step 190 and input-accepting step 192 are optional, since, as described hereinabove, the control unit may set the plurality of different settings even without any deliberate input from the subject.)

Figure 16:
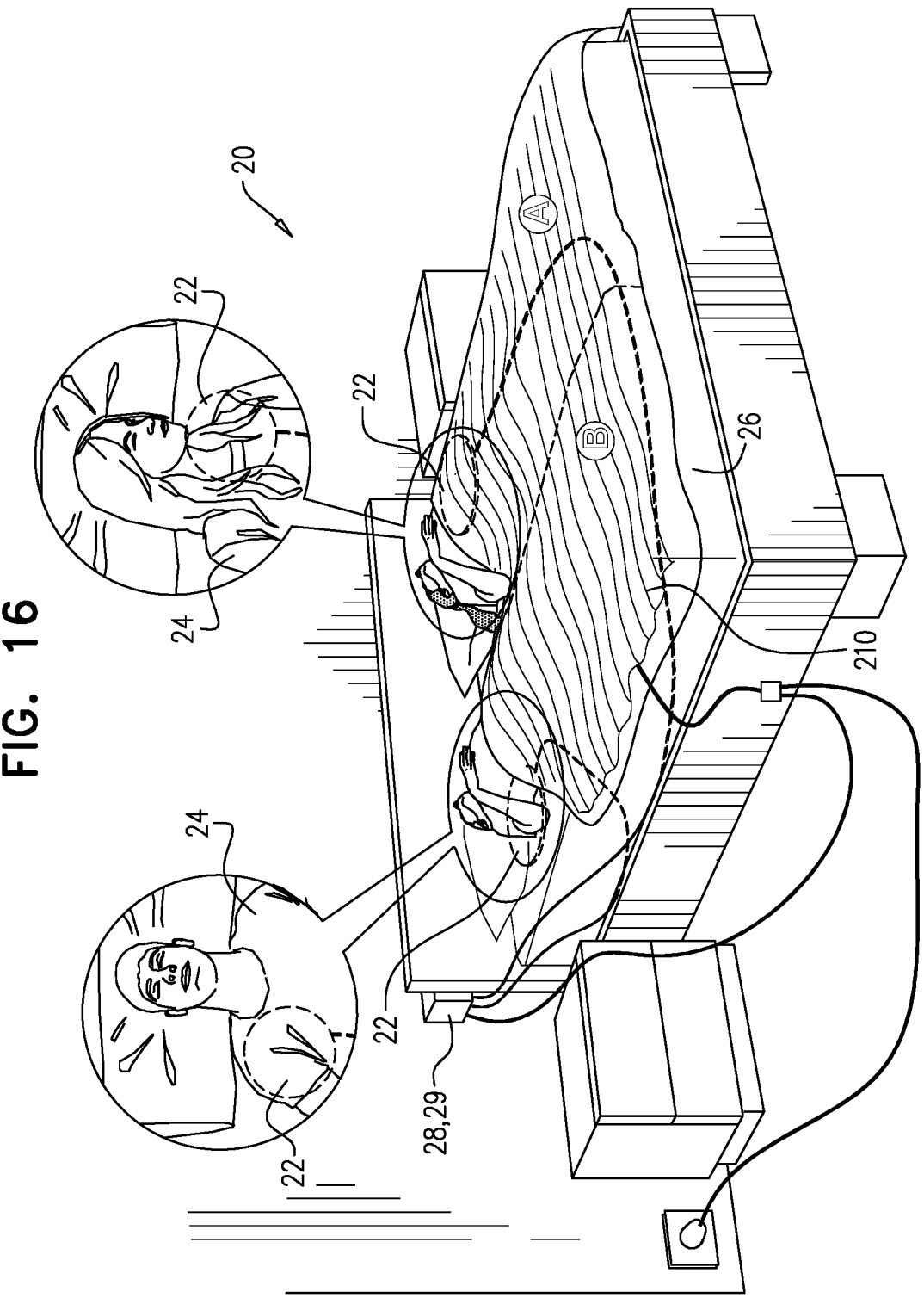
FIG. 16 is a schematic illustration of apparatus for use with two subjects who share a room, in accordance with some applications of the present invention.

Reference is now made to FIG. 16, which is a schematic illustration of subject-monitoring apparatus 20 for use with two subjects who share a room, in accordance with some applications of the present invention. Components of subject-monitoring apparatus 20 are generally similar to those of subject-monitoring apparatus 20 described hereinabove with reference to FIG. 1. Subject-monitoring apparatus 20 comprises one or more sensors 22, which are generally as described hereinabove, and are configured to monitor first and second subjects 24. Subject-monitoring apparatus 20 includes a control unit, which is typically a computer processor, such as computer processor 28 described hereinabove. As described hereinabove, computer processor typically communicates with a memory 29. The computer processor is typically a control unit that performs the algorithms described herein, including analyzing the signal from sensor 22.

In general, if two room-sharing subjects have different room-climate preferences, and/or are in different stages of sleep, managing the room climate may be challenging. As described hereinbelow, applications of the present invention address this challenge.

Figure 13:
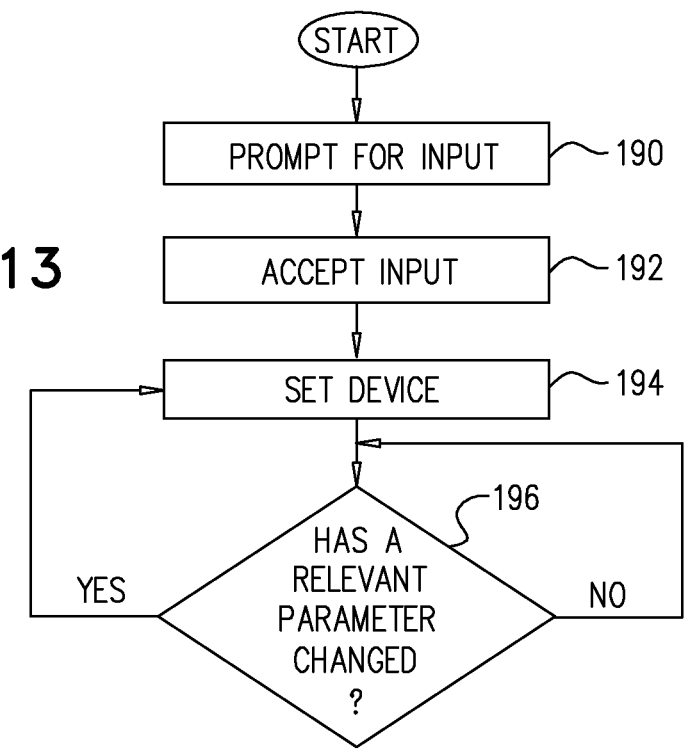
FIGS. 13-14 are device-control flow charts, in accordance with some applications of the present invention.

As shown in FIG. 16, apparatus 20 typically comprises first and second sensors 22 configured to monitor respective subjects. (In some applications, a single sensor 22 monitors both subjects.) The control unit analyzes the sensor signals, identifies the respective sleep stages of the subjects, and in response to the respective identified sleep stages, controls a room-climate-regulation device by sending a control signal to the room-climate-regulation device. FIG. 13 illustrates this for a room-climate-regulation device that includes an electric blanket 210. For some applications, the room-climate-regulation device includes an air-conditioner and/or a heater, as shown in FIG. 10, for example.

In some applications, the room-climate-regulation device can simultaneously maintain a first setting in a vicinity of the first subject, and a second setting, which is different from the first setting, in a vicinity of the second subject. For example, electric blanket 210 may be able to simultaneously maintain a first temperature in area A, and a second temperature in area B. The control unit communicates the first and second settings (e.g., the first and second temperatures) to the room-climate-regulation device, in response to the respective identified sleep stages, and/or in response to other detected physiological activity of the subjects. In some applications, the control unit also ascertains a sleep score for each of the subjects, and controls the room-climate-regulation device in response to the sleep scores, e.g., as described hereinabove.

In some cases, the room-climate-regulation device can maintain only a single setting. In such cases, the control unit may determine a "compromise" setting that is at least somewhat acceptable to each of the subjects. A compromise setting may be determined in response to an average sleep score of the subjects. For example, the control unit may determine a setting of the room-climate-regulation device that maximizes the average sleep score of the subjects (e.g., a setting that minimizes the average falling-asleep time). Alternatively, the compromise setting may be a setting of the room-climate-regulation device that facilitates respective sleep scores of the subjects being equal to one another. If both subjects are trying to fall asleep, the control unit may communicate the compromise setting, such as to give each subject a "fair chance" of falling asleep. Upon one of the subjects falling asleep, the control unit may communicate a second, different setting that is at least somewhat more sleep-conducive for the subject who is still awake, relative to the first setting.

Alternatively, in response to one of the sensor signals indicating that one of the subjects is trying to fall asleep, the control unit may first communicate a setting that is at least somewhat more sleep-conducive for that subject, relative to the other subject, to help that subject fall asleep. Subsequently, in response to the sensor signals indicating that (a) the subject has fallen asleep, and (b) the other subject is trying to fall asleep, the control unit may communicate a second setting to the room-climate-regulation device, the second setting being at least somewhat more sleep-conducive for the other subject, relative to the first setting, to help the other subject fall asleep. Once both subjects are asleep, the control unit may communicate a compromise setting to the room-climate-regulation device, as described hereinabove.

In some applications, the control unit makes gradual changes to the settings. For example, if Subject A prefers a temperature of 23 C, and Subject B prefers 25 C, the control unit may first communicate a setting of 23 C, to help Subject A fall asleep. Subsequent to Subject A falling asleep, the control unit may change the setting to 24 C. If Subject B does not fall asleep within a reasonable amount of time, the temperature may then be changed to 25 C. By not immediately changing the temperature to 25 C subsequent to Subject A falling asleep, the control unit may help prevent Subject A from waking up prematurely.

In some cases, e.g., cases in which the subjects' room-climate preferences for falling asleep are very different from one another, one of the subjects may wish to wait outside the room until the other subject is asleep. In such applications, the control unit may generate an output (e.g., a text message) to the waiting subject, the output indicating that the subject's partner has fallen asleep. Then, the room-climate setting may be adjusted, to help the still-awake subject fall asleep.

Figure 17:
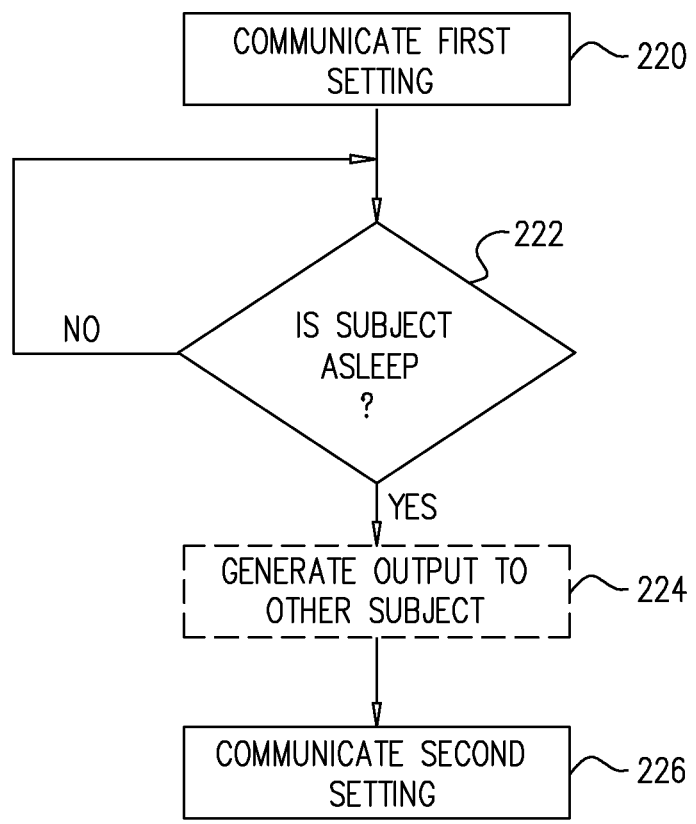
FIG. 17 shows a flow chart depicting aspects of the functioning of apparatus for use with room-sharing subjects, in accordance with some applications of the present invention.

Reference is now made to FIG. 17, which shows a flow chart that depicts aspects of the functioning of apparatus 20 with room-sharing subjects, as described above, in accordance with some applications of the present invention. At a first communicating step 220, the control unit communicates a first setting to the room-climate-regulation device. The first setting may be, for example, a compromise setting, or a setting that is more conducive to sleep of a particular one of the subjects. At a sleep-assessment step 222, the control unit assesses whether one of the subjects is asleep. If one of the subjects is asleep, the control unit, optionally, generates an output to the other subject, at an output-generation step 224. Finally, at a second communication step 226, the control unit communicates a second setting to the room-climate-regulation device, the second setting being more conducive to sleep of the still-awake subject, relative to the first setting.

Reference is again made to FIG. 10. For situations in which two or more subjects share a common area (e.g., a common sleeping area, as described hereinabove, or a common living room), the control unit may control a controllable mechanism (e.g., room-climate-regulation device 170, or an illumination device) in response to determining which of the subjects are present in the common area. At least one sensor 22 monitors the common area and generates a sensor signal in response thereto. In response to analyzing the sensor signal, the control unit determines which of the plurality of subjects are present in the common area, and controls the controllable mechanism in response thereto.

For example, for two subjects who share a room, room-climate-regulation device 170 may have three distinct settings, corresponding respectively to (a) a situation in which the first subject, but not the second subject, is present, (b) a situation in which the second subject, but not the first subject, is present, and (c) a situation in which both subjects are present. For example, the first and second settings may be, respectively, the first subject and second subject's "optimal" temperatures for falling asleep, the third setting being an intermediate ("compromise") setting between the first and second settings. The control unit then sets the room-climate-regulation device to the appropriate setting, in response to determining which of the subjects is present. In some applications, the control unit establishes the three distinct settings, in response to analyzing the sensor signal. For example, the control unit may use machine-learning techniques to establish the respective "optimal" settings for scenarios (a)-(c) described above. Alternatively or additionally, the control unit may establish the settings via any of the techniques described hereinabove with reference to FIGS. 12-15, mutatis mutandis.

Figure 18:
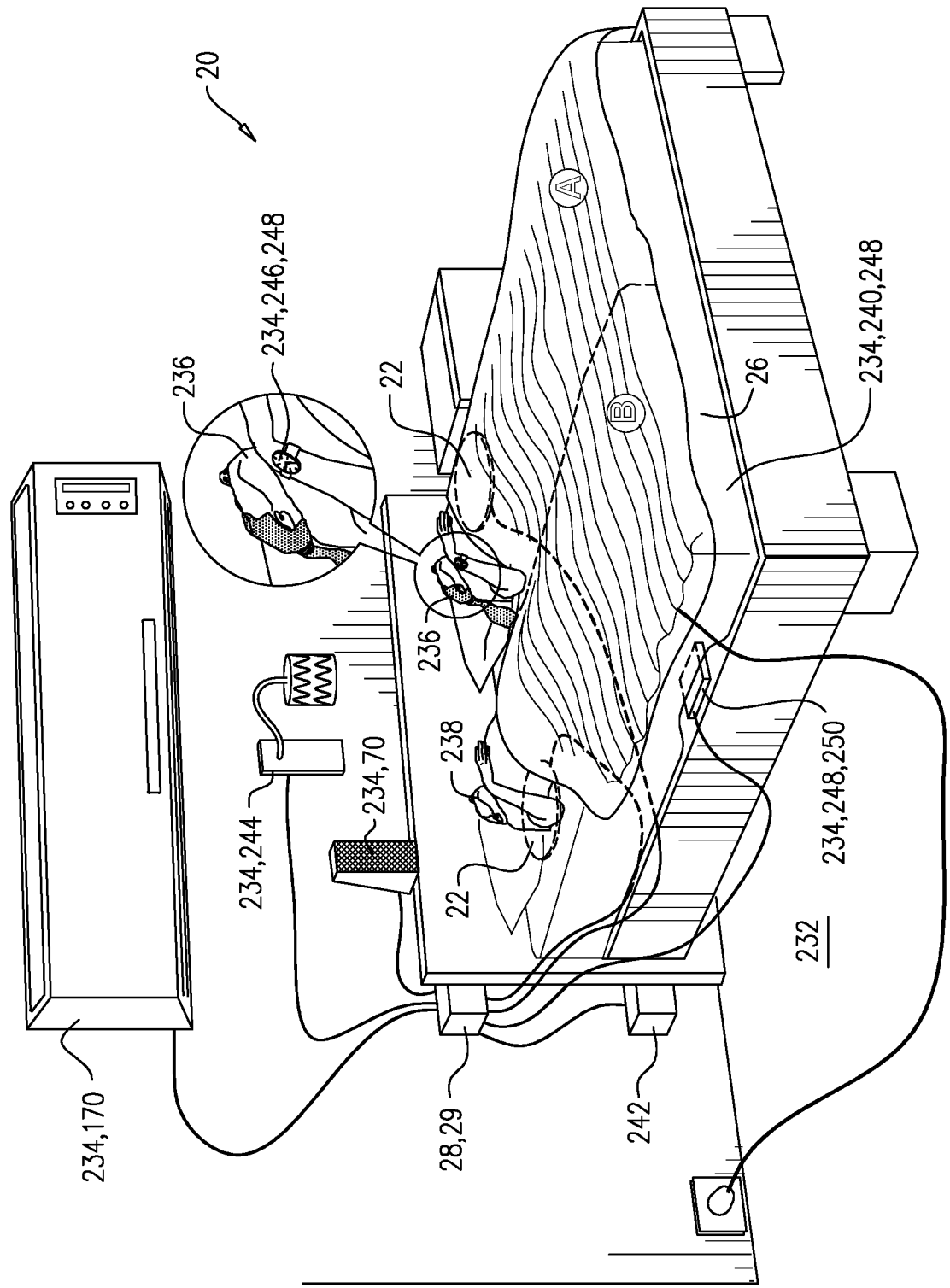
FIG. 18 is a schematic illustration of apparatus for use with (i) a plurality of subjects sharing a common area, and (ii) a controllable mechanism, in accordance with some applications of the present invention.

Reference is now made to FIG. 18, which is a schematic illustration of subject-monitoring apparatus 20 for use with (i) a plurality of subjects sharing a common area 232, and (ii) a controllable mechanism 234, e.g., room-climate-regulation device 170, in accordance with some applications of the present invention. Components of subject-monitoring apparatus 20 are as described hereinabove with reference to FIG. 1. Subject-monitoring apparatus 20 comprises one or more sensors 22, which are generally as described hereinabove, and are configured to monitor subjects 236 and 238 (subjects 236 and 238 corresponding to subject 24 of FIG. 1). Subject-monitoring apparatus 20 includes a control unit, which is typically a computer processor, such as computer processor 28 described hereinabove. As described hereinabove, computer processor typically communicates with a memory 29. The computer processor is typically a control unit that performs the algorithms described herein, including analyzing the signal from sensor 22.

Apparatus 20 comprises one or more physiological sensors 22, which are configured to monitor conditions of the subjects and to generate, in response thereto, a respective sensor signal for each one of the subjects. Control unit 28 analyzes the sensor signals, and, in response thereto, determines a prioritization of the condition of one of the subjects over the condition of another one of the subjects. In response to the prioritization, the control unit decides whether to control controllable mechanism 234. Subsequently, in response to (i) the prioritization, and (ii) deciding to control the controllable mechanism, the control unit controls the controllable mechanism by communicating a control signal to the controllable mechanism.

In general, the concept of "prioritizing a condition," as used in the claims and description of the present application, should be understood to include at least the idea of "trading off" potentially conflicting needs and/or preferences of the plurality of subjects. For example, at times the condition of Subject A (which may be either one of subjects 236 and 238) is more pressing than that of Subject B (which is the other one of subjects 236 and 238), such that Subject B may have to suffer for the sake of Subject A. Thus, for example, the control unit may control the controllable mechanism for the benefit of Subject A, even to the detriment of Subject B.

For example, as shown in FIG. 18, common area 232 may be a common sleeping area, and the "condition" that is monitored may be sleep, i.e., sensors 22 may monitor sleep of the subjects, e.g., by monitoring heart rate, respiratory rate, and/or large body movement. In response to analyzing the sensor signals, the control unit may determine a prioritization of sleep of one of the subjects over sleep of another one of the subjects. For example, in response to analyzing the sensor signals, the control unit may determine that a first subject 236 is sleeping, while a second subject 238 is not sleeping. (For example, the control unit may determine that subject 236 has been sleeping for a significant amount of time, while subject 238 has been unable to fall asleep for a significant amount of time.) In response thereto, the control unit may determine that the sleep of subject 238 should be prioritized over that of subject 236, in order to be "fair" to subject 238. Consequently, the control unit may decide to change the temperature of the room to a new temperature that is more conducive to the sleep of subject 238. For example, if the current temperature is 20 C, the control unit may raise the temperature to 23 C if this is the "optimal" temperature for subject 238, even if 23 C is not the "optimal" temperature for subject 236, and even if 23 C is detrimental to the sleep of subject 236. For example, even if it is likely that subject 236 will awaken as a result of the temperature change, the control unit may in any case make the change.

In general, apparatus 20 as shown in FIG. 18 may be used in combination with techniques described hereinabove with reference to FIGS. 12-17. For example, each of the room-sharing subjects may have a room-climate-control profile (as described with reference to FIGS. 12-17). The control unit may then switch between the respective profiles at various times during the night, depending on which subject is currently prioritized over the other subject(s).

In some applications, the "condition" is comfort, i.e., sensors 22 monitor comfort of the subjects, and the control unit prioritizes the comfort of one subject over the comfort of another subject. For example, in response to the sensor signals indicating that one of the subjects is shivering, the control unit may prioritize the comfort of the shivering subject, and subsequently raise the temperature in the room, even if another subject is more comfortable with the current temperature than with the new, higher temperature. In such applications, common area 232 may be a common sleeping area, or may be a different type of common area, e.g., a living room. (For example, sensors 22 may be worn on the bodies of the subjects and/or placed inside sofas or recliners in the living room.)

In some applications, controllable mechanism 234 is an adjustable resting surface 240 (e.g., a shared adjustable resting surface), the control unit controlling adjustable resting surface 240 in response to the prioritization of the condition (e.g., sleep and/or comfort) of one of the subjects. (FIG. 18 shows the control unit in communication with a parameter-adjusting unit 242 of the resting surface.) For example, the control unit may set the resting surface to a particular angle in order to facilitate the sleep and/or comfort of subject 238, even if subject 236 prefers a different angle, and even if the particular angle is detrimental to the sleep and/or comfort of subject 236. In this context, apparatus 20 may be used in combination with techniques described hereinbelow with reference to FIG. 24. For example, in response to detecting that the current posture of subject 238 is conducive to apnea, the angle of the resting surface may be changed, even to the detriment of the sleep of subject 236.

In some applications, controllable mechanism 234 is an illumination device 244 (e.g., a lamp, as shown), the control unit controlling illumination device 244 in response to the prioritization. For example, the control unit may darken or lighten the room to a particular illumination level in order to facilitate the sleep and/or comfort of subject 238, even if subject 236 prefers a different illumination level, and even if the particular illumination level is detrimental to the sleep and/or comfort of subject 236. In this context, apparatus 20 may be used in combination with techniques described in WO 2015/008285 to Shinar (e.g., techniques described with reference to FIGS. 19 and 20 of the aforementioned PCT to Shinar), which is incorporated herein by reference.

In some applications, controllable mechanism 234 is a sound-playing device (e.g., speaker 70, described hereinabove), the control unit being configured to control the sound-playing device in response to the prioritization. For example, the control unit may adjust speaker 70 to a particular volume in order to facilitate the sleep and/or comfort of subject 238, even if subject 236 prefers a different volume, and even if the particular volume is detrimental to the sleep and/or comfort of subject 236.

In some applications, the control unit is configured to determine the prioritization in response to a health condition of at least one of the subjects. For example, in response to analyzing the sensor signals, the control unit may determine that subject 236 is experiencing an asthma attack, and/or has experienced asthma attacks in the past. In response, the control unit may prioritize the sleep and/or comfort of subject 236, and consequently, drive room-climate-regulation device 170 to blow cold air into the room, even if the cold air is disruptive to the sleep and/or comfort of subject 238. In some applications, apparatus 20 comprises at least one body-temperature sensor (e.g., integrated with a wristwatch 246) configured to (i) detect a body temperature of at least one of the subjects, and (ii) generate a body-temperature signal in response thereto, the control unit being configured to determine the health condition of the subject(s) in response to the body-temperature signal(s).

In some applications, user interface device 35 (described hereinabove with reference to FIG. 1) is configured to accept an input from a user, and the control unit is configured to determine the prioritization further in response to the input. For example, before going to sleep, subject 238 may input an indication that she is feeling unusually tired. In response, the control unit may prioritize the sleep of subject 238 over that of subject 236, and control the controllable mechanism accordingly. Alternatively or additionally, the input may indicate that subject 238 is currently ill, or is recovering from a recent illness. (Such indication may also be received from the sensor signals, alternatively or additionally to the user input.) In response, the control unit may prioritize the sleep and/or comfort of subject 238 over that of subject 236, and control the controllable mechanism accordingly.

In some cases, controlling the controllable mechanism in a particular manner is (i) facilitative to sleep of a first subject, but (ii) at least potentially detrimental to sleep of a second subject; in such cases, the control unit decides to control the controllable mechanism in the particular manner only if the prioritization indicates that sleep of the first subject is to be prioritized over sleep of the second subject. (In the context of the claims and description of the present application, "at least potentially detrimental" means there is at least a small (but non-negligible) likelihood that the sleep of the second subject will be disturbed.) For example, as noted above, a change in the room temperature may facilitate the sleep of one subject, but potentially disrupt the sleep of another subject. Other examples include cases in which one of the subjects is snoring. In such cases, as further described immediately hereinbelow, the control unit may activate a snoring-inhibition mechanism 248 that is disruptive to sleep of the snoring subject, in order to inhibit the snoring, and thus help another subject sleep.

For some applications, in response to analyzing the sensor signals, the control unit determines that (i) one of the subjects is snoring, and (ii) another one of the subjects may be disturbed by the snoring. (The snoring may be identified, for example, using techniques described in US 2007/0118054 to Pinhas, now abandoned, which is incorporated herein by reference.) In response thereto, the control unit decides to activate snoring-inhibition mechanism 248, unless the prioritization indicates that sleep of the snoring subject is to be prioritized over sleep of the other one of the subjects. An example of snoring-inhibition mechanism 248 is a vibrating mechanism 250, which, by vibrating, disrupts the sleep of the snoring subject and/or "nudges" the snoring subject to change position, thus inhibiting future snoring. For example, a vibrating mechanism 250 may be disposed underneath the mattress, and/or wristwatch 246 may be configured to vibrate. Another example of snoring-inhibition mechanism 248 is adjustable resting surface 240 (e.g., an adjustable mattress or pillow), which, by being adjusted, disrupts the sleep of the snoring subject and/or moves the subject to a different position in which snoring is less likely to occur. (The snoring-inhibition techniques described here may be practiced in combination with posture detection, as described hereinbelow with reference to FIG. 24.)

Typically, the control unit identifies respective sleep stages of the subjects by analyzing the sensor signals, and determines the prioritization in response to identifying the respective sleep stages. For example, the control unit may identify that each of the respective sleep stages is a slow-wave (i.e., deep) sleep stage, a rapid-eye-movement (REM) sleep stage, a light sleep stage, or an awake sleep stage. (In the context of the claims and description of the present application, a subject who is awake is considered to be in an "awake sleep stage.") The control unit further assigns a rank to each sleep stage, where slow-wave sleep and REM sleep have the two lowest rankings, light sleep has the next-highest ranking, and awake has the highest ranking. (Slow-wave sleep may be ranked higher or lower than REM sleep.) The likelihood of the control unit prioritizing the sleep of a first subject over the sleep of a second subject generally increases or decreases with the rank of the first subject's sleep stage. For example, Table 1 below shows an illustrative example of a manner in which the control unit may determine whether to activate snoring-inhibition mechanism 248, in response to the respective sleep stages of the subjects. (Similar tables may be constructed to show how the control unit might prioritize the sleep of the subjects in other contexts, e.g., for adjusting the lighting or temperature in the room, mutatis mutandis.)

TABLE 1

| Sleep Stage of Snoring Subject | Sleep Stage of Other Subject | | | |
|---|---|---|---|---|
| | Slow-wave | REM | Light | Awake |
| Slow-wave | Don't Activate | Don't Activate | Don't Activate | Activate |
| REM | Don't Activate | Don't Activate | Activate | Activate |
| Light | Don't Activate | Activate | Activate | Activate |

As illustrated in Table 1, as the rank of the sleep stage of the snoring subject decreases, the sleep of the snoring subject is more likely to be prioritized over the sleep of the other subject. One reason for this is that the quality, e.g., the benefits, of slow-wave and REM sleep is greater than that of light sleep. Thus, for example, the snoring subject suffers less if he is awakened from light sleep than if he is awakened from REM or deep sleep. On the other hand, as the rank of the sleep stage of the other subject decreases, the sleep of the other subject is less likely to be prioritized over the sleep of the snoring subject. One reason for this is that the snoring is less likely to disturb the other subject if the other subject is in a relatively deeper stage of sleep, than if the other subject is in a relatively lighter stage of sleep.

In some applications, the control unit analyzes the sensor signals over a plurality of sleeping sessions, and identifies, for each of the subjects, a sleep-sensitivity of the subject to at least one phenomenon that is generally detrimental to sleep (e.g., a noise or lighting disturbance). For example, the control unit may analyze the duration and/or quality of sleep of the subjects in response to various noise disturbances over the plurality of sleeping sessions. If, for example, subject 238 is seen to be woken more than subject 236, and/or is seen to fall asleep after the disturbances less quickly than subject 236, and/or is seen to have a greater reduction in sleep quality than subject 236 as a result of the noise, the control unit may determine that subject 238 has a greater sleep-sensitivity than subject 236. The control unit then determines the prioritization in response to the identified sleep-sensitivities. Typically, the control unit is more likely to prioritize the sleep of a first subject over the sleep of a second subject if the sleep-sensitivity of the first subject is higher than the sleep-sensitivity of the second subject. For example, Table 2 below is an illustrative modification of Table 1 that shows, by way of example, how the control unit might "tweak" the prioritization in response to the non-snoring ("other") subject having a greater sleep-sensitivity than the snoring subject. (The asterisked entries are those that differ from Table 1.)

TABLE 2

| Sleep Stage of Snoring Subject | Sleep Stage of Other Subject | | | |
|---|---|---|---|---|
| | Slow-wave | REM | Light | Awake |
| Slow-wave | Don't Activate | Don't Activate | Activate (*) | Activate |
| REM | Don't Activate | Activate (*) | Activate | Activate |
| Light | Activate (*) | Activate | Activate | Activate |

In some applications, the control unit is configured to take into account the duration and/or quality of sleep of the subjects during a preceding interval, e.g., during the night thus far, and/or during the previous night or last several nights. In some applications, the duration and/or quality of sleep may be the basis of a sleep score, which the control unit calculates at a particular time in response to analyzing the sensor signals. The control unit then determines the prioritization in response to the respective sleep scores. For example, if the snoring subject has slept well prior to the particular time, while the other subject has not slept well, the sleep score of the snoring subject will be adjusted, for example, such that the sleep score of the snoring subject becomes higher than that of the other subject. The control unit may then be more likely to prioritize sleep of the other subject over sleep of the snoring subject, relative to if the sleep score of the snoring subject were not higher than the sleep score of the other subject. (For example, if the snoring subject has a higher sleep score than the other subject, the control unit may use Table 2, rather than Table 1, in deciding whether to activate the snoring-inhibition mechanism.)

In some cases, as noted above, controlling the controllable mechanism in a particular manner is (i) facilitative to sleep of a first subject, and (ii) at least potentially detrimental to sleep of a second subject. For example, if subject 238 is having difficulty falling asleep, turning on relaxing music may facilitate the sleep of subject 238, but may possibly wake subject 236. Alternatively, if subject 236 is snoring, activating the snoring-inhibition mechanism may facilitate the sleep of subject 238, but will likely disrupt the sleep of subject 236. In such cases, in some applications, the control unit is configured to control the controllable mechanism in the particular manner only if the second one of the subjects is not sleeping deeply. Thus, in the examples provided immediately above, subject 236 is "spared" if he is sleeping deeply.

Also in such cases, the control unit may compare the sleep score of the first subject to a threshold, and control the controllable mechanism in the particular manner in response to the sleep score being lower than the threshold. For example, if, at a time close to morning, subject 238 has not yet slept for six hours, the control unit may be more likely to inhibit the snoring of subject 236, relative to if subject 238 were to have already slept for six hours. The decision is typically also based on the respective sleep stages of the subjects; for example, in response to the sleep score of subject 238 being lower than the threshold, the control unit may decide to inhibit the snoring of subject 236, but only if subject 238 and/or subject 236 is not sleeping deeply. Similarly, the sleep score of the second subject may be compared to a threshold. For example, if subject 236 has already slept for eight hours, the snoring of subject 236 may be inhibited whenever the snoring is potentially disturbing to subject 238.

Table 3 below is another illustrative and non-limiting "decision table," corresponding to a case in which the sleep score of the other (non-snoring) subject is less than a threshold, as described hereinabove. (The asterisked entries are those that differ from Table 1.)

TABLE 3

| Sleep Stage of Snoring | Sleep Stage of Other Subject | | | |
|---|---|---|---|---|
| Subject | Slow-wave | REM | Light | Awake |
| Slow-wave | Don't Activate | Activate (*) | Activate (*) | Activate |
| REM | Don't Activate | Activate (*) | Activate | Activate |
| Light | Don't Activate | Activate | Activate | Activate |

Figure 19:
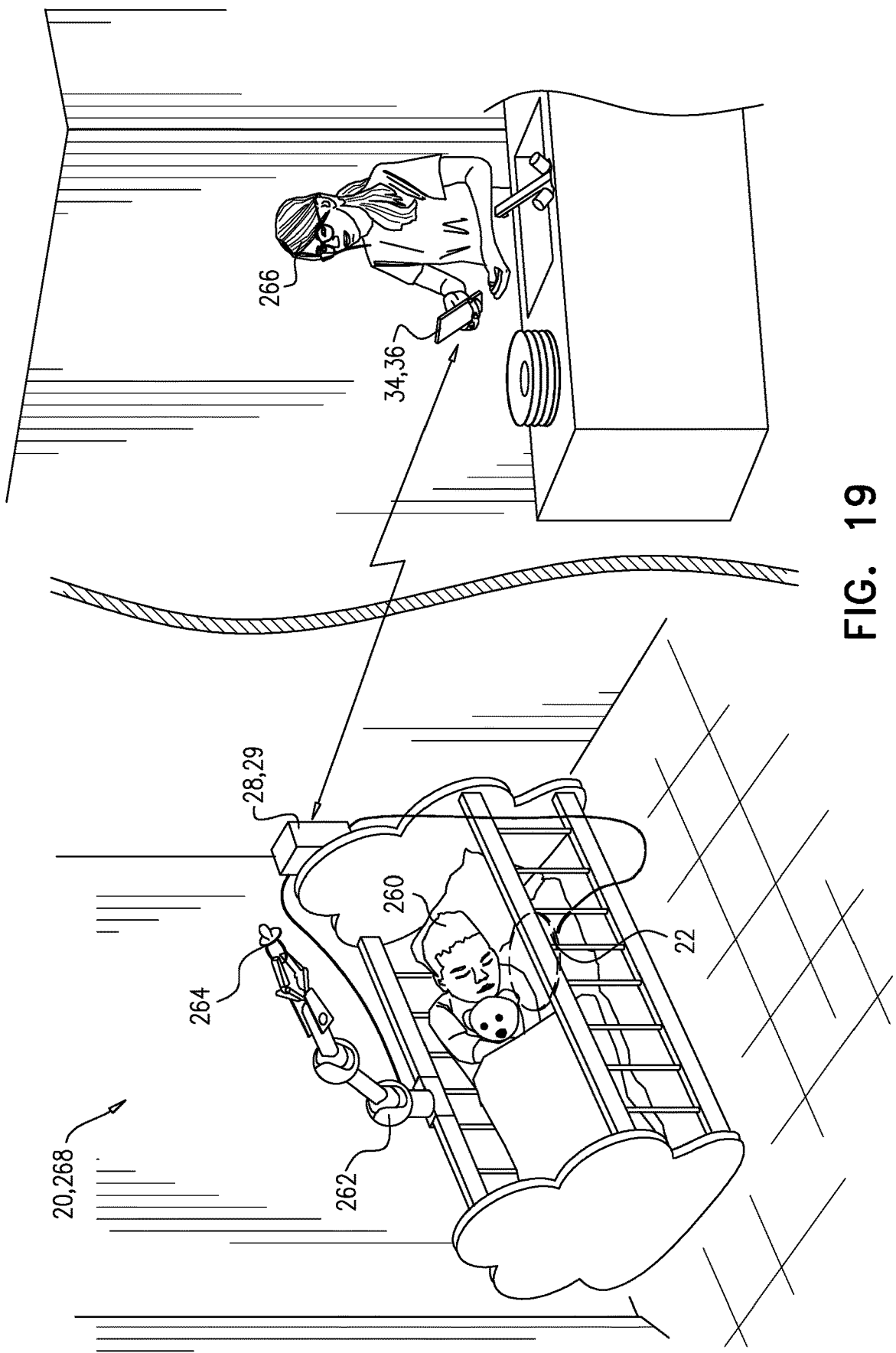
FIG. 19 is a schematic illustration of apparatus for monitoring sleep of a baby, in accordance with some applications of the present invention.

Reference is now made to FIG. 19, which is a schematic illustration of subject-monitoring apparatus 20 for monitoring sleep of a baby 260, in accordance with some applications of the present invention. Components of subject-monitoring apparatus 20 are as described hereinabove with reference to FIG. 1. Subject-monitoring apparatus 20 comprises a sensor 22, which is generally as described hereinabove, and is configured to monitor baby 260 (the baby corresponding to subject 24 of FIG. 1). Subject-monitoring apparatus 20 includes a control unit, which is typically a computer processor, such as computer processor 28 described hereinabove. As described hereinabove, computer processor typically communicates with a memory 29. The computer processor is typically a control unit that performs the algorithms described herein, including analyzing the signal from sensor 22.

For the applications shown in FIG. 19, sensor 22 monitors sleep of baby 260. Control unit 28 is configured to analyze the signal from the sensor, and in response thereto, ascertain that the baby is in a light-sleep stage, and is therefore likely to wake up soon (and possibly disturb other household members who are sleeping). In response to this ascertaining, control unit 28 drives an electromechanical (e.g., a robotic) arm 262 to deliver a comfort-inducing object 264 (e.g., a pacifier or a stuffed animal) to the baby.

Alternatively or additionally, the control unit drives electromechanical arm 262 to deliver comfort-inducing object 264 to the baby, in response to ascertaining that the baby's mouth is performing a sucking motion. Typically, the frequency of a baby's sucking motion is different from that of the baby's heart rate and respiratory rate. Hence, if the control unit detects three dominant frequencies in the sensor signal, and particularly if one of those frequencies is a typical sucking frequency (such as a frequency in the range of 1-2 Hz), the control unit may ascertain that the baby's mouth is performing a sucking motion.

Alternatively or additionally to controlling electromechanical arm 262, the control unit may generate an alert, in response to the baby being in a light sleep, and/or in response to the sucking motion. For example, the control unit may alert a parent 266 of the baby that the baby is in need of food or comfort. Such an alert may improve the quality of care that is provided to the baby, and/or may help reduce the likelihood of the baby waking other members of the household.

FIG. 19 also depicts a method 268 for reducing disturbance to sleep of a subject, in accordance with some applications of the present invention. A typical scenario is depicted in FIG. 4. Baby 260 is sleeping or is in the process of falling asleep in a room. A person (e.g., parent 266) desires to perform an activity that is potentially disturbing to the sleep of the baby; for example, the person may wish to enter the room or turn on a vacuum cleaner. Control unit 28 accepts an input indicative of the person desiring to perform the activity. The control unit analyzes the sensor signal, and, in response to analyzing the signal, identifies a time during which the activity is likely to be less disturbing to the sleep of the subject, relative to another time. For example, the control unit may ascertain that the subject is presently sleeping deeply, or will be sleeping deeply within a given number of minutes. (To identify that the subject is presently sleeping deeply, or will be sleeping deeply within a given number of minutes, the control unit may ascertain the sleep stage of the subject as described, for example, in the above quoted paragraphs [0073], [0181], and [0185]-[0187] from US 2007/0118054 to Pinhas.) The control unit then generates a notification indicating a suitability of performing the activity at the identified time. For example, the control unit may notify the parent that it is now "safe" to enter the room, or that it will be "safe" within a given number of minutes. In some applications, the control unit identifies a window of time for performing the activity.

Method 268 may be implemented via an application, running upon smartphone 36 and/or a tablet device 34 (as shown in FIG. 1), and/or a different one of the user interface devices 35. The person indicates, via smartphone 36 or tablet device 34, that (s)he desires to perform the potentially sleep-disturbing activity. This indication is wirelessly communicated from smartphone 36 or tablet device 34 to control unit 28. Upon identifying the opportune time for performing the activity, the control unit wirelessly communicates the notification (e.g., in the form of a text message) to the smartphone or tablet device.

Figure 20:
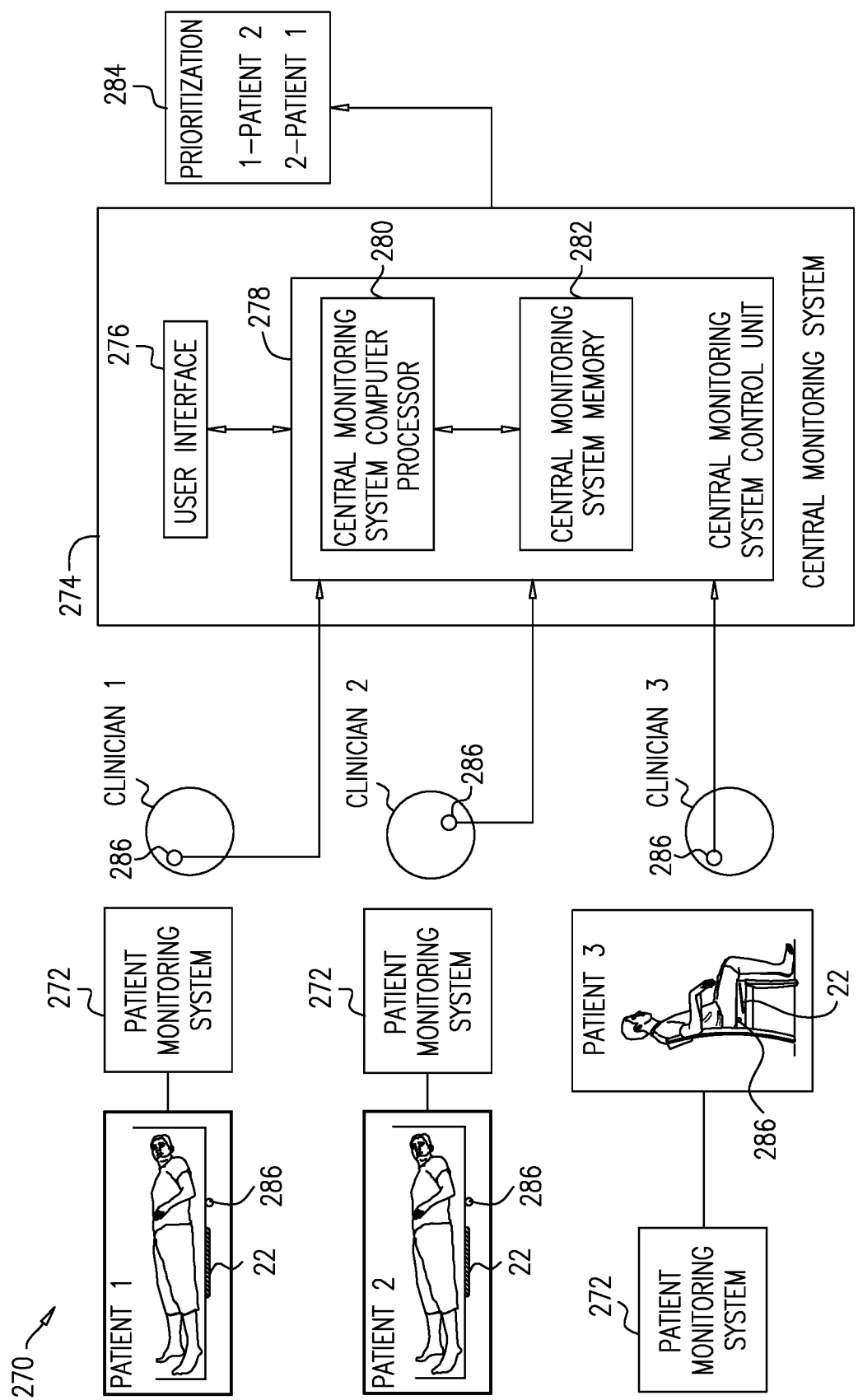
FIG. 20 is a schematic illustration of apparatus for use with a plurality of patients requiring respective care-provision tasks, in accordance with some applications of the present invention.

Reference is now made to FIG. 20, which is a schematic illustration of apparatus 270 for use with a plurality of patients requiring respective care-provision tasks, in accordance with some applications of the present invention. FIG. 20 depicts a typical hospital setting, in which a plurality of subject monitoring systems 272 are in communication with a central monitoring system 274. (This setting is described in detail in US 2013/0267791 to Halperin, which is incorporated herein by reference.) For example, there may be a monitoring system 272 associated with each of the beds and/or chairs in a ward, each of the monitoring systems being in communication with a central monitoring system that is near the nurses' station. Components of subject monitoring systems 272 are generally similar to those of subject-monitoring apparatus 20 described hereinabove with reference to FIGS. 1-5, apart from the differences described hereinbelow. Each monitoring system includes a control unit 28 in communication with a sensor 22, the sensor typically being as described hereinabove. The control unit is typically a computer processor, such as computer processor 28 described hereinabove. As described hereinabove, computer processor typically communicates with a memory 29. The computer processor is typically a control unit that performs the algorithms described herein, including analyzing the signal from sensor 22.

Typically, central monitoring system 274 includes a central monitoring user interface device 276 (e.g., a display, and/or any of the devices described as user interface devices with reference to FIG. 1), and a central monitoring system control unit 278, which typically includes a central monitoring system computer processor 280, which communicates with a memory 282). The display typically displays data relating to a plurality of the patients the monitoring systems of whom are associated with the central monitoring system. For some applications, sensors 22 of the individual subject monitoring systems communicate directly with the central monitoring system control unit. Alternatively or additionally, control units 28 of the individual subject monitoring systems communicate with the central monitoring system control unit.

In many cases, a patient may be in need of a care-provision task that is potentially disturbing to the patient's sleep or to sleep of the patient's roommate; for example, a nurse may need to come into the room one or more times during the night to check the patient's blood pressure, temperature, etc. As described immediately hereinbelow, apparatus 270 generally reduces the disturbance to the sleep of the patients, by prioritizing care-provision tasks that are likely to be less disturbing.

Apparatus 270 comprises the plurality of sensors shown in FIG. 20 and described hereinabove. Central monitoring system control unit 278 analyzes the plurality of signals from the respective sensors, and in response thereto, ascertains respective sleep stages of the patients and/or respective sleep stages of roommates of the patients. In response to the respective sleep stages, the control unit determines a prioritization of at least one of the care-provision tasks over at least one other of the care-provision tasks. For example, if patient 2 is awake, but patient 1 and/or a roommate of patient 1 is sleeping, the control unit may prioritize the care-provision task for patient 2 over the care-provision task for patient 1. The control unit then generates an output 284 indicative of the prioritization. Output 284 may, for example, take the form of a message that is displayed on a tablet computer belonging to a nurse, and/or a message displayed via user interface device 276.

In some applications, apparatus 270 further comprises a location sensing system that comprises a plurality of location sensors 286, as described in US 2013/0267791 to Halperin, which is incorporated herein by reference. The location sensing system is configured to identify respective locations of a plurality of care-providers (e.g., clinicians) and/or respective locations of the patients, and to generate a location-sensing-system signal in response thereto. Control unit 278 determines the prioritization further in response to the location-sensing-system signal. For example, if a clinician who is responsible for both patient 1 and patient 2 is closer to patient 1 than to patient 2, the control unit may output a message to the clinician to prioritize patient 1 over patient 2, if patient 1 and patient 2 are in a similarسleep state, e.g., both are awake. In some applications, patient 1 may be prioritized over patient 2 even if patient 2 is sleeping less heavily than patient 1, and/or despite another indicator that would otherwise have favored prioritizing patient 2. Control unit 278 typically determines the prioritization further in response to time-sensitive factors derived from the signals (e.g., heartbeat and/or respiratory signals) from sensors 22. For example, if, by analyzing the signals from the respective patients, the control unit determines that patient 2 is in more urgent need of care than patient 1, patient 2 may be prioritized over patient 1, despite sleep-stage or location factors favoring the prioritization of patient 1.

It is noted that apparatus 270 need not necessarily include a central monitoring system. For example, multiple control units 28 belonging to respective patient monitoring systems may be in communication with each other, and the functionality described hereinabove may be executed by one or several of these control units.

Figure 21:
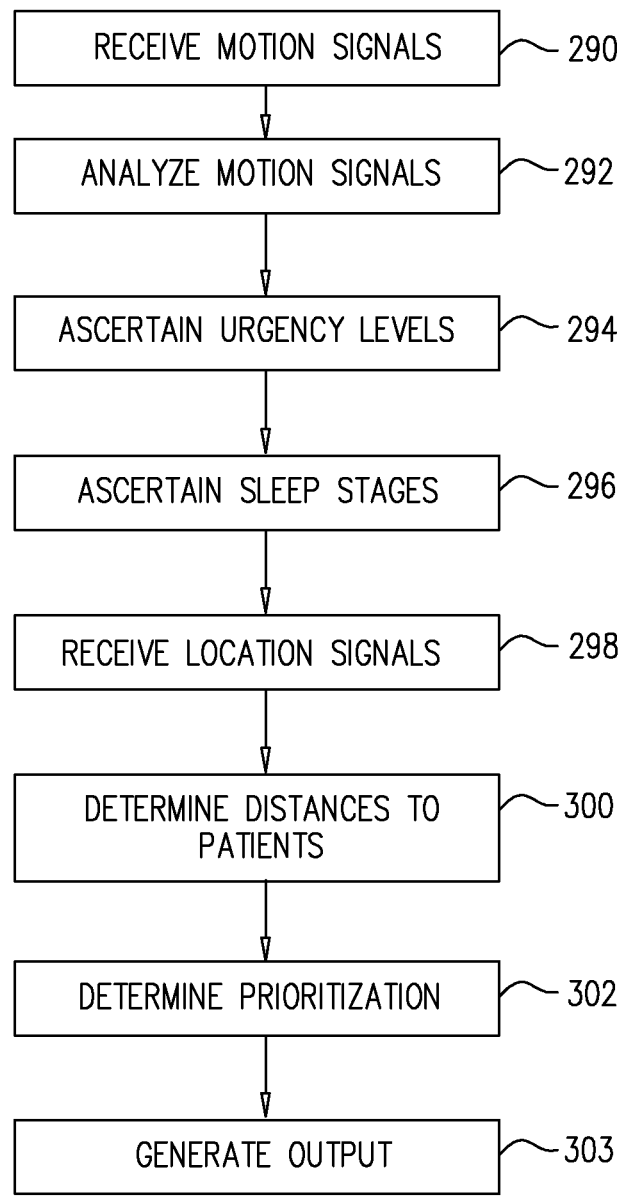
FIG. 21 shows a flow chart depicting aspects of the functioning of apparatus for use with a plurality of patients requiring respective care-provision tasks, in accordance with some applications of the present invention.

FIG. 21 shows a flow chart depicting aspects of the functioning of apparatus 270, as described above, in accordance with some applications of the present invention. At a motion-signal-receiving step 290 and a motion-signal-analyzing step 292, respectively, the control unit (e.g., the control unit of the central monitoring system, and/or control units belonging to respective patient monitoring systems that are in communication with each other) receives and analyzes the motion signals from the patients. In response to the analyzing, the control unit ascertains a level of urgency for each of the patients, at an urgency-ascertaining step 294. The control unit then ascertains sleep stages for one or more relevant patients, at a sleep-stage-ascertaining step 296. Then, at a location-signal-receiving step 298 and a distance-determining step 300, respectively, the control unit receives the location signals, and determines distances of relevant clinicians to relevant patients. Then, at a prioritization-determining step 302, the control unit determines the prioritization, based on one or more of the urgency, sleep-stage, and distance factors. Finally, at an output-generating step 303, the control unit outputs the prioritization.

Figure 22:
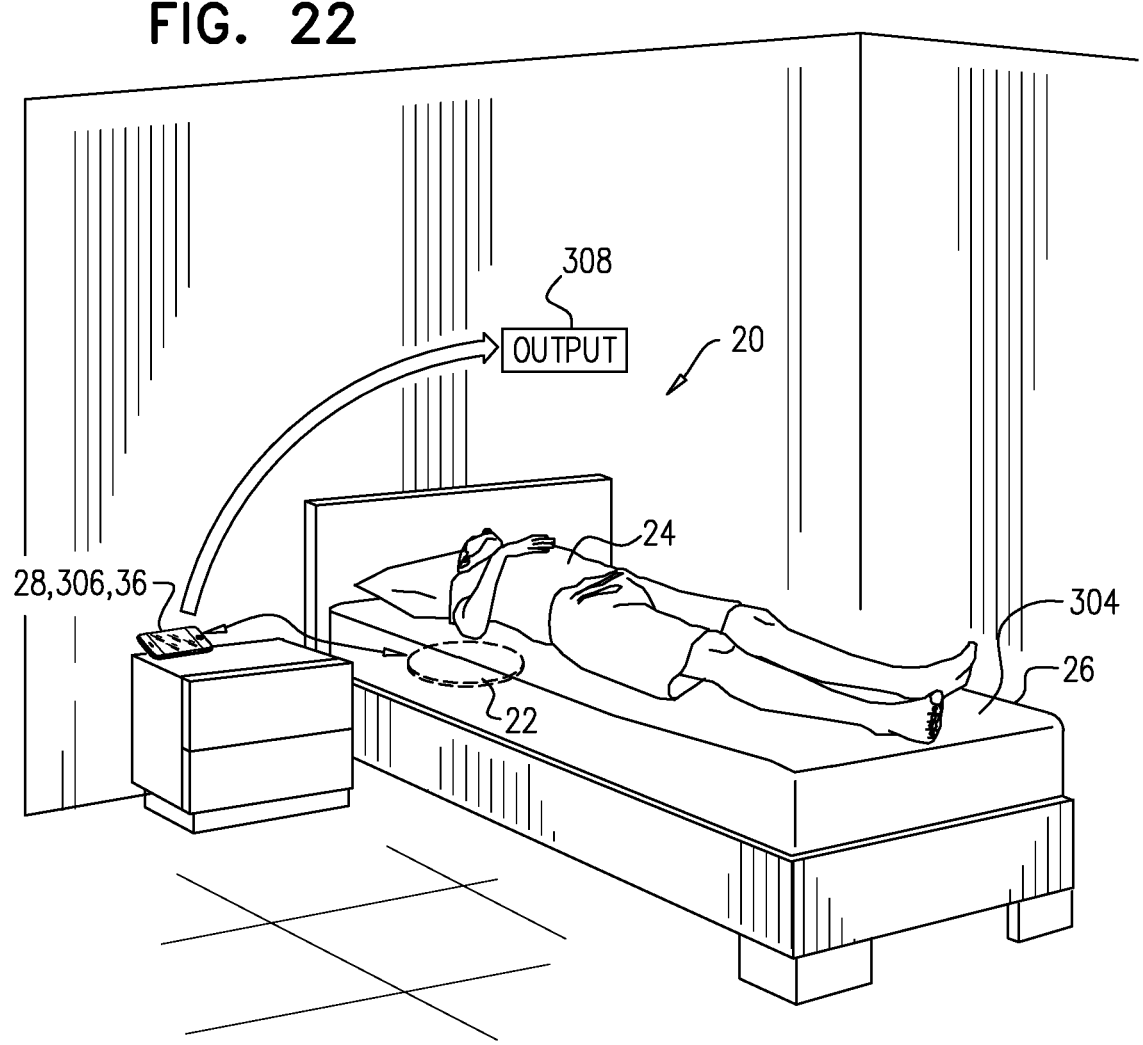
FIG. 22 is a schematic illustration of apparatus for ascertaining that a subject is likely to be resting on a resting surface, in accordance with some applications of the present invention.

Reference is now made to FIG. 22, which is a schematic illustration of subject-monitoring apparatus 20 for ascertaining that a subject 24 is likely to be resting on a resting surface 304 (e.g., the surface of mattress 26), in accordance with some applications of the present invention. Components of subject-monitoring apparatus 20 are as described hereinabove with reference to FIG. 1. Subject-monitoring apparatus 20 comprises a sensor 22, which is generally as described hereinabove, and is configured to monitor subject 24. Subject-monitoring apparatus 20 includes a control unit, which is typically a computer processor, such as computer processor 28 described hereinabove. As described hereinabove, computer processor typically communicates with a memory 29. The computer processor is typically a control unit that performs the algorithms described herein, including analyzing the signal from sensor 22.

In some situations, it is desired to ascertain that a particular subject is getting enough sleep, and/or is sleeping at a particular time. For example, a health insurance company may wish to verify that an insured individual is sleeping healthfully, or a trucking company may wish to verify that a truck driver is getting enough sleep while on the road. In such situations, merely verifying that someone is resting on resting surface 304 is insufficient; rather, the resting person must be identified as the subject with a reasonable degree of confidence. As described hereinbelow, apparatus 20 facilitates this identification by ascertaining that a handheld telecommunications device 306 (e.g., smartphone 36) of the subject is not moving and/or is not being used, such that the resting person is likely to be the subject.

Apparatus 20 comprises sensor 22 and processor 28, which, as described hereinabove, may be a dedicated processor, or may be embodied within a user interface device, e.g., handheld telecommunications device 306 (e.g., smartphone 36) of the subject. (In the latter case, device 306 may communicate directly with sensor 22, e.g., wirelessly.) Sensor 22 monitors resting surface 304, and generates a sensor signal in response thereto. By analyzing the sensor signal, the processor may ascertain that a person is resting on the resting surface. However, the processor may not necessarily ascertain, from the sensor signal alone, whether the resting person is the subject; therefore, the processor also analyzes a signal generated by device 306, which provides a further indication as to whether the subject is resting. Examples of signals generated by device 306 that may be analyzed alone or in combination with each another are the following:

(i) A device-movement signal: The telecommunications device may include a device-movement sensor (e.g., an accelerometer or a GPS sensor) configured to detect movement of the telecommunications device and to generate a device-movement signal in response thereto.

(ii) A usage signal: The telecommunications device may generate a signal indicative of whether the telecommunications device is being used (e.g., whether there is a call in progress, outgoing communication, or any application-use).

Processor 28 identifies a level of correspondence between the sensor signal and the signal generated by the telecommunications device. For example, the level of correspondence may be said to be relatively high if (i) the sensor signal indicates that a person is resting on the resting surface, and the signal generated by the telecommunications device indicates that the device is not being used and/or is not moving, or (ii) the sensor signal indicates that no one is resting on the resting surface, and the signal generated by the telecommunications device indicates that the device is being used and/or is moving. Conversely, the level of correspondence may be said to be relatively low if (i) the sensor signal indicates that a person is resting on the resting surface, but the signal generated by the telecommunications device indicates that the device is being used and/or is moving, or (ii) the sensor signal indicates that no one is resting on the resting surface, but the signal generated by the telecommunications device indicates that the device is not being used and/or is not moving. In response to the level of correspondence, the processor generates an output 308 (e.g., a message displayed on a remote device) that is indicative of whether the subject is likely to be resting on the resting surface.

In general, the processor ascertains that the subject is likely to be resting on the resting surface only if the processor identifies a relatively high level of "positive" correspondence, i.e., the processor ascertains (a) from the sensor signal that a person is resting on the resting surface, and (b) from the signal generated by device 306 that the telecommunications device is not being used and/or is not moving. If, on the other hand, there is a relatively low level of correspondence, or if there is a relatively high level of "negative" correspondence (i.e., both signals suggest that the subject is not resting on the resting surface), the processor will ascertain that the subject is not likely to be resting on the resting surface. Output 308 is generated in response to the ascertaining.

Alternatively or additionally to the identification of a level of correspondence between the sensor signal and a signal generated by device 306, processor 28 may, in response to a signal generated by the telecommunications device, determine if the telecommunications device is within a given distance of the resting surface. If the telecommunications device is within the given distance, the processor ascertains that the subject is likely to be resting on the resting surface, and generates output 308 in response thereto. Conversely, if the telecommunications device is not within the given distance of the resting surface, the processor ascertains that the subject is not likely to be resting on the resting surface, and generates output 308 in response thereto. For example, the processor may check that a short-range signal emitted from the vicinity of the resting surface, e.g., by a wireless-communication component of sensor 22, is received by the telecommunications device. (In the context of the present claims and description, the phrase "given distance" does not necessarily connote a precise numerical distance, but rather, can connote a general range of distances, e.g., the processor may determine if the telecommunications device is within Bluetooth™ range of the resting surface.) Alternatively or additionally, the processor utilizes a signal generated by the telecommunications device that is indicative of coordinates of a location of the telecommunications device, e.g., a GPS location signal. At some prior point in time, the processor receives an input indicative of coordinates of a location of the resting surface, e.g., by prompting the subject to press an input button on the telecommunications device while on the resting surface. The processor then ascertains that the telecommunications device is within the given distance of the resting surface by comparing the location of the telecommunications device with the location of the resting surface.

In some applications, by periodically analyzing a signal generated by the telecommunications device, the processor ascertains that the telecommunications device is periodically used by the subject when the subject is not on the resting surface. For example, the processor may ascertain that the telecommunications device moves periodically, and/or is used periodically, and/or is periodically not in the vicinity of the resting surface, i.e., the telecommunications device is periodically "active". Further to this ascertaining, a "non-active" state of the telecommunications device is more indicative that the subject is likely to be resting on the resting surface, relative to if the telecommunications device were not known to be periodically "active".

Figure 23:
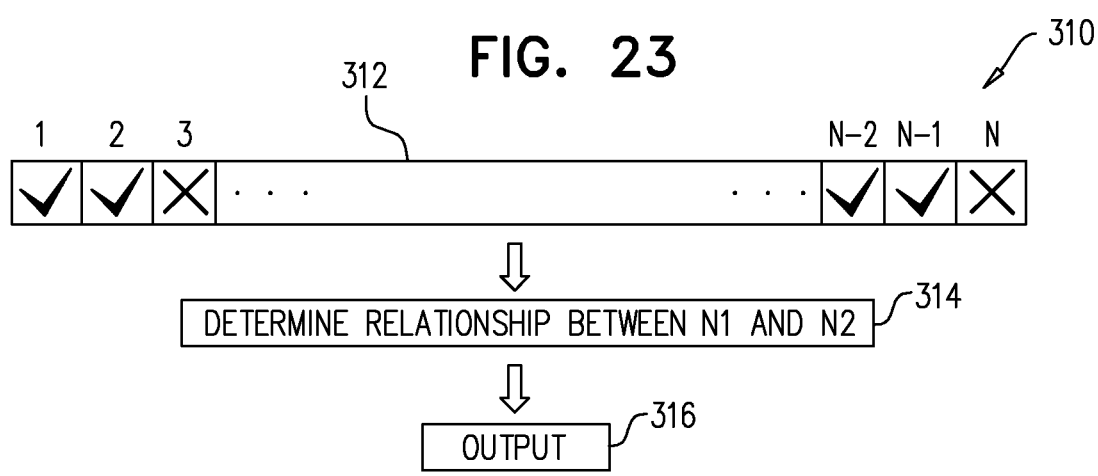
FIG. 23 is a schematic illustration of a technique for generating output, in accordance with some applications of the present invention.

Reference is now made to FIG. 23, which is a schematic illustration of a technique 310 for generating output 308, in accordance with some applications of the present invention. In some applications, a large period of time (e.g., a night) is divided into a plurality of smaller time periods 312. (In FIG. 23, the plurality of time periods is depicted as consisting of N time periods.) Each of these time periods may be a "match," indicated in the figure by a checkmark, or a "non-match," indicated in the figure by an X. A "match" is a time period during which the level of correspondence between the sensor signal and the signal generated by the handheld telecommunications device is greater than a correspondence threshold, and/or the telecommunications device is within the given distance of the resting surface, such that the subject is likely to be resting on the resting surface. In this context, the "sign" of the correspondence is taken into account, i.e., the level of correspondence between the sensor signal and the signal generated by the handheld telecommunications device is greater than the correspondence threshold only if the correspondence is "positive". (As defined above, this means that both signals are indicative of the subject resting on the resting surface.) The processor determines a relationship between the number N1 of matches with the number N2 of non-matches (step 314), and generates output 316 in response to the relationship between N1 and N2, e.g., a ratio of N1 to N2. For example, the processor may generate an output indicating that the subject is likely to be resting on the resting surface only if the ratio N1:N2 exceeds a threshold.

Figure 24:
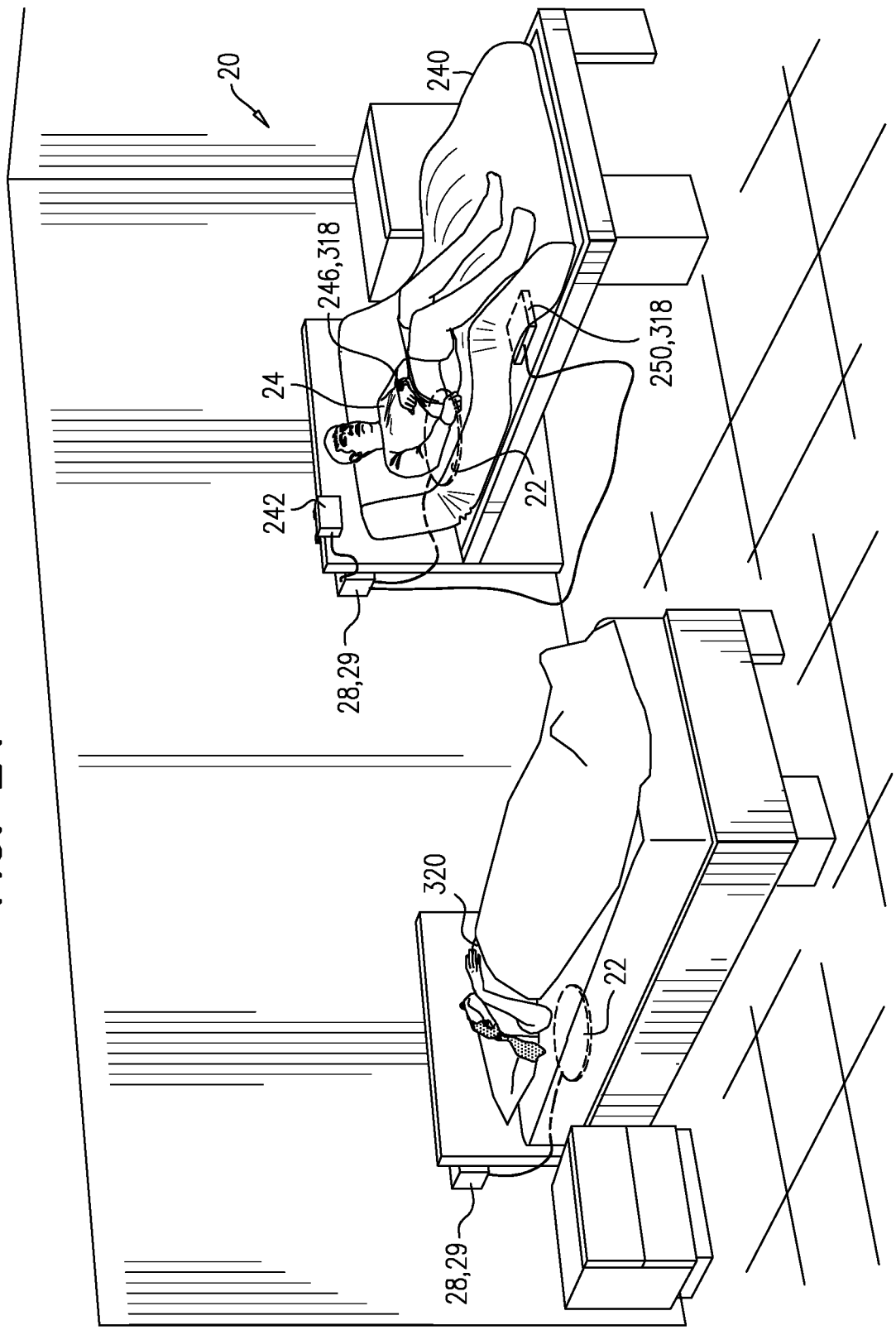
FIG. 24 is a schematic illustration of apparatus for use with a vibrating mechanism and/or an adjustable resting surface, in accordance with some applications of the present invention.

Reference is now made to FIG. 24, which is a schematic illustration of subject-monitoring apparatus 20 for use with a vibrating mechanism 318 and/or adjustable resting surface 240, in accordance with some applications of the present invention. Adjustable resting surface 240 is typically as described hereinabove with reference to FIG. 18. The vibrating mechanism may include vibrating mechanism 250 disposed underneath mattress 26, and/or vibrating wristwatch 246.) Components of subject-monitoring apparatus 20 are as described hereinabove with reference to FIG. 1. Subject-monitoring apparatus 20 comprises a sensor 22, which is generally as described hereinabove, and is configured to monitor subject 24. Subject-monitoring apparatus 20 includes a control unit, which is typically a computer processor, such as computer processor 28 described hereinabove. As described hereinabove, computer processor typically communicates with a memory 29. The computer processor is typically a control unit that performs the algorithms described herein, including analyzing the signal from sensor 22.

Typically, subject 24 is more likely to snore, cough, or have an apnea episode when the subject is in a supine position. Apparatus 20 reduces the frequency of snoring, coughing, and/or apnea of subject 24 by encouraging (e.g., by "nudging") the subject to move from a supine position to a different position.

Control unit 28, which receives the signal from sensor 22 that monitors subject 24, identifies the subject's posture (e.g., sleeping position) by analyzing the sensor signal from sensor 22. (In identifying the subject's posture, the control unit may make use of techniques described in U.S. Pat. No. 8,821,418 to Meger, which is incorporated herein by reference.) In response to the identified posture, e.g., in response to the identified posture being a supine position, the control unit drives vibrating mechanism 318 to vibrate, and/or adjusts a parameter (e.g., an angle) of resting surface 240 by communicating a signal to the resting surface. (FIG. 24 shows the control unit in communication with a parameter-adjusting unit 242 of the resting surface.) The vibration typically "nudges" the subject to change his posture, while the adjustment of the parameter may nudge the subject to change his posture or actually move the subject into the new posture.

In some applications, adjustable resting surface 240 comprises an inflatable pillow, the control unit being configured to adjust a level of inflation of the inflatable pillow. For example, to inhibit coughing and/or snoring, the control unit may drive an inflating mechanism to inflate the inflatable pillow, by communicating a signal to the inflating mechanism.

In some applications, the control unit, which receives the signal from sensor 22 that monitors subject 24, is further configured, in response to analyzing the sensor signal, to identify a sleep stage of the subject. The control unit then drives the vibrating mechanism to vibrate, and/or adjusts the parameter of the resting surface, further in response to the identified sleep stage. For example, the control unit may drive the vibrating mechanism to vibrate, and/or adjust the parameter of the resting surface, in response to the identified sleep stage being within 5 minutes of an onset or an end of an REM sleep stage, since at these points in time, the "nudging" or moving is less likely to disturb the subject's sleep.

In some applications, subject 24 shares a room with a partner 320, and a second sensor 22 monitors partner 320 and generates a second sensor signal in response thereto. As shown in FIG. 24, apparatus 20 typically comprises first and second sensors 22 configured to monitor, respectively, subject 24 and partner 320. (In some applications, a single sensor 22 monitors both the subject and the subject's partner.) It is noted that FIG. 24 shows partner 320 in a separate bed from subject 24, but for some applications the subject and his/her partner share the same bed, e.g., as shown in FIG. 18.

A control unit 28 analyzes the second sensor signal and, in response thereto, identifies a sleep stage of the partner. (As shown, there may be separate control units configured to receive and analyze the subject's and the partner's sensed signals, respectively. For such applications the control units are typically in communication with one another.) The control unit that controls the vibrating mechanism and/or the resting surface drives the vibrating mechanism to vibrate, and/or adjusts the parameter of the resting surface, further in response to the identified sleep stage of the partner. For example, the control unit may nudge or move the subject in response to the partner being in a light sleep stage, since at this stage, snoring of the subject is more likely to disturb the partner.

In some applications, control unit 28, which receives the signal from sensor 22 that monitors subject 24, is further configured to identify a snoring, coughing, or apnea episode of the subject, e.g., by using techniques described in US 2007/0118054 to Pinhas (now abandoned), which is incorporated herein by reference. In response to the identified episode (alternatively or additionally to the other factors described above, such as the sleep state of the subject), the control unit nudges or moves the subject.

Figure 25:
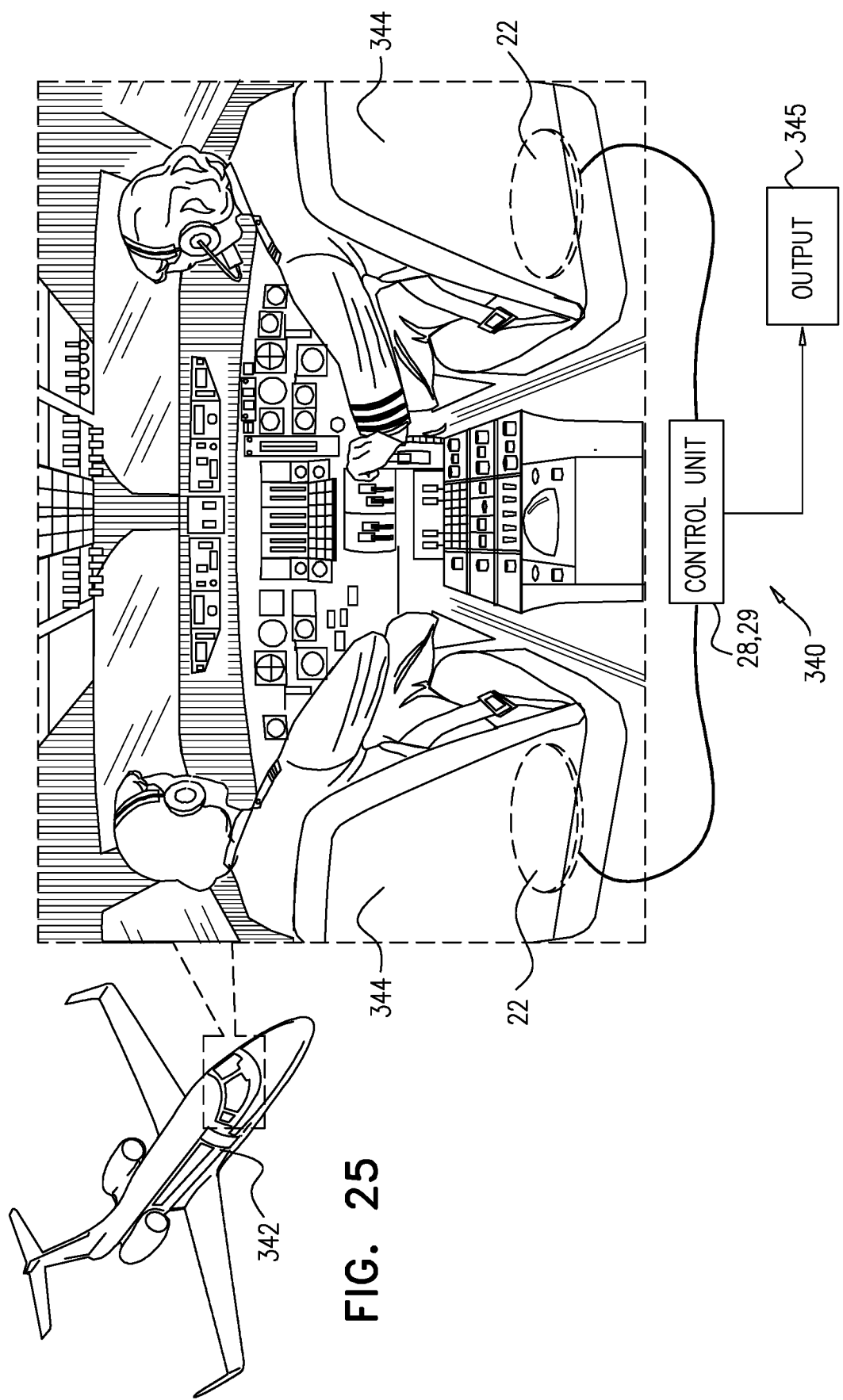
FIG. 25 is a schematic illustration of apparatus for monitoring a subject in a vehicle, in accordance with some applications of the present invention.

Reference is now made to FIG. 25, which is a schematic illustration of apparatus 340 for monitoring a subject in a vehicle, e.g., a multi-person vehicle, such as an airplane 342, in accordance with some applications of the present invention. One or more sensors 22 are placed in one or more seats 344 in the vehicle, and are used to sense physiological activity of the subjects who occupy the seats. Control unit 28 analyzes the motion signals from the sensors, and generates an output 345 (e.g., an alert) in response thereto.

Components of apparatus 340 are generally similar to those of subject-monitoring apparatus 20 described hereinabove with reference to FIG. 1. Sensor 22 is generally as described hereinabove. Apparatus 340 includes a control unit, which is typically a computer processor, such as computer processor 28 described hereinabove. As described hereinabove, computer processor typically communicates with a memory 29. The computer processor is typically a control unit that performs the algorithms described herein, including analyzing the signal from sensor 22.

For example, using apparatus 340:

(a) An alert may be generated if, by analyzing the motion signal, the control unit identifies an elevated stress level of a subject, e.g., by identifying an elevated heart rate, and/or a decreased stroke volume, e.g., as described in WO 2015/008285 to Shinar, which is incorporated herein by reference. For example, in response to the pilot experiencing an elevated stress level, the control unit may generate an alert to another member of the flight crew, and/or individuals on the ground. The control unit may also analyze the signal of the co-pilot, and generate an alert in response to both the pilot and co-pilot experiencing an elevated stress level, since the presence of an elevated stress level in both individuals at the same time is likely to be indicative of an emergency situation. Similarly, an alert may be generated if two or more passengers experience an elevated stress level at the same time.

(b) An alert may be generated if, by analyzing the motion signal, the control unit identifies that it is likely that the subject is experiencing, or will soon experience, a clinical event, such as a heart attack. For example, if the pilot or one of the passengers is experiencing a heart attack, members of the flight crew, and/or a physician who is travelling on the airplane, may be alerted to the situation.

(c) An alert may be generated if, by analyzing the motion signal, the control unit identifies that it is at least somewhat likely that the subject is a carrier of a disease, such as severe acute respiratory syndrome (SARS). For example, if the control unit identifies a change in the baseline heart rate of the subject without any correlation to motion of the subject, the control unit may ascertain that the subject has likely experienced a rapid change in body temperature, which may indicate that the subject is sick. (The baseline heart rate is typically an average heart rate over a period of time, e.g., 1-2 hours.) In response, the control unit may alert the flight crew to isolate the subject.

(d) An alert may be generated if, by analyzing the motion signal, the control unit identifies that the subject (in particular, the pilot or co-pilot) is drowsy or sleeping.

(e) A sleep study may be performed. For example, the control unit may analyze the motion signals from various passengers, and identify which passengers were sleeping at which times. In response, the control unit may generate an output to help the airline improve the sleeping conditions on their aircraft (e.g., by reducing lighting, or increasing leg room).

Apparatus 340 may also be used to control the lighting, temperature, or other cabin-environment parameters, in order to facilitate a more pleasant travelling experience. For example, upon detecting that a significant number of passengers are sleeping or are trying to fall asleep, the lights in the cabin may be dimmed, and/or the movie that is playing may be stopped. Alternatively or additionally, meals may be served to the passengers only if a given number of passengers are awake. To help prevent deep vein thrombosis (DVT), passengers may be prompted to stand up and take a walk, if the control unit detects that they have been sitting in place for too long.

FIG. 26 shows a flow chart for aspects of a method performed using apparatus 340, as described hereinabove, in accordance with some applications of the present invention. At a signal-receiving step 350, the control unit receives the signals from the respective motion sensors; for example, the control unit may receive signals from the pilot's and co-pilot's sensors. At a signal-analyzing step 352, the control unit analyzes the signals. At a first stress-level-determination step 354, the control unit determines whether the pilot's stress level is elevated. If the answer is affirmative, the control unit then determines, at a second stress-level-determination step 356 whether the co-pilot's stress level is elevated. If both stress levels are elevated, the control unit generates an alert, at an alert-generation step 358. Otherwise, the control unit proceeds to check for other factors that may warrant the generation of an alert, and generates an alert (step 358) in response to determining that one or more such factors exist. Thus, the control unit determines, at a sleep-or-drowsiness-determination step 360, whether the pilot (and/or co-pilot) is asleep or drowsy, and at a clinical-event-determination step 362, whether the pilot (and/or co-pilot) might be experiencing, or is about to experience, a clinical event.

Reference is now made to FIG. 27, which is a schematic illustration of apparatus 370 for monitoring a subject in a casino 372, in accordance with some applications of the present invention. As described with reference to FIGS. 25-26, one or more sensors 22 are placed in seats 374 of one or more subjects. Components of apparatus 370 are generally similar to those of subject-monitoring apparatus 20 described hereinabove with reference to FIGS. 1-5. Apparatus 370 includes a control unit, which is typically a computer processor, such as computer processor 28 described hereinabove. As described hereinabove, computer processor typically communicates with a memory 29. The computer processor is typically a control unit that performs the algorithms described herein, including analyzing the signal from sensor 22.

By analyzing the motion signals, control unit 28 identifies an elevated stress level of one or more subjects. An elevated stress level, which is commonly experienced while performing casino-related activities, may be indicative of an upcoming clinical event, particularly for subjects who are elderly and/or infirm. The control unit generates an alert in response to the elevated stress level, such that, for example, the subject can be told to take a break from his activities. In some cases, such as in multi-player games, simultaneous elevated stress levels of two or more subjects may indicate that the subjects are colluding. The control unit may therefore generate the alert in response to each of two or more subjects having an elevated stress level at the same time.

Figure 28:
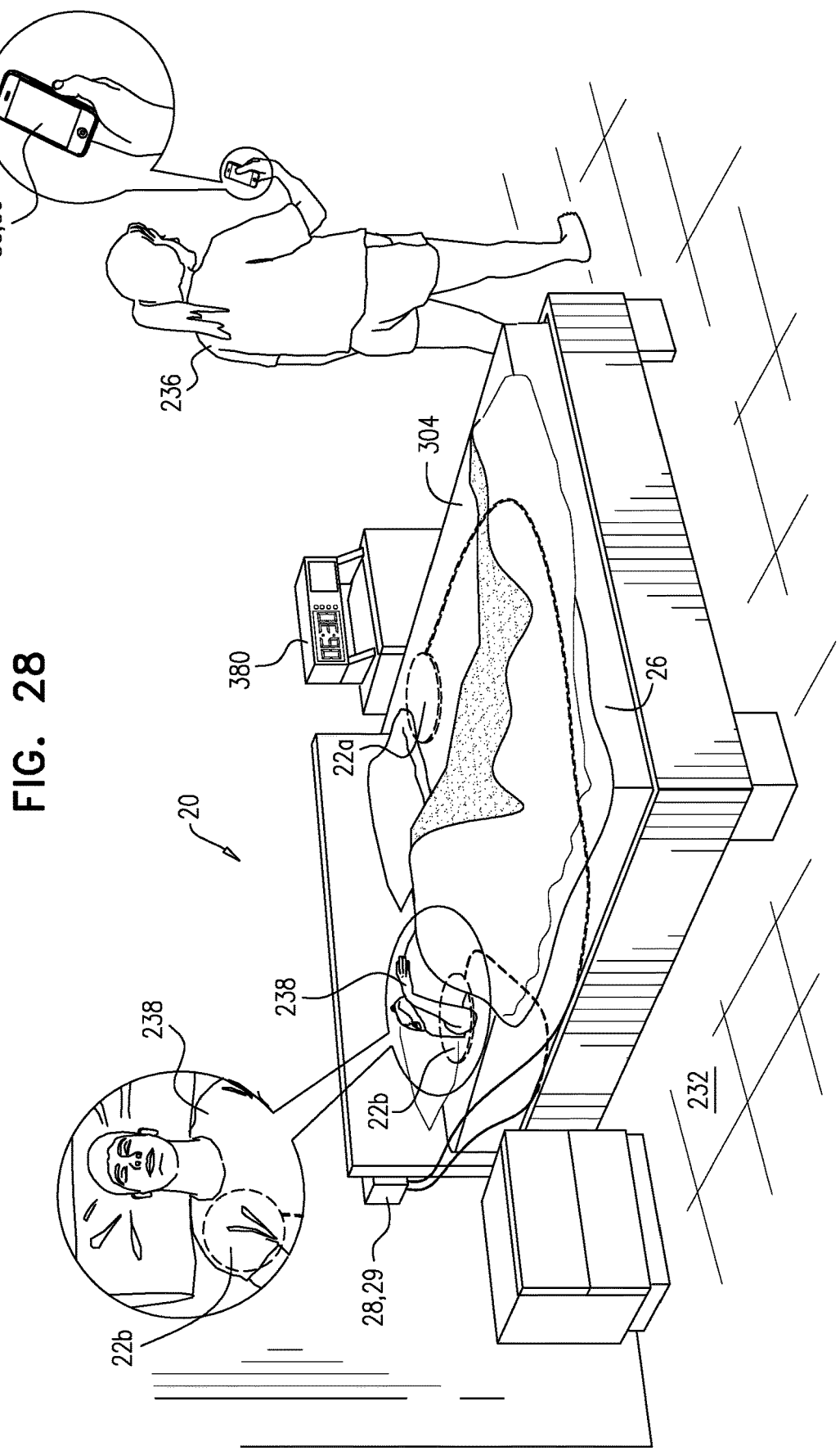
FIG. 28 is a schematic illustration of apparatus for use with an alarm clock for waking a subject, in accordance with some applications of the present invention.

Reference is now made to FIG. 28, which is a schematic illustration of subject-monitoring apparatus 20, the apparatus being for use with an alarm clock 380 for waking first subject 236, in accordance with some applications of the present invention. Alarm clock 380 may be embodied, for example, in a smartphone or clock radio. Components of subject-monitoring apparatus 20 are as described hereinabove with reference to FIG. 1. Subject-monitoring apparatus 20 comprises one or more sensors 22, which are generally as described hereinabove, and are configured to monitor subjects 236 and 238 (subjects 236 and 238 corresponding to subject 24 of FIG. 1). Subject-monitoring apparatus 20 includes a control unit, which is typically a computer processor, such as computer processor 28 described hereinabove. As described hereinabove, computer processor typically communicates with a memory 29. The computer processor is typically a control unit that performs the algorithms described herein, including analyzing the signal from sensor 22.

In some applications, as shown in FIG. 28, control unit 28 is separate from alarm clock 380, and communicates therewith by wired or wireless communication means. In other applications, the alarm clock and control unit are integrated into a common unit.

A first sensor 22a monitors resting surface 304 (e.g., the surface of mattress 26), and generates a signal in response thereto. Control unit 28 analyzes the signal. If, in response to the analyzing, the control unit determines that the resting surface is likely not being occupied by subject 236, the control unit inhibits the alarm clock from generating an alarm, and/or stops an alarm that is in progress. (Alternatively, the alarm clock does not generate an alarm unless it is driven to do so by the control unit, in response to the control unit determining that the resting surface is likely being occupied by subject 236.) This reduces the likelihood of an alarm waking other members of the household (e.g., a second subject 238, such as the subject's partner), in cases where first subject 236 arose from resting surface 304 without taking measures to ensure that the alarm would not subsequently begin or continue to sound. Typically, the control unit is configured to determine that the resting surface is likely not being occupied by first subject 236, even if the resting surface is occupied by someone. For example, even if the signal from a second sensor 22b indicates bed-occupation, the control unit may determine that the resting surface is likely not being occupied by first subject 236, if the signal from sensor 22a (on the right side of the bed) does not indicate bed-occupation.

In some cases, first subject 236 might arise from bed (thus causing the control unit to inhibit the generating of an alarm), but return to bed thereafter. Hence, the control unit is typically configured to stop inhibiting the alarm clock from generating an alarm, in response to determining that the resting surface is likely being occupied by first subject 236. (Alternatively, the control unit may drive the alarm clock to generate an alarm, in response to determining that the resting surface is likely being occupied by first subject 236.) In some cases, first subject 236 might not arise from bed, despite a first alarm having been generated by the alarm clock. Hence, the control unit is typically configured to drive the alarm clock to generate a second alarm, in response to determining that the resting surface is likely being occupied by the subject.

In some applications, when determining whether to inhibit the alarm clock from generating an alarm (or drive the alarm clock to generate an alarm), the control unit 28 also takes into account the sleep stage of second subject 238, who is typically a subject for whom the alarm is not intended. For example, FIG. 28 shows second subject 238 sharing a common sleep area with first subject 236. Sensor 22b monitors second subject 238, and generates a sensor signal in response thereto. Control unit 28 is configured (e.g., via user interface device 35, described hereinabove with reference to FIG. 1) to accept an input indicative of (i) an earliest desired awakening time, and (ii) a latest desired awakening time, for first subject 236. At a particular time between the earliest desired awakening time and the latest desired awakening time, the control unit analyzes the sensor signal from sensor 22b. In response to the analyzing, the control unit determines a sleep stage of second subject 238, and, in response to the sleep stage, decides whether to drive the alarm clock to generate an alarm.

For example, at an earliest desired awakening time of 6:00, the control unit may check the sleep stage of second subject 238. If second subject 238 is sleeping lightly, the control unit may withhold driving the alarm clock to generate an alarm until (i) second subject 238 wakes up or begins to sleep more deeply, or (ii) the latest desired awakening time (e.g., 6:30) is reached. Alternatively, the alarm may be set for 6:00, and the control unit may inhibit the alarm clock from generating the alarm until condition (i) or (ii) is satisfied.

In some applications, the control unit analyzes the sensor signal over a plurality of sleeping sessions, and identifies a sleep-sensitivity of second subject 238 to at least one phenomenon that is generally detrimental to sleep, e.g., as described hereinabove with reference to FIG. 18. (The phenomenon may be the generation of the alarm by the alarm clock, such that, for example, second subject 238 is considered to have high sleep-sensitivity is he is readily woken by the alarm.) In response to the identified sleep-sensitivity, the control unit decides whether to drive the alarm clock to generate an alarm. For example, if second subject 238 has high sleep-sensitivity, the control unit may withhold from driving the alarm clock to generate an alarm until second subject 238 is awake or until the latest desired awakening time is reached.

Alternatively or additionally, the control unit may calculate a sleep score for the second subject, the sleep score being based on the duration and/or quality of the second subject's sleep during a preceding interval, as described hereinabove with reference to FIG. 18. In response to the sleep score, the control unit decides whether to drive the alarm clock to generate an alarm. For example, if the sleep score of second subject 238 is low (e.g., second subject 238 had a less-than-average amount of slow-wave and REM sleep during the night), the control unit may withhold from driving the alarm clock to generate an alarm until second subject 238 is awake or the latest desired awakening time is reached.

Alternatively or additionally, the control unit may determine whether to drive the alarm clock to generate an alarm in response to a health condition of the second subject. For example, if second subject 238 is recovering from an illness, the control unit may withhold from driving the alarm clock to generate an alarm until second subject 238 is awake or the latest desired awakening time is reached.

Figure 29:
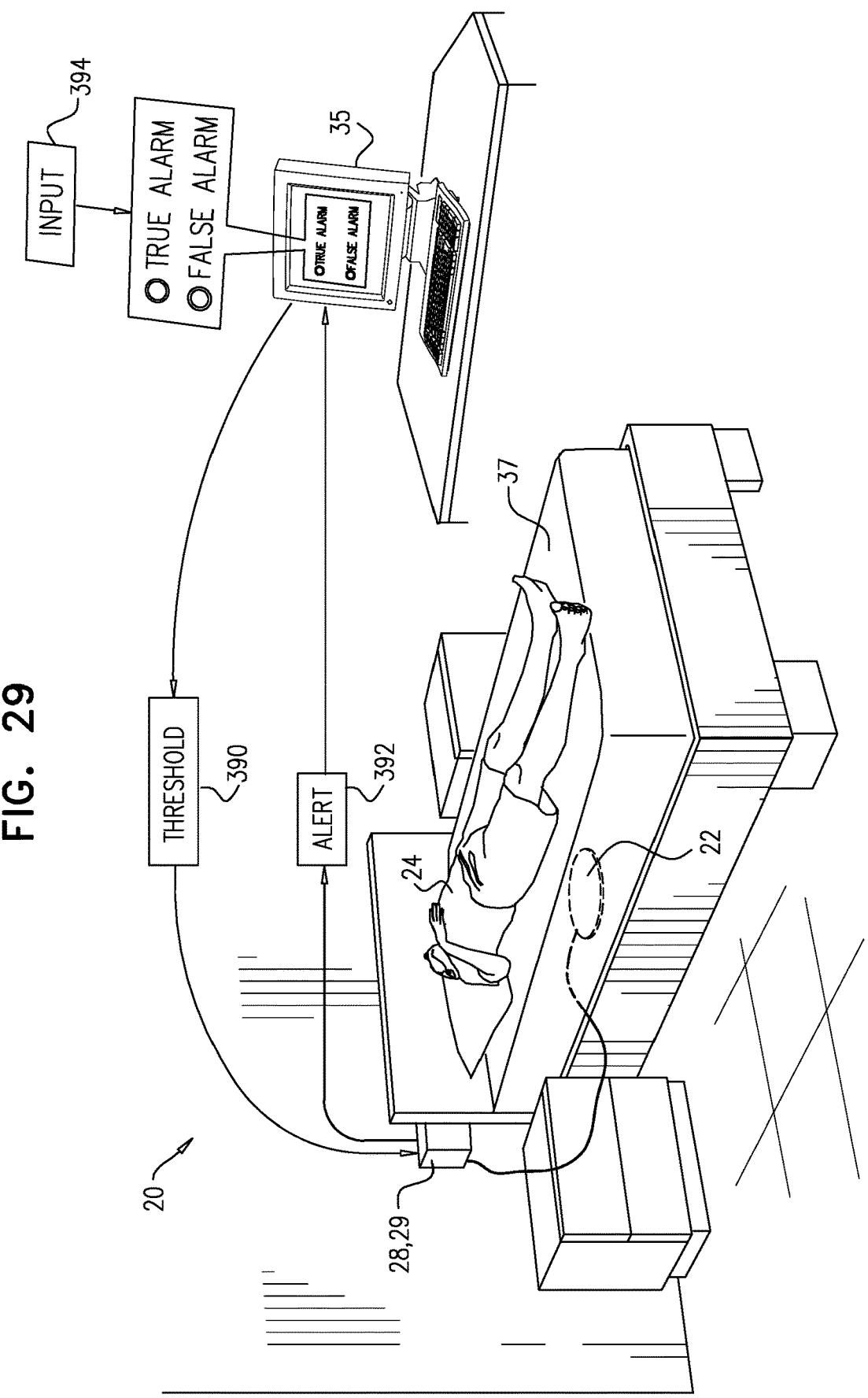
FIG. 29 is a schematic illustration of apparatus for monitoring a patient, in accordance with some applications of the present invention.

Reference is now made to FIG. 29, which is a schematic illustration of subject-monitoring apparatus 20 for monitoring subject 24, when the subject is a patient in a hospital, in accordance with some applications of the present invention. Components of subject-monitoring apparatus 20 are as described hereinabove with reference to FIG. 1. Subject-monitoring apparatus 20 comprises one or more sensors 22, which are generally as described hereinabove, and are configured to monitor subject 24. Subject-monitoring apparatus 20 includes a control unit, which is typically a computer processor, such as computer processor 28 described hereinabove. As described hereinabove, computer processor typically communicates with a memory 29. The computer processor is typically a control unit that performs the algorithms described herein, including analyzing the signal from sensor 22.

Sensor 22 measures a clinical parameter (e.g., a heart rate or breathing rate) of the patient, and generates a signal in response thereto. Control unit 28 receives the signal from the sensor and compares the clinical parameter to a threshold 390. In response to the comparison, the control unit may generate an alert 392 to a clinician, via user interface device 35 (which is typically as described with reference to FIG. 1). User interface device 35 then receives an input 394 from the clinician, the input indicating whether the clinician believes the alert to have been justified. The control unit then adjusts the threshold in response to the input.

For example, if threshold 390 for the patient's heart rate is 90 beats per minute, and the patient's heart beat exceeds the threshold, then the control unit may generate alert 392. The responding clinician then examines the patient, and determines whether the alert was justified. If the clinician indicates, via user interface device 35, that the alert was not justified (i.e., it was a "false alarm"), the control unit may adjust the threshold, for example, to 95 beats per minute. Alternatively, if the clinician indicates that the alarm was justified (i.e., it was a "true alarm"), the control unit may "be conservative" and adjust the threshold to 85 beats per minute. In this manner, the feedback loop depicted in FIG. 29 is generated, whereby the control unit "learns" the proper threshold from experience.

In general, the adjustment of the threshold may be in response to more than one input. For example, the control unit may adjust the threshold only after several false alarms.

The control unit may also adjust the threshold in response to one or more inputs that were received in response to alerts that were generated for a different patient. For example, if Patient A is afflicted by a particular virus, and there is a chance that Patient B might have caught the same virus, the threshold for Patient B may be adjusted in response to a "true alarm" input for Patient A.

In general, computer processor 28 may be embodied as a single computer processor 28, or a cooperatively networked or clustered set of computer processors. Computer processor 28 is typically a programmed digital computing device comprising a central processing unit (CPU), random access memory (RAM), non-volatile secondary storage, such as a hard drive or CD ROM drive, network interfaces, and/or peripheral devices. Program code, including software programs, and data are loaded into the RAM for execution and processing by the CPU and results are generated for display, output, transmittal, or storage, as is known in the art. Typically, computer processor 28 is connected to one or more sensors via one or more wired or wireless connections. Computer processor 28 is typically configured to receive signals (e.g., motion signals) from the one or more sensors, and to process these signals as described herein. In the context of the claims and specification of the present application, the term "motion signal" is used to denote any signal that is generated by a sensor, upon the sensor sensing motion. Such motion may include, for example, respiratory motion, cardiac motion, or other body motion, e.g., large body-movement. Similarly, the term "motion sensor" is used to denote any sensor that senses motion, including the types of motion delineated above.

Applications of the invention described herein can take the form of a computer program product accessible from a computer-usable or computer-readable medium (e.g., a non-transitory computer-readable medium) providing program code for use by or in connection with a computer or any instruction execution system, such as computer processor 28. For the purposes of this description, a computer-usable or computer readable medium can be any apparatus that can comprise, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Typically, the computer-usable or computer readable medium is a non-transitory computer-usable or computer readable medium.

Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W) and DVD.

A data processing system suitable for storing and/or executing program code will include at least one processor (e.g., computer processor 28) coupled directly or indirectly to memory elements (e.g., memory 29) through a system bus. The memory elements can include local memory employed during actual execution of the program code, bulk storage, and cache memories which provide temporary storage of at least some program code in order to reduce the number of times code must be retrieved from bulk storage during execution. The system can read the inventive instructions on the program storage devices and follow these instructions to execute the methodology of the embodiments of the invention.

Network adapters may be coupled to the processor to enable the processor to become coupled to other processors or remote printers or storage devices through intervening private or public networks. Modems, cable modem and Ethernet cards are just a few of the currently available types of network adapters.

Computer program code for carrying out operations of the present invention may be written in any combination of one or more programming languages, including an object oriented programming language such as Java, Smalltalk, C++ or the like and conventional procedural programming languages, such as the C programming language or similar programming languages.

It will be understood that each block of the flowcharts shown in FIGS. 2, 4, 5, 8, 11, 13-15, 17, 21, 23, 26, 29 and combinations of blocks in the flowcharts, can be implemented by computer program instructions. These computer program instructions may be provided to a processor of a general purpose computer, special purpose computer, or other programmable data processing apparatus to produce a machine, such that the instructions, which execute via the processor of the computer (e.g., computer processor 28) or other programmable data processing apparatus, create means for implementing the functions/acts specified in the flowcharts and/or algorithms described in the present application. These computer program instructions may also be stored in a computer-readable medium (e.g., a non-transitory computer-readable medium) that can direct a computer or other programmable data processing apparatus to function in a particular manner, such that the instructions stored in the computer-readable medium produce an article of manufacture including instruction means which implement the function/act specified in the flowchart blocks and algorithms. The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide processes for implementing the functions/acts specified in the flowcharts and/or algorithms described in the present application.

Computer processor 28 is typically a hardware device programmed with computer program instructions to produce a special purpose computer. For example, when programmed to perform the algorithms described with reference to FIGS. 2, 4, and 5, computer processor 28 typically acts as a special purpose menstrual-state and/or pregnancy-state identification computer processor. When programmed to perform the algorithms described with reference to FIG. 8, computer processor 28 typically acts as a special purpose sleep-stage monitoring computer processor. When programmed to perform the algorithms described with reference to FIG. 11, computer processor 28 typically acts as a special purpose device activation computer processor. When programmed to perform the algorithms described with reference to FIGS. 13-15, computer processor 28 typically acts as a special purpose room-climate-controlling computer processor. When programmed to perform the algorithms described with reference to FIG. 17, computer processor 28 typically acts as a special purpose subject-prioritization computer processor. When programmed to perform the algorithms described with reference to FIG. 23, computer processor 28 typically acts as a special purpose sleep-monitoring computer processor. When programmed to perform the algorithms described with reference to FIG. 26, computer processor 28 typically acts as a special purpose vehicleoccupant-monitoring computer processor. When programmed to perform the algorithms described with reference to FIG. 29, computer processor 28 typically acts as a special purpose threshold-adjusting computer processor. Typically, the operations described herein that are performed by computer processor 28 transform the physical state of memory 29, which is a real physical article, to have a different magnetic polarity, electrical charge, or the like depending on the technology of the memory that is used.

It is noted that the above description of computer processor 28 and memory 29, and the manner in which the computer processor and the memory perform the functions described herein is generally applicable to central monitoring system computer processor 280 and memory 282. Central monitoring system computer processor 280 is typically a hardware device programmed with computer program instructions to produce a special purpose computer. When programmed to perform the algorithms described with reference to FIG. 21, computer processor 280 typically acts as a special purpose patient-prioritization computer processor.

There is therefore provided the following inventive concepts, in accordance with some applications of the present invention:

Inventive concept 1. Apparatus for monitoring a female subject, the apparatus comprising:
- a sensor, configured to monitor the subject without contacting the subject or clothes the subject is wearing, and without viewing the subject or clothes the subject is wearing, and to generate a sensor signal in response to the monitoring; and
- a computer processor, configured to:
  - receive the sensor signal,
  - analyze the sensor signal,
  - in response to the analyzing, identify a menstrual state of the subject, and
  - generate an output in response thereto.

Inventive concept 2. The apparatus according to inventive concept 1, wherein the computer processor is configured to identify the subject's menstrual state without determining a temperature of the subject.

Inventive concept 3. The apparatus according to inventive concept 1, wherein the sensor is not configured to measure a temperature of the subject.

Inventive concept 4. The apparatus according to inventive concept 1, wherein the computer processor is configured to identify the subject's menstrual state by identifying a current menstrual state of the subject.

Inventive concept 5. The apparatus according to inventive concept 1, wherein the computer processor is configured to identify the subject's menstrual state by predicting an occurrence of a future menstrual state of the subject.

Inventive concept 6. The apparatus according to inventive concept 1, wherein the sensor is configured to be disposed upon or within a bed of the subject, and is configured to monitor the subject automatically while the subject is in her bed.

Inventive concept 7. The apparatus according to inventive concept 1, wherein the computer processor is configured to identify the menstrual state of the subject, using a machine-learning algorithm.

Inventive concept 8. The apparatus according to inventive concept 1, wherein the sensor is configured to monitor the subject without requiring compliance of the subject.

Inventive concept 9. The apparatus according to inventive concept 1, wherein the output includes a control signal to a room-climate-regulation device, and the computer processor is configured to generate the output by communicating the control signal to the room-climate-regulation device in response to the identified menstrual state.

Inventive concept 10. The apparatus according to inventive concept 1, wherein the computer processor is further configured, in response to identifying the subject's menstrual state, to identify that the subject is likely to experience premenstrual syndrome (PMS) in more than 0.5 days,
the computer processor being configured to generate the output in response thereto.

Inventive concept 11. The apparatus according to any one of inventive concepts 1-10, wherein the computer processor is configured to identify the menstrual state of the subject by identifying that the subject is likely to ovulate in less than 10 days.

Inventive concept 12. The apparatus according to inventive concept 11, wherein the computer processor is configured to identify the menstrual state of the subject by identifying that the subject is likely to ovulate in less than five days.

Inventive concept 13. The apparatus according to inventive concept 11, wherein the computer processor is configured to identify the menstrual state of the subject by identifying that the subject is likely to ovulate in more than 0.5 days.

Inventive concept 14. The apparatus according to inventive concept 11, wherein the computer processor is configured to derive a heart rate variability (HRV) signal from the sensor signal, and to identify the subject's menstrual state, in response thereto.

Inventive concept 15. The apparatus according to inventive concept 11, further comprising an input unit,
wherein the computer processor is configured to identify that the subject is likely to ovulate in less than 10 days by:
at least once, prior to currently receiving the sensor signal:
receiving, via the input unit, an input that is indicative of a phase of the subject's menstrual cycle, and
identifying an aspect of the sensor signal at a time at which the input was received,
in response to the input and the identified aspect of the sensor signal, learning an ovulation-prediction rule, and
using the ovulation-prediction rule to identify that the subject is likely to ovulate in less than 10 days, based upon the currently-received sensor signal.

Inventive concept 16. The apparatus according to any one of inventive concepts 1-10,
wherein the computer processor is further configured, in response to identifying the menstrual state of the subject, to identify that the subject is likely to experience premenstrual syndrome (PMS) in less than three days,
the computer processor being configured to generate the output in response thereto.

Inventive concept 17. The apparatus according to inventive concept 16, wherein the computer processor is configured to derive a heart rate variability (HRV) signal from the sensor signal, and to identify the subject's menstrual state, in response thereto.

Inventive concept 18. The apparatus according to inventive concept 16, further comprising an input unit,
wherein the computer processor is configured to identify that the subject is likely to experience PMS in less than three days by:
at least once, prior to currently receiving the sensor signal:
receiving, via the input unit, an input that is indicative of an occurrence of PMS of the subject, and identifying an aspect of the sensor signal at a time at which the input was received, in response to the input and the identified aspect of the sensor signal, learning a PMS-prediction rule, and using the PMS-prediction rule to identify that the subject is likely to experience PMS in less than three days, based upon the currently-received sensor signal.

Inventive concept 19. The apparatus according to any one of inventive concepts 1-10, wherein the computer processor is configured:

in response to the analyzing, to identify an aspect of the sensor signal selected from the group consisting of: a cardiac-related aspect of the sensor signal, and a respiration-related aspect of the sensor signal, and to identify the menstrual state of the subject, in response to the identified aspect.

Inventive concept 20. The apparatus according to inventive concept 19, wherein the identified aspect of the sensor signal includes a respiratory rate of the subject, and wherein the computer processor is configured to identify the menstrual state of the subject by comparing the identified respiratory rate to a baseline respiratory rate.

Inventive concept 21. The apparatus according to inventive concept 19, further comprising an input unit, wherein the identified aspect of the sensor signal is a currently-identified aspect of the sensor signal, and wherein the computer processor is configured to identify the current phase of the menstrual cycle by:

at least once, prior to the identification of the currently-identified aspect of the sensor signal:

receiving, via the input unit, an input that is indicative of a phase of the subject's menstrual cycle, and identifying an aspect of the sensor signal at a time at which the input was received, in response to the input and the identified aspect of the sensor signal, learning a phase-identification rule, and using the phase-identification rule to identify the menstrual state of the subject.

Inventive concept 22. The apparatus according to inventive concept 19, wherein the identified aspect of the sensor signal includes a heart rate variability (HRV) signal, the computer processor being configured to identify the menstrual state in response to the HRV signal.

Inventive concept 23. The apparatus according to inventive concept 22, wherein, in response to the HRV signal, the computer processor is configured to identify that the current phase of the subject's menstrual cycle is a late follicular phase.

Inventive concept 24. The apparatus according to inventive concept 23, wherein the computer processor is configured to identify that the current phase of the subject's menstrual cycle is the late follicular phase in response to an aspect of a component of a power spectrum of the HRV signal.

Inventive concept 25. The apparatus according to inventive concept 24, wherein the computer processor is configured to identify that the current phase of the subject's menstrual cycle is the late follicular phase by identifying that the component of the power spectrum of the HRV signal has an amplitude that exceeds a threshold.

Inventive concept 26. The apparatus according to inventive concept 24, wherein the component of the power spectrum of the HRV signal lies between 0.1 and 0.5 Hz, the computer processor being configured to identify that the current phase of the subject's menstrual cycle is the late follicular phase in response to an aspect of the component of the power spectrum.

Inventive concept 27. The apparatus according to inventive concept 19, wherein the identified aspect of the sensor signal includes a heart rate of the subject, and wherein the computer processor is configured to identify the menstrual state of the subject by comparing the identified heart rate to a baseline heart rate.

Inventive concept 28. The apparatus according to inventive concept 27, wherein the computer processor is configured, in response to the comparing, to:

ascertain that the identified heart rate is greater than the baseline heart rate; and in response thereto, identify the menstrual state of the subject by identifying that the subject is currently within a given amount of time of ovulation of the subject.

Inventive concept 29. The apparatus according to inventive concept 28, wherein the computer processor is configured to identify that the subject is currently within the given amount of time of ovulation of the subject by identifying that less than the given amount of time has transpired since the subject ovulated.

Inventive concept 30. The apparatus according to inventive concept 28, wherein the computer processor is configured, in response to ascertaining that the identified heart rate is greater than the baseline heart rate, to identify that the subject is currently within less than two days of ovulation of the subject.

Inventive concept 31. The apparatus according to inventive concept 28, wherein the computer processor is configured to identify that the subject is currently within the given amount of time of ovulation of the subject in response to the identified heart rate being less than five heartbeats-per-minute greater than the baseline heart rate.

Inventive concept 32. The apparatus according to inventive concept 19, wherein the sensor is configured to monitor the subject during a sleeping session of the subject.

Inventive concept 33. The apparatus according to inventive concept 32, wherein the computer processor is configured to analyze the sensor signal by identifying an aspect of the sensor signal that is exhibited at least two hours from a beginning of the sleeping session, and wherein the computer processor is configured to identify the menstrual state of the subject (i) in response to the aspect of the sensor signal that is exhibited at least two hours from the beginning of the sleeping session, and (ii) substantially not in response to any aspect of the sensor signal that is exhibited less than two hours from the beginning of the sleeping session.

Inventive concept 34. The apparatus according to inventive concept 32, wherein the computer processor is further configured, in response to analyzing the sensor signal, to determine a level of motion of the subject, wherein the computer processor is configured to analyze the sensor signal by identifying an aspect of the sensor signal that is exhibited while the level of motion does not exceed a threshold, and wherein the computer processor is configured to identify the menstrual state of the subject (i) in response to the aspect of the sensor signal that is exhibited while the level of motion does not exceed the threshold, and (ii)

substantially not in response to any aspect of the sensor signal that is exhibited while the level of motion exceeds the threshold.

Inventive concept 35. The apparatus according to inventive concept 32,
wherein the computer processor is further configured, in response to analyzing the sensor signal, to identify a sleep stage of the subject during the sleeping session,
wherein the computer processor is configured to analyze the sensor signal by identifying an aspect of the sensor signal that is exhibited while the identified sleep stage is a particular sleep stage, and
wherein the computer processor is configured to identify the menstrual state of the subject (i) in response to the aspect of the sensor signal that is exhibited while the identified sleep stage is the particular sleep stage, and (ii) substantially not in response to any aspect of the sensor signal that is exhibited while the identified sleep stage is not the particular sleep stage.

Inventive concept 36. The apparatus according to inventive concept 35, wherein the particular sleep stage is a slow-wave sleep stage.

Inventive concept 37. The apparatus according to inventive concept 35, wherein the particular sleep stage is a rapid-eye-movement sleep stage.

Inventive concept 38. The apparatus according to inventive concept 37, wherein the identified aspect of the sensor signal includes a heart rate variability (HRV) signal, the computer processor being configured to identify the menstrual state of the subject in response to the HRV signal that is exhibited while the identified sleep stage is the particular sleep stage.

Inventive concept 39. The apparatus according to inventive concept 32,
wherein the computer processor is further configured, in response to analyzing the sensor signal, to identify an end of a chronologically-first sleep cycle of the subject during the sleeping session,
wherein the computer processor is configured to analyze the sensor signal by identifying an aspect of the sensor signal that is exhibited following the end of the chronologically-first sleep cycle, and
wherein the computer processor is configured to identify the menstrual state of the subject (i) in response to the aspect of the sensor signal that is exhibited following the end of the chronologically-first sleep cycle, and (ii) substantially not in response to any aspect of the sensor signal that is exhibited before the end of the chronologically-first sleep cycle.

Inventive concept 40. The apparatus according to inventive concept 39,
wherein the computer processor is further configured, in response to analyzing the sensor signal, to identify an end of a chronologically-second sleep cycle of the subject during the sleeping session,
wherein the computer processor is configured to analyze the sensor signal by identifying an aspect of the sensor signal that is exhibited following the end of the chronologically-second sleep cycle, and
wherein the computer processor is configured to identify the menstrual state of the subject (i) in response to the aspect of the sensor signal that is exhibited following the end of the chronologically-second sleep cycle, and (ii) substantially not in response to any aspect of the sensor signal that is exhibited before the end of the chronologically-second sleep cycle.

Inventive concept 41. Apparatus for monitoring a female subject and for use with a bed, the apparatus comprising:
a sensor configured to be disposed upon or within the bed, to automatically monitor the subject while the subject is in the bed, and to generate a sensor signal in response to the monitoring; and
a computer processor, configured to:
receive the sensor signal,
analyze the sensor signal,
in response to the analyzing, identify a menstrual state of the subject, and
generate an output in response thereto.

Inventive concept 42. The apparatus according to inventive concept 41, wherein the bed includes a mattress, and wherein the sensor is configured to be disposed underneath the mattress and to automatically monitor the subject while the subject is lying upon the mattress.

Inventive concept 43. The apparatus according to inventive concept 41, wherein the computer processor is configured to identify the subject's menstrual state without determining a temperature of the subject.

Inventive concept 44. The apparatus according to inventive concept 41, wherein the sensor is configured not to measure a temperature of the subject.

Inventive concept 45. The apparatus according to inventive concept 41, wherein the sensor is configured to monitor the subject without having a direct line of sight of the subject or clothes the subject is wearing.

Inventive concept 46. The apparatus according to inventive concept 41, wherein the computer processor is configured to identify the subject's menstrual state by identifying a current menstrual state of the subject.

Inventive concept 47. The apparatus according to inventive concept 41, wherein the computer processor is configured to identify the subject's menstrual state by predicting an occurrence of a future menstrual state of the subject.

Inventive concept 48. The apparatus according to inventive concept 41, wherein the computer processor is configured to identify the menstrual state of the subject, using a machine-learning algorithm.

Inventive concept 49. The apparatus according to inventive concept 41, wherein the sensor is configured to monitor the subject without contacting the subject or clothes the subject is wearing, and without viewing the subject or clothes the subject is wearing.

Inventive concept 50. The apparatus according to inventive concept 41, wherein the sensor is configured to monitor the subject without requiring compliance of the subject.

Inventive concept 51. The apparatus according to inventive concept 41, wherein the output includes a control signal to a room-climate-regulation device, and the computer processor is configured to generate the output by communicating the control signal to the room-climate-regulation device in response to the identified menstrual state.

Inventive concept 52. The apparatus according to inventive concept 41, wherein the computer processor is further configured, in response to identifying the subject's menstrual state, to identify that the subject is likely to experience premenstrual syndrome (PMS) in more than 0.5 days,
the computer processor being configured to generate the output in response thereto.

Inventive concept 53. The apparatus according to any one of inventive concepts 41-52, wherein the computer processor is configured to identify the menstrual state of the subject by identifying that the subject is likely to ovulate in less than 10 days.

Inventive concept 54. The apparatus according to inventive concept 53, wherein the computer processor is configured to identify the menstrual state of the subject by identifying that the subject is likely to ovulate in less than five days.

Inventive concept 55. The apparatus according to inventive concept 53, wherein the computer processor is configured to identify the menstrual state of the subject by identifying that the subject is likely to ovulate in more than 0.5 days.

Inventive concept 56. The apparatus according to inventive concept 53, wherein the computer processor is configured to derive a heart rate variability (HRV) signal from the sensor signal, and to identify the subject's menstrual state, in response thereto.

Inventive concept 57. The apparatus according to inventive concept 53, further comprising an input unit,
wherein the computer processor is configured to identify that the subject is likely to ovulate in less than 10 days by:
at least once, prior to currently receiving the sensor signal:
receiving, via the input unit, an input that is indicative of a phase of the subject's menstrual cycle, and
identifying an aspect of the sensor signal at a time at which the input was received,
in response to the input and the identified aspect of the sensor signal, learning an ovulation-prediction rule, and
using the ovulation-prediction rule to identify that the subject is likely to ovulate in less than 10 days, based upon the currently-received sensor signal.

Inventive concept 58. The apparatus according to any one of inventive concepts 41-52,
wherein the computer processor is further configured, in response to identifying the menstrual state of the subject, to identify that the subject is likely to experience premenstrual syndrome (PMS) in less than three days, the computer processor being configured to generate the output in response thereto.

Inventive concept 59. The apparatus according to inventive concept 58, wherein the computer processor is configured to derive a heart rate variability (HRV) signal from the sensor signal, and to identify the subject's menstrual state, in response thereto.

Inventive concept 60. The apparatus according to inventive concept 58, further comprising an input unit,
wherein the computer processor is configured to identify that the subject is likely to experience PMS in less than three days by:
at least once, prior to currently receiving the sensor signal:
receiving, via the input unit, an input that is indicative of an occurrence of PMS of the subject, and
identifying an aspect of the sensor signal at a time at which the input was received,
in response to the input and the identified aspect of the sensor signal, learning a PMS-prediction rule, and
using the PMS-prediction rule to identify that the subject is likely to experience PMS in less than three days, based upon the currently-received sensor signal.

Inventive concept 61. The apparatus according to any one of inventive concepts 41-52, wherein the computer processor is configured:
in response to the analyzing, to identify an aspect of the sensor signal selected from the group consisting of: a cardiac-related aspect of the sensor signal, and a respiration-related aspect of the sensor signal, and
to identify the menstrual state of the subject, in response to the identified aspect.

Inventive concept 62. The apparatus according to inventive concept 61, wherein the identified aspect of the sensor signal includes a respiratory rate of the subject, and wherein the computer processor is configured to identify the menstrual state of the subject by comparing the identified respiratory rate to a baseline respiratory rate.

Inventive concept 63. The apparatus according to inventive concept 61, further comprising an input unit,
wherein the identified aspect of the sensor signal is a currently-identified aspect of the sensor signal, and
wherein the computer processor is configured to identify the current phase of the menstrual cycle by:
at least once, prior to the identification of the currently-identified aspect of the sensor signal:
receiving, via the input unit, an input that is indicative of a phase of the subject's menstrual cycle, and
identifying an aspect of the sensor signal at a time at which the input was received,
in response to the input and the identified aspect of the sensor signal, learning a phase-identification rule, and
using the phase-identification rule to identify the menstrual state of the subject.

Inventive concept 64. The apparatus according to inventive concept 61, wherein the identified aspect of the sensor signal includes a heart rate variability (HRV) signal, the computer processor being configured to identify the menstrual state in response to the HRV signal.

Inventive concept 65. The apparatus according to inventive concept 64, wherein, in response to the HRV signal, the computer processor is configured to identify that the current phase of the subject's menstrual cycle is a late follicular phase.

Inventive concept 66. The apparatus according to inventive concept 65, wherein the computer processor is configured to identify that the current phase of the subject's menstrual cycle is the late follicular phase in response to an aspect of a component of a power spectrum of the HRV signal.

Inventive concept 67. The apparatus according to inventive concept 66, wherein the computer processor is configured to identify that the current phase of the subject's menstrual cycle is the late follicular phase by identifying that the component of the power spectrum of the HRV signal has an amplitude that exceeds a threshold.

Inventive concept 68. The apparatus according to inventive concept 66, wherein the component of the power spectrum of the HRV signal lies between 0.1 and 0.5 Hz, the computer processor being configured to identify that the current phase of the subject's menstrual cycle is the late follicular phase in response to an aspect of the component of the power spectrum.

Inventive concept 69. The apparatus according to any one of inventive concepts 41-52, wherein the identified aspect of the sensor signal includes a heart rate of the subject, and wherein the computer processor is configured to identify the menstrual state of the subject by comparing the identified heart rate to a baseline heart rate.

Inventive concept 70. The apparatus according to inventive concept 69, wherein the computer processor is configured, in response to the comparing, to:
ascertain that the identified heart rate is greater than the baseline heart rate; and in response thereto, identify the menstrual state of the subject by identifying that the subject is currently within a given amount of time of ovulation of the subject.

Inventive concept 71. The apparatus according to inventive concept 70, wherein the computer processor is configured to identify that the subject is currently within the given amount of time of ovulation of the subject by identifying that less than the given amount of time has transpired since the subject ovulated.

Inventive concept 72. The apparatus according to inventive concept 70, wherein the computer processor is configured, in response to ascertaining that the identified heart rate is greater than the baseline heart rate, to identify that the subject is currently within less than two days of ovulation of the subject.

Inventive concept 73. The apparatus according to inventive concept 70, wherein the computer processor is configured to identify that the subject is currently within the given amount of time of ovulation of the subject in response to the identified heart rate being less than five heartbeats-per-minute greater than the baseline heart rate.

Inventive concept 74. The apparatus according to inventive concept 61, wherein the sensor is configured to monitor the subject during a sleeping session of the subject.

Inventive concept 75. The apparatus according to inventive concept 74,
    wherein the computer processor is configured to analyze the sensor signal by identifying an aspect of the sensor signal that is exhibited at least two hours from a beginning of the sleeping session, and
    wherein the computer processor is configured to identify the menstrual state of the subject (i) in response to the aspect of the sensor signal that is exhibited at least two hours from the beginning of the sleeping session, and (ii) substantially not in response to any aspect of the sensor signal that is exhibited less than two hours from the beginning of the sleeping session.

Inventive concept 76. The apparatus according to inventive concept 74,
    wherein the computer processor is further configured, in response to analyzing the sensor signal, to determine a level of motion of the subject,
    wherein the computer processor is configured to analyze the sensor signal by identifying an aspect of the sensor signal that is exhibited while the level of motion does not exceed a threshold, and
    wherein the computer processor is configured to identify the menstrual state of the subject (i) in response to the aspect of the sensor signal that is exhibited while the level of motion does not exceed the threshold, and (ii) substantially not in response to any aspect of the sensor signal that is exhibited while the level of motion exceeds the threshold.

Inventive concept 77. The apparatus according to inventive concept 74,
    wherein the computer processor is further configured, in response to analyzing the sensor signal, to identify a sleep stage of the subject during the sleeping session,
    wherein the computer processor is configured to analyze the sensor signal by identifying an aspect of the sensor signal that is exhibited while the identified sleep stage is a particular sleep stage, and
    wherein the computer processor is configured to identify the menstrual state of the subject (i) in response to the aspect of the sensor signal that is exhibited while the identified sleep stage is the particular sleep stage, and (ii) substantially not in response to any aspect of the sensor signal that is exhibited while the identified sleep stage is not the particular sleep stage.

Inventive concept 78. The apparatus according to inventive concept 77, wherein the particular sleep stage is a slow-wave sleep stage.

Inventive concept 79. The apparatus according to inventive concept 77, wherein the particular sleep stage is a rapid-eye-movement sleep stage.

Inventive concept 80. The apparatus according to inventive concept 79, wherein the identified aspect of the sensor signal includes a heart rate variability (HRV) signal, the computer processor being configured to identify the menstrual state of the subject in response to the HRV signal that is exhibited while the identified sleep stage is the particular sleep stage.

Inventive concept 81. The apparatus according to inventive concept 74,
    wherein the computer processor is further configured, in response to analyzing the sensor signal, to identify an end of a chronologically-first sleep cycle of the subject during the sleeping session,
    wherein the computer processor is configured to analyze the sensor signal by identifying an aspect of the sensor signal that is exhibited following the end of the chronologically-first sleep cycle, and
    wherein the computer processor is configured to identify the menstrual state of the subject (i) in response to the aspect of the sensor signal that is exhibited following the end of the chronologically-first sleep cycle, and (ii) substantially not in response to any aspect of the sensor signal that is exhibited before the end of the chronologically-first sleep cycle.

Inventive concept 82. The apparatus according to inventive concept 81,
    wherein the computer processor is further configured, in response to analyzing the sensor signal, to identify an end of a chronologically-second sleep cycle of the subject during the sleeping session,
    wherein the computer processor is configured to analyze the sensor signal by identifying an aspect of the sensor signal that is exhibited following the end of the chronologically-second sleep cycle, and
    wherein the computer processor is configured to identify the menstrual state of the subject (i) in response to the aspect of the sensor signal that is exhibited following the end of the chronologically-second sleep cycle, and (ii) substantially not in response to any aspect of the sensor signal that is exhibited before the end of the chronologically-second sleep cycle.

Inventive concept 83. Apparatus for monitoring a female subject, the apparatus comprising:
    a sensor, configured to monitor the subject and to generate a sensor signal in response to the monitoring; and
    a computer processor, configured to:
        receive the sensor signal,
        derive a cardiac-related aspect of the sensor signal by analyzing the sensor signal,
        based upon the derived cardiac-related aspect of the sensor signal, identify a menstrual state of the subject, and
        generate an output in response thereto.

Inventive concept 84. The apparatus according to inventive concept 83, wherein the computer processor is configured to identify the subject's menstrual state without determining a temperature of the subject.

Inventive concept 85. The apparatus according to inventive concept 83, wherein the sensor is configured not to measure a temperature of the subject.

Inventive concept 86. The apparatus according to inventive concept 83, wherein the sensor is configured to monitor the subject without having a direct line of sight of the subject or clothes the subject is wearing.

Inventive concept 87. The apparatus according to inventive concept 83, wherein the sensor is configured to monitor the subject without requiring compliance of the subject.

Inventive concept 88. The apparatus according to inventive concept 83, wherein the computer processor is configured to identify the subject's menstrual state by identifying a current menstrual state of the subject.

Inventive concept 89. The apparatus according to inventive concept 83, wherein the computer processor is configured to identify the subject's menstrual state by predicting an occurrence of a future menstrual state of the subject.

Inventive concept 90. The apparatus according to inventive concept 83, wherein the sensor is configured to be disposed upon or within a bed of the subject, and is configured to monitor the subject automatically while the subject is in her bed.

Inventive concept 91. The apparatus according to inventive concept 83, wherein the computer processor is configured to identify the menstrual state of the subject, using a machine-learning algorithm.

Inventive concept 92. The apparatus according to inventive concept 83, wherein the sensor is configured to monitor the subject without contacting the subject or clothes the subject is wearing, and without viewing the subject or clothes the subject is wearing.

Inventive concept 93. The apparatus according to inventive concept 83, wherein the output includes a control signal to a room-climate-regulation device, and the computer processor is configured to generate the output by communicating the control signal to the room-climate-regulation device in response to the identified menstrual state.

Inventive concept 94. The apparatus according to inventive concept 83, wherein the computer processor is further configured, in response to identifying the subject's menstrual state, to identify that the subject is likely to experience premenstrual syndrome (PMS) in more than 0.5 days,
  the computer processor being configured to generate the output in response thereto.

Inventive concept 95. The apparatus according to inventive concept 83, further comprising an input unit,
  wherein the computer processor is configured to identify menstrual state of the subject by:
    at least once, prior to currently receiving the sensor signal:
      receiving, via the input unit, an input that is indicative of a phase of the subject's menstrual cycle, and
      identifying an aspect of the sensor signal at a time at which the input was received,
    in response to the input and the identified aspect of the sensor signal, learning a phase-identification rule, and
    using the phase-identification rule to identify a current phase of the subject's menstrual cycle, based upon the currently-received sensor signal.

Inventive concept 96. The apparatus according to any one of inventive concepts 83-95, wherein the computer processor is configured to identify the menstrual state of the subject by identifying that the subject is likely to ovulate in less than 10 days.

Inventive concept 97. The apparatus according to inventive concept 96, wherein the computer processor is configured to identify the menstrual state of the subject by identifying that the subject is likely to ovulate in less than five days.

Inventive concept 98. The apparatus according to inventive concept 96, wherein the computer processor is configured to identify the menstrual state of the subject by identifying that the subject is likely to ovulate in more than 0.5 days.

Inventive concept 99. The apparatus according to inventive concept 96, wherein the computer processor is configured to derive a heart rate variability (HRV) signal from the sensor signal, and to identify the subject's menstrual state, in response thereto.

Inventive concept 100. The apparatus according to inventive concept 96, further comprising an input unit,
  wherein the computer processor is configured to identify that the subject is likely to ovulate in less than 10 days by:
    at least once, prior to currently receiving the sensor signal:
      receiving, via the input unit, an input that is indicative of a phase of the subject's menstrual cycle, and
      identifying an aspect of the sensor signal at a time at which the input was received,
    in response to the input and the identified aspect of the sensor signal, learning an ovulation-prediction rule, and
    using the ovulation-prediction rule to identify that the subject is likely to ovulate in less than 10 days, based upon the currently-received sensor signal.

Inventive concept 101. The apparatus according to any one of inventive concepts 83-95,
  wherein the computer processor is further configured, in response to identifying the menstrual state of the subject, to identify that the subject is likely to experience premenstrual syndrome (PMS) in less than three days,
    the computer processor being configured to generate the output in response thereto.

Inventive concept 102. The apparatus according to inventive concept 101, wherein the computer processor is configured to derive a heart rate variability (HRV) signal from the sensor signal, and to identify the subject's menstrual state, in response thereto.

Inventive concept 103. The apparatus according to inventive concept 101, further comprising an input unit,
  wherein the computer processor is configured to identify that the subject is likely to experience PMS in less than three days by:
    at least once, prior to currently receiving the sensor signal:
      receiving, via the input unit, an input that is indicative of an occurrence of PMS of the subject, and
      identifying an aspect of the sensor signal at a time at which the input was received,
    in response to the input and the identified aspect of the sensor signal, learning a PMS-prediction rule, and
    using the PMS-prediction rule to identify that the subject is likely to experience PMS in less than three days, based upon the currently-received sensor signal.

Inventive concept 104. The apparatus according to any one of inventive concepts 83-95, wherein the cardiac-related aspect of the sensor signal includes a heart rate variability (HRV) signal, the computer processor being configured to identify the menstrual state of the subject in response to the HRV signal.

Inventive concept 105. The apparatus according to inventive concept 104, wherein, in response to the HRV signal, the computer processor is configured to identify that a current phase of the subject's menstrual cycle is a late follicular phase.

Inventive concept 106. The apparatus according to inventive concept 105, wherein the computer processor is configured to identify that the current phase of the subject's menstrual cycle is the late follicular phase in response to an aspect of a component of a power spectrum of the HRV signal.

Inventive concept 107. The apparatus according to inventive concept 106, wherein the computer processor is configured to identify that the current phase of the subject's menstrual cycle is the late follicular phase by identifying that the component of the power spectrum of the HRV signal has an amplitude that exceeds a threshold.

Inventive concept 108. The apparatus according to inventive concept 106, wherein the component of the power spectrum of the HRV signal lies between 0.1 and 0.5 Hz, the computer processor being configured to identify that the current phase of the subject's menstrual cycle is the late follicular phase in response to an aspect of the component of the power spectrum.

Inventive concept 109. The apparatus according to any one of inventive concepts 83-95, wherein the cardiac-related aspect of the sensor signal includes a heart rate of the subject, and wherein the computer processor is configured to identify a current phase of the menstrual cycle of the subject by comparing the derived heart rate to a baseline heart rate.

Inventive concept 110. The apparatus according to inventive concept 109, wherein the computer processor is configured, in response to the comparing, to:
    ascertain that the derived heart rate is greater than the baseline heart rate; and
    in response thereto, identify the current phase of the menstrual cycle of the subject by identifying that the subject is currently within a given amount of time of ovulation of the subject.

Inventive concept 111. The apparatus according to inventive concept 110, wherein the computer processor is configured to identify that the subject is currently within the given amount of time of ovulation of the subject by identifying that less than the given amount of time has transpired since the subject ovulated.

Inventive concept 112. The apparatus according to inventive concept 110, wherein the computer processor is configured, in response to ascertaining that the identified heart rate is greater than the baseline heart rate, to identify that the subject is currently within less than two days of ovulation of the subject.

Inventive concept 113. The apparatus according to inventive concept 110, wherein the computer processor is configured to identify that the subject is currently within the given amount of time of ovulation of the subject in response to the derived heart rate being less than five heartbeats-per-minute greater than the baseline heart rate.

Inventive concept 114. The apparatus according to any one of inventive concepts 83-95, wherein the sensor is configured to monitor the subject during a sleeping session of the subject.

Inventive concept 115. The apparatus according to inventive concept 114,
    wherein the computer processor is configured to derive the cardiac-related aspect of the sensor signal by identifying an aspect of the sensor signal that is exhibited at least two hours from a beginning of the sleeping session, and
    wherein the computer processor is configured to identify the menstrual state of the subject (i) in response to the cardiac-related aspect of the sensor signal that is exhibited at least two hours from the beginning of the sleeping session, and (ii) substantially not in response to any aspect of the sensor signal that is exhibited less than two hours from the beginning of the sleeping session.

Inventive concept 116. The apparatus according to inventive concept 114,
    wherein the computer processor is further configured, in response to analyzing the sensor signal, to determine a level of motion of the subject,
    wherein the computer processor is configured to derive the cardiac-related aspect of the sensor signal by deriving the cardiac-related aspect of the sensor signal that is exhibited while the level of motion does not exceed a threshold, and
    wherein the computer processor is configured to identify the menstrual state of the subject (i) in response to the cardiac-related aspect of the sensor signal that is exhibited while the level of motion does not exceed the threshold, and (ii) substantially not in response to any aspect of the sensor signal that is exhibited while the level of motion exceeds the threshold.

Inventive concept 117. The apparatus according to inventive concept 114,
    wherein the computer processor is further configured, in response to analyzing the sensor signal, to identify a sleep stage of the subject during the sleeping session,
    wherein the computer processor is configured to derive the cardiac-related aspect of the sensor signal by deriving a cardiac-related aspect of the sensor signal that is exhibited while the identified sleep stage is a particular sleep stage, and
    wherein the computer processor is configured to identify the menstrual state of the subject (i) in response to the cardiac-related aspect of the sensor signal that is exhibited while the identified sleep stage is the particular sleep stage, and (ii) substantially not in response to any aspect of the sensor signal that is exhibited while the identified sleep stage is not the particular sleep stage.

Inventive concept 118. The apparatus according to inventive concept 117, wherein the particular sleep stage is a slow-wave sleep stage.

Inventive concept 119. The apparatus according to inventive concept 117, wherein the particular sleep stage is a rapid-eye-movement sleep stage.

Inventive concept 120. The apparatus according to inventive concept 119, wherein the cardiac-related aspect of the sensor signal includes a heart rate variability (HRV) signal,
    the computer processor being configured to identify the current phase of the menstrual cycle of the subject in response to the HRV signal that is exhibited while the identified sleep stage is the particular sleep stage.

Inventive concept 121. The apparatus according to inventive concept 114,
    wherein the computer processor is further configured, in response to analyzing the sensor signal, to identify an end of a chronologically-first sleep cycle of the subject during the sleeping session,
    wherein the computer processor is configured to derive the cardiac-related aspect of the sensor signal by deriving a cardiac-related aspect of the sensor signal that is exhibited following the end of the chronologically-first sleep cycle, and wherein the computer processor is configured to identify the menstrual state of the subject (i) in response to the cardiac-related aspect of the sensor signal that is exhibited following the end of the chronologically-first sleep cycle, and (ii) substantially not in response to any aspect of the sensor signal that is exhibited before the end of the chronologically-first sleep cycle.

Inventive concept 122. The apparatus according to inventive concept 121,
wherein the computer processor is further configured, in response to analyzing the sensor signal, to identify an end of a chronologically-second sleep cycle of the subject during the sleeping session,
wherein the computer processor is configured to derive the cardiac-related aspect of the sensor signal by deriving a cardiac-related aspect of the sensor signal that is exhibited following the end of the chronologically-second sleep cycle, and
wherein the computer processor is configured to identify the menstrual state of the subject (i) in response to the cardiac-related aspect of the sensor signal that is exhibited following the end of the chronologically-second sleep cycle, and (ii) substantially not in response to any aspect of the sensor signal that is exhibited before the end of the chronologically-second sleep cycle.

Inventive concept 123. Apparatus for monitoring a female subject, the apparatus comprising:
a sensor, configured to monitor the subject without requiring compliance of the subject, and to generate a sensor signal in response to the monitoring; and
a computer processor, configured to:
receive the sensor signal,
analyze the sensor signal,
in response to the analyzing, identify whether the subject is in a pregnant state or a non-pregnant state, and
generate an output in response thereto.

Inventive concept 124. The apparatus according to inventive concept 123, wherein the computer processor is configured to identify whether the subject is in the pregnant state or the non-pregnant state without determining a temperature of the subject.

Inventive concept 125. The apparatus according to inventive concept 123, wherein the sensor is configured not to measure a temperature of the subject.

Inventive concept 126. The apparatus according to inventive concept 123, wherein the sensor is configured to monitor the subject without having a direct line of sight of the subject or clothes the subject is wearing.

Inventive concept 127. The apparatus according to inventive concept 123, wherein the sensor is configured to be disposed upon or within a bed of the subject, and is configured to monitor the subject automatically while the subject is in her bed.

Inventive concept 128. The apparatus according to inventive concept 123, wherein the sensor is configured to monitor the subject without contacting the subject or clothes the subject is wearing, and without viewing the subject or clothes the subject is wearing.

Inventive concept 129. The apparatus according to inventive concept 123, wherein the output includes a control signal to a room-climate-regulation device, and the computer processor is configured to generate the output by communicating the control signal to the room-climate-regulation device in response to the identified state.

Inventive concept 130. The apparatus according to inventive concept 123, wherein the computer processor is configured to identify whether the subject is in the pregnant state or the non-pregnant state, using a machine-learning algorithm.

Inventive concept 131. The apparatus according to any one of inventive concepts 123-130, wherein the computer processor is configured:
in response to the analyzing, to identify an aspect of the sensor signal selected from the group consisting of: a cardiac-related aspect of the sensor signal, and a respiration-related aspect of the sensor signal, and to identify whether the subject is in the pregnant state or the non-pregnant state, in response to the identified aspect.

Inventive concept 132. The apparatus according to inventive concept 131, further comprising an input unit,
wherein the identified aspect of the sensor signal is a currently-identified aspect of the sensor signal, and
wherein the computer processor is configured to identify whether the subject is in the pregnant state or the non-pregnant state by:
at least once, prior to the identification of the currently-identified aspect of the sensor signal:
receiving, via the input unit, an input that is indicative of whether the subject is pregnant, and
identifying an aspect of the sensor signal at a time at which the input was received,
in response to the input and the identified aspect of the sensor signal, learning a pregnancy-identification rule, and
using the pregnancy-identification rule to identify whether the subject is in the pregnant state or the non-pregnant state.

Inventive concept 133. The apparatus according to inventive concept 131,
wherein the identified aspect of the sensor signal includes a respiratory rate of the subject, and
wherein the computer processor is configured to (i) identify that the subject is pregnant by ascertaining that the identified respiratory rate is not lower than a baseline respiratory rate, and (ii) identify that the subject is not pregnant by ascertaining that the identified respiratory rate is lower than the baseline respiratory rate.

Inventive concept 134. The apparatus according to inventive concept 131,
wherein the identified aspect of the sensor signal includes a heart rate of the subject, and
wherein the computer processor is configured to (i) identify that the subject is pregnant by ascertaining that the identified heart rate is not lower than a baseline heart rate, and (ii) identify that the subject is not pregnant by ascertaining that the identified heart rate is lower than the baseline heart rate.

Inventive concept 135. The apparatus according to inventive concept 134,
wherein the identified heart rate of the subject is a currently-identified heart rate, and
wherein the computer processor is further configured to identify the baseline heart rate in response to a previously-identified heart rate of the subject that was identified less than fourteen days prior to identifying the currently-identified heart rate.

Inventive concept 136. Apparatus for monitoring a female subject, the apparatus comprising:
a sensor, configured to monitor the subject without requiring compliance of the subject, and to generate a sensor signal in response to the monitoring; and a computer processor, configured to:
  receive the sensor signal,
  analyze the sensor signal,
  in response to the analyzing, identify a menstrual state of the subject, and
  generate an output in response thereto.

Inventive concept 137. The apparatus according to inventive concept 136, wherein the computer processor is configured to identify the subject's menstrual state without determining a temperature of the subject.

Inventive concept 138. The apparatus according to inventive concept 136, wherein the sensor is configured not to measure a temperature of the subject.

Inventive concept 139. The apparatus according to inventive concept 136, wherein the sensor is configured to monitor the subject without having a direct line of sight of the subject or clothes the subject is wearing.

Inventive concept 140. The apparatus according to inventive concept 136, wherein the computer processor is configured to identify the subject's menstrual state by identifying a current menstrual state of the subject.

Inventive concept 141. The apparatus according to inventive concept 136, wherein the computer processor is configured to identify the subject's menstrual state by predicting an occurrence of a future menstrual state of the subject.

Inventive concept 142. The apparatus according to inventive concept 136, wherein the sensor is configured to be disposed upon or within a bed of the subject, and is configured to monitor the subject automatically while the subject is in her bed.

Inventive concept 143. The apparatus according to inventive concept 136, wherein the computer processor is configured to identify the menstrual state of the subject, using a machine-learning algorithm.

Inventive concept 144. The apparatus according to inventive concept 136, wherein the sensor is configured to monitor the subject without contacting the subject or clothes the subject is wearing, and without viewing the subject or clothes the subject is wearing.

Inventive concept 145. The apparatus according to inventive concept 136, wherein the output includes a control signal to a room-climate-regulation device, and the computer processor is configured to generate the output by communicating the control signal to the room-climate-regulation device in response to the identified menstrual state.

Inventive concept 146. The apparatus according to inventive concept 136, wherein the computer processor is further configured, in response to identifying the subject's menstrual state, to identify that the subject is likely to experience premenstrual syndrome (PMS) in more than 0.5 days,
  the computer processor being configured to generate the output in response thereto.

Inventive concept 147. The apparatus according to any one of inventive concepts 136-146, wherein the computer processor is configured to identify the menstrual state of the subject by identifying that the subject is likely to ovulate in less than 10 days.

Inventive concept 148. The apparatus according to inventive concept 147, wherein the computer processor is configured to identify the menstrual state of the subject by identifying that the subject is likely to ovulate in less than five days.

Inventive concept 149. The apparatus according to inventive concept 147, wherein the computer processor is configured to identify the menstrual state of the subject by identifying that the subject is likely to ovulate in more than 0.5 days.

Inventive concept 150. The apparatus according to inventive concept 147, wherein the computer processor is configured to derive a heart rate variability (HRV) signal from the sensor signal, and to identify the subject's menstrual state, in response thereto.

Inventive concept 151. The apparatus according to inventive concept 147, further comprising an input unit,
  wherein the computer processor is configured to identify that the subject is likely to ovulate in less than 10 days by:
    at least once, prior to currently receiving the sensor signal:
      receiving, via the input unit, an input that is indicative of a phase of the subject's menstrual cycle, and
      identifying an aspect of the sensor signal at a time at which the input was received,
    in response to the input and the identified aspect of the sensor signal, learning an ovulation-prediction rule, and
    using the ovulation-prediction rule to identify that the subject is likely to ovulate in less than 10 days, based upon the currently-received sensor signal.

Inventive concept 152. The apparatus according to any one of inventive concepts 136-146,
  wherein the computer processor is further configured, in response to identifying the menstrual state of the subject, to identify that the subject is likely to experience premenstrual syndrome (PMS) in less than three days,
  the computer processor being configured to generate the output in response thereto.

Inventive concept 153. The apparatus according to inventive concept 152, wherein the computer processor is configured to derive a heart rate variability (HRV) signal from the sensor signal, and to identify the subject's menstrual state, in response thereto.

Inventive concept 154. The apparatus according to inventive concept 152, further comprising an input unit,
  wherein the computer processor is configured to identify that the subject is likely to experience PMS in less than three days by:
    at least once, prior to currently receiving the sensor signal:
      receiving, via the input unit, an input that is indicative of an occurrence of PMS of the subject, and
      identifying an aspect of the sensor signal at a time at which the input was received,
    in response to the input and the identified aspect of the sensor signal, learning a PMS-prediction rule, and
    using the PMS-prediction rule to identify that the subject is likely to experience PMS in less than three days, based upon the currently-received sensor signal.

Inventive concept 155. The apparatus according to any one of inventive concepts 136-146, wherein the computer processor is configured:
  in response to the analyzing, to identify an aspect of the sensor signal selected from the group consisting of: a cardiac-related aspect of the sensor signal, and a respiration-related aspect of the sensor signal, and
  to identify the menstrual state of the subject, in response to the identified aspect.

Inventive concept 156. The apparatus according to inventive concept 155, wherein the identified aspect of the sensor signal includes a respiratory rate of the subject, and wherein the computer processor is configured to identify the menstrual state of the subject by comparing the identified respiratory rate to a baseline respiratory rate.

Inventive concept 157. The apparatus according to inventive concept 155, further comprising an input unit,
wherein the identified aspect of the sensor signal is a currently-identified aspect of the sensor signal, and
wherein the computer processor is configured to identify the current phase of the menstrual cycle by:
at least once, prior to the identification of the currently-identified aspect of the sensor signal:
receiving, via the input unit, an input that is indicative of a phase of the subject's menstrual cycle, and
identifying an aspect of the sensor signal at a time at which the input was received,
in response to the input and the identified aspect of the sensor signal, learning a phase-identification rule, and
using the phase-identification rule to identify the menstrual state of the subject.

Inventive concept 158. The apparatus according to inventive concept 155, wherein the identified aspect of the sensor signal includes a heart rate variability (HRV) signal, the computer processor being configured to identify the menstrual state in response to the HRV signal.

Inventive concept 159. The apparatus according to inventive concept 158, wherein, in response to the HRV signal, the computer processor is configured to identify that the current phase of the subject's menstrual cycle is a late follicular phase.

Inventive concept 160. The apparatus according to inventive concept 159, wherein the computer processor is configured to identify that the current phase of the subject's menstrual cycle is the late follicular phase in response to an aspect of a component of a power spectrum of the HRV signal.

Inventive concept 161. The apparatus according to inventive concept 160, wherein the computer processor is configured to identify that the current phase of the subject's menstrual cycle is the late follicular phase by identifying that the component of the power spectrum of the HRV signal has an amplitude that exceeds a threshold.

Inventive concept 162. The apparatus according to inventive concept 160, wherein the component of the power spectrum of the HRV signal lies between 0.1 and 0.5 Hz, the computer processor being configured to identify that the current phase of the subject's menstrual cycle is the late follicular phase in response to an aspect of the component of the power spectrum.

Inventive concept 163. The apparatus according to inventive concept 155, wherein the identified aspect of the sensor signal includes a heart rate of the subject, and wherein the computer processor is configured to identify the menstrual state of the subject by comparing the identified heart rate to a baseline heart rate.

Inventive concept 164. The apparatus according to inventive concept 163, wherein the computer processor is configured, in response to the comparing, to:
ascertain that the identified heart rate is greater than the baseline heart rate; and
in response thereto, identify the menstrual state of the subject by identifying that the subject is currently within a given amount of time of ovulation of the subject.

Inventive concept 165. The apparatus according to inventive concept 164, wherein the computer processor is configured to identify that the subject is currently within the given amount of time of ovulation of the subject by identifying that less than the given amount of time has transpired since the subject ovulated.

Inventive concept 166. The apparatus according to inventive concept 164, wherein the computer processor is configured, in response to ascertaining that the identified heart rate is greater than the baseline heart rate, to identify that the subject is currently within less than two days of ovulation of the subject.

Inventive concept 167. The apparatus according to inventive concept 164, wherein the computer processor is configured to identify that the subject is currently within the given amount of time of ovulation of the subject in response to the identified heart rate being less than five heartbeats-per-minute greater than the baseline heart rate.

Inventive concept 168. The apparatus according to inventive concept 155, wherein the sensor is configured to monitor the subject during a sleeping session of the subject.

Inventive concept 169. The apparatus according to inventive concept 168,
wherein the computer processor is configured to analyze the sensor signal by identifying an aspect of the sensor signal that is exhibited at least two hours from a beginning of the sleeping session, and
wherein the computer processor is configured to identify the menstrual state of the subject (i) in response to the aspect of the sensor signal that is exhibited at least two hours from the beginning of the sleeping session, and (ii) substantially not in response to any aspect of the sensor signal that is exhibited less than two hours from the beginning of the sleeping session.

Inventive concept 170. The apparatus according to inventive concept 168,
wherein the computer processor is further configured, in response to analyzing the sensor signal, to determine a level of motion of the subject,
wherein the computer processor is configured to analyze the sensor signal by identifying an aspect of the sensor signal that is exhibited while the level of motion does not exceed a threshold, and
wherein the computer processor is configured to identify the menstrual state of the subject (i) in response to the aspect of the sensor signal that is exhibited while the level of motion does not exceed the threshold, and (ii) substantially not in response to any aspect of the sensor signal that is exhibited while the level of motion exceeds the threshold.

Inventive concept 171. The apparatus according to inventive concept 168,
wherein the computer processor is further configured, in response to analyzing the sensor signal, to identify a sleep stage of the subject during the sleeping session,
wherein the computer processor is configured to analyze the sensor signal by identifying an aspect of the sensor signal that is exhibited while the identified sleep stage is a particular sleep stage, and
wherein the computer processor is configured to identify the menstrual state of the subject (i) in response to the aspect of the sensor signal that is exhibited while the identified sleep stage is the particular sleep stage, and (ii) substantially not in response to any aspect of the sensor signal that is exhibited while the identified sleep stage is not the particular sleep stage.

Inventive concept 172. The apparatus according to inventive concept 171, wherein the particular sleep stage is a slow-wave sleep stage.

Inventive concept 173. The apparatus according to inventive concept 171, wherein the particular sleep stage is a rapid-eye-movement sleep stage.

Inventive concept 174. The apparatus according to inventive concept 171, wherein the identified aspect of the sensor signal includes a heart rate variability (HRV) signal, the computer processor being configured to identify the menstrual state of the subject in response to the HRV signal that is exhibited while the identified sleep stage is the particular sleep stage.

Inventive concept 175. The apparatus according to inventive concept 168,
wherein the computer processor is further configured, in response to analyzing the sensor signal, to identify an end of a chronologically-first sleep cycle of the subject during the sleeping session,
wherein the computer processor is configured to analyze the sensor signal by identifying an aspect of the sensor signal that is exhibited following the end of the chronologically-first sleep cycle, and
wherein the computer processor is configured to identify the menstrual state of the subject (i) in response to the aspect of the sensor signal that is exhibited following the end of the chronologically-first sleep cycle, and (ii) substantially not in response to any aspect of the sensor signal that is exhibited before the end of the chronologically-first sleep cycle.

Inventive concept 176. The apparatus according to inventive concept 175,
wherein the computer processor is further configured, in response to analyzing the sensor signal, to identify an end of a chronologically-second sleep cycle of the subject during the sleeping session,
wherein the computer processor is configured to analyze the sensor signal by identifying an aspect of the sensor signal that is exhibited following the end of the chronologically-second sleep cycle, and
wherein the computer processor is configured to identify the menstrual state of the subject (i) in response to the aspect of the sensor signal that is exhibited following the end of the chronologically-second sleep cycle, and (ii) substantially not in response to any aspect of the sensor signal that is exhibited before the end of the chronologically-second sleep cycle.

Inventive concept 177. Apparatus for monitoring a female subject, the apparatus comprising:
a sensor, configured to monitor the subject and to generate a sensor signal in response to the monitoring; and
a computer processor, configured to:
receive the sensor signal,
derive a cardiac-related aspect of the sensor signal by analyzing the sensor signal,
based upon the derived cardiac-related aspect of the sensor signal, identify whether the subject is in a pregnant state or a non-pregnant state, and
generate an output in response thereto.

Inventive concept 178. The apparatus according to inventive concept 177, wherein the computer processor is configured to identify whether the subject is in the pregnant state or the non-pregnant state without determining a temperature of the subject.

Inventive concept 179. The apparatus according to inventive concept 177, wherein the sensor is configured not to measure a temperature of the subject.

Inventive concept 180. The apparatus according to inventive concept 177, wherein the sensor is configured to monitor the subject without having a direct line of sight of the subject or clothes the subject is wearing.

Inventive concept 181. The apparatus according to inventive concept 177, wherein the sensor is configured to monitor the subject without requiring compliance of the subject.

Inventive concept 182. The apparatus according to inventive concept 177, wherein the sensor is configured to be disposed upon or within a bed of the subject, and is configured to monitor the subject automatically while the subject is in her bed.

Inventive concept 183. The apparatus according to inventive concept 177, wherein the sensor is configured to monitor the subject without contacting the subject or clothes the subject is wearing, and without viewing the subject or clothes the subject is wearing.

Inventive concept 184. The apparatus according to inventive concept 177, wherein the output includes a control signal to a room-climate-regulation device, and the computer processor is configured to generate the output by communicating the control signal to the room-climate-regulation device in response to the identified state.

Inventive concept 185. The apparatus according to inventive concept 177, wherein, based upon the derived cardiac-related aspect, the computer processor is configured to identify whether the subject is in the pregnant state or the non-pregnant state, using a machine-learning algorithm.

Inventive concept 186. The apparatus according to any one of inventive concepts 177-185, wherein the computer processor is configured to derive the cardiac-related aspect of the sensor signal, by deriving a heart rate of the subject, and the computer processor is configured to (i) identify that the subject is pregnant by ascertaining that a derived heart rate is not lower than a baseline heart rate, and (ii) identify that the subject is not pregnant by ascertaining that the derived heart rate is lower than the baseline heart rate.

Inventive concept 187. The apparatus according to inventive concept 186,
wherein the derived heart rate of the subject is a current heart rate of the subject, and
wherein the computer processor is further configured to identify the baseline heart rate in response to a previously-identified heart rate of the subject that was identified less than fourteen days prior to deriving the currently-derived heart rate.

Inventive concept 188. Apparatus for monitoring a female subject, the apparatus comprising:
a sensor, configured to monitor the subject without contacting the subject or clothes the subject is wearing, and without viewing the subject or clothes the subject is wearing, and to generate a sensor signal in response to the monitoring; and
a computer processor, configured to:
receive the sensor signal,
analyze the sensor signal,
in response to the analyzing, identify whether the subject is in a pregnant state or a non-pregnant state, and
generate an output in response thereto.

Inventive concept 189. The apparatus according to inventive concept 188, wherein the computer processor is configured to identify whether the subject is in the pregnant state or the non-pregnant state without determining a temperature of the subject.

Inventive concept 190. The apparatus according to inventive concept 188, wherein the sensor is configured not to measure a temperature of the subject.

Inventive concept 191. The apparatus according to inventive concept 188, wherein the sensor is configured to monitor the subject without having a direct line of sight of the subject or clothes the subject is wearing.

Inventive concept 192. The apparatus according to inventive concept 188, wherein the sensor is configured to be disposed upon or within a bed of the subject, and is configured to monitor the subject automatically while the subject is in her bed.

Inventive concept 193. The apparatus according to inventive concept 188, wherein the output includes a control signal to a room-climate-regulation device, and the computer processor is configured to generate the output by communicating the control signal to the room-climate-regulation device in response to the identified state.

Inventive concept 194. The apparatus according to inventive concept 188, wherein the computer processor is configured to identify whether the subject is in the pregnant state or the non-pregnant state, using a machine-learning algorithm.

Inventive concept 195. The apparatus according to any one of inventive concepts 188-194, wherein the computer processor is configured:
   in response to the analyzing, to identify an aspect of the sensor signal selected from the group consisting of: a cardiac-related aspect of the sensor signal, and a respiration-related aspect of the sensor signal, and
   to identify whether the subject is in the pregnant state or the non-pregnant state, in response to the identified aspect.

Inventive concept 196. The apparatus according to inventive concept 195, further comprising an input unit,
   wherein the identified aspect of the sensor signal is a currently-identified aspect of the sensor signal, and
   wherein the computer processor is configured to identify whether the subject is in the pregnant state or the non-pregnant state by:
      at least once, prior to the identification of the currently-identified aspect of the sensor signal:
         receiving, via the input unit, an input that is indicative of whether the subject is pregnant, and
         identifying an aspect of the sensor signal at a time at which the input was received,
      in response to the input and the identified aspect of the sensor signal, learning a pregnancy-identification rule, and
      using the pregnancy-identification rule to identify whether the subject is in the pregnant state or the non-pregnant state.

Inventive concept 197. The apparatus according to inventive concept 195,
   wherein the identified aspect of the sensor signal includes a respiratory rate of the subject, and
   wherein the computer processor is configured to (i) identify that the subject is pregnant by ascertaining that the identified respiratory rate is not lower than a baseline respiratory rate, and (ii) identify that the subject is not pregnant by ascertaining that the identified respiratory rate is lower than the baseline respiratory rate.

Inventive concept 198. The apparatus according to inventive concept 195,
   wherein the identified aspect of the sensor signal includes a heart rate of the subject, and
   wherein the computer processor is configured to (i) identify that the subject is pregnant by ascertaining that the identified heart rate is not lower than a baseline heart rate, and (ii) identify that the subject is not pregnant by ascertaining that the identified heart rate is lower than the baseline heart rate.

Inventive concept 199. The apparatus according to inventive concept 198,
   wherein the identified heart rate of the subject is a currently-identified heart rate, and
   wherein the computer processor is further configured to identify the baseline heart rate in response to a previously-identified heart rate of the subject that was identified less than fourteen days prior to identifying the currently-identified heart rate.

Inventive concept 200. Apparatus for monitoring a female subject and for use with a bed, the apparatus comprising:
   a sensor configured to be disposed upon or within the bed, to automatically monitor the subject while the subject is in the bed, and to generate a sensor signal in response to the monitoring; and
   a computer processor, configured to:
      receive the sensor signal,
      analyze the sensor signal,
      in response to the analyzing, identify whether the subject is in a pregnant state or a non-pregnant state, and
      generate an output in response thereto.

Inventive concept 201. The apparatus according to inventive concept 200, wherein the bed includes a mattress, and wherein the sensor is configured to be disposed underneath the mattress and to automatically monitor the subject while the subject is lying upon the mattress.

Inventive concept 202. The apparatus according to inventive concept 200, wherein the computer processor is configured to identify whether the subject is in the pregnant state or the non-pregnant state without determining a temperature of the subject.

Inventive concept 203. The apparatus according to inventive concept 200, wherein the sensor is configured not to measure a temperature of the subject.

Inventive concept 204. The apparatus according to inventive concept 200, wherein the sensor is configured to monitor the subject without having a direct line of sight of the subject or clothes the subject is wearing.

Inventive concept 205. The apparatus according to inventive concept 200, wherein the sensor is configured to monitor the subject without requiring compliance of the subject.

Inventive concept 206. The apparatus according to inventive concept 200, wherein the sensor is configured to monitor the subject without contacting the subject or clothes the subject is wearing, and without viewing the subject or clothes the subject is wearing.

Inventive concept 207. The apparatus according to inventive concept 200, wherein the output includes a control signal to a room-climate-regulation device, and the computer processor is configured to generate the output by communicating the control signal to the room-climate-regulation device in response to the identified state.

Inventive concept 208. The apparatus according to inventive concept 200, wherein the computer processor is configured to identify whether the subject is in the pregnant state or the non-pregnant state, using a machine-learning algorithm.

Inventive concept 209. The apparatus according to any one of inventive concepts 200-208, wherein the computer processor is configured:
   in response to the analyzing, to identify an aspect of the sensor signal selected from the group consisting of: a cardiac-related aspect of the sensor signal, and a respiration-related aspect of the sensor signal, and
   to identify whether the subject is in the pregnant state or the non-pregnant state, in response to the identified aspect.

Inventive concept 210. The apparatus according to inventive concept 209, further comprising an input unit,
  wherein the identified aspect of the sensor signal is a currently-identified aspect of the sensor signal, and
  wherein the computer processor is configured to identify whether the subject is in the pregnant state or the non-pregnant state by:
    at least once, prior to the identification of the currently-identified aspect of the sensor signal:
      receiving, via the input unit, an input that is indicative of whether the subject is pregnant, and
      identifying an aspect of the sensor signal at a time at which the input was received,
    in response to the input and the identified aspect of the sensor signal, learning a pregnancy-identification rule, and
    using the pregnancy-identification rule to identify whether the subject is in the pregnant state or the non-pregnant state.

Inventive concept 211. The apparatus according to inventive concept 209,
  wherein the identified aspect of the sensor signal includes a respiratory rate of the subject, and
  wherein the computer processor is configured to (i) identify that the subject is pregnant by ascertaining that the identified respiratory rate is not lower than a baseline respiratory rate, and (ii) identify that the subject is not pregnant by ascertaining that the identified respiratory rate is lower than the baseline respiratory rate.

Inventive concept 212. The apparatus according to inventive concept 209,
  wherein the identified aspect of the sensor signal includes a heart rate of the subject, and
  wherein the computer processor is configured to (i) identify that the subject is pregnant by ascertaining that the identified heart rate is not lower than a baseline heart rate, and (ii) identify that the subject is not pregnant by ascertaining that the identified heart rate is lower than the baseline heart rate.

Inventive concept 213. The apparatus according to inventive concept 212,
  wherein the identified heart rate of the subject is a currently-identified heart rate, and
  wherein the computer processor is further configured to identify the baseline heart rate in response to a previously-identified heart rate of the subject that was identified less than fourteen days prior to identifying the currently-identified heart rate.

There is further provided the following inventive concepts, in accordance with some applications of the present invention:

Inventive concept 1. Apparatus for use with a speaker, the apparatus comprising:
  a sensor configured to monitor a subject and to generate a sensor signal in response thereto; and
  a control unit configured to:
    analyze the sensor signal,
    control a property of a sound signal, in response to (a) the analyzing of the sensor signal, and (b) a historical physiological parameter of the subject that was exhibited in response to a historical sound signal, and
    drive the speaker to play the sound signal.

Inventive concept 2. The apparatus according to inventive concept 1, wherein the control unit is configured to:
  at a first time, set the property of the sound signal to a particular setting, and drive the speaker to play the sound signal, and
  at a second time following the first time, in response to (a) the sensor signal indicating that the subject has awakened prematurely, and (b) the subject having fallen asleep at the first time in response to the setting of the property to the particular setting:
    set the property of the sound signal to the particular setting, and
    drive the speaker to play the sound signal.

Inventive concept 3. The apparatus according to inventive concept 1, wherein the apparatus is for use with a mechanism selected from the group consisting of: a vibrating mechanism, and a rocking mechanism, and wherein the control unit is further configured to control the selected mechanism in response to the analyzing of the sensor signal.

Inventive concept 4. The apparatus according to inventive concept 1, wherein the control unit is configured to:
  at least by analyzing the sensor signal, ascertain that the subject is trying to fall asleep, and
  control the property of the sound signal, in response thereto.

Inventive concept 5. The apparatus according to inventive concept 1, wherein the control unit is configured to:
  by analyzing the sensor signal, ascertain a sleep stage of the subject, and
  control the property of the sound signal, in response to the ascertained sleep stage.

Inventive concept 6. The apparatus according to any one of inventive concepts 1-5, wherein the historical physiological parameter is selected from the group consisting of: a quality of sleep, a time-to-fall-asleep, a heart-rate-variability, a change in heart rate, a change in respiratory rate, a change in heart-rate-variability, a change in blood pressure, a rate of change in heart rate, a rate of change in respiratory rate, a rate of change in heart-rate-variability, and a rate of change in blood pressure, the control unit being configured to control the property of the sound signal in response to the selected historical physiological parameter.

Inventive concept 7. The apparatus according to any one of inventive concepts 1-5, wherein the control unit is configured to select content of the sound signal in response to a manual input.

Inventive concept 8. The apparatus according to any one of inventive concepts 1-5, wherein the property is selected from the group consisting of: content, genre, volume, frequency, and phase-shift, the control unit being configured to control the selected property.

Inventive concept 9. The apparatus according to inventive concept 8,
  wherein the selected property is the frequency, and
  wherein the control unit is configured to control the frequency of the sound signal by setting the frequency to be an offset less than a rate selected from the group consisting of: a heart rate of the subject, and a respiratory rate of the subject,
  the control unit being configured to control the offset in response to analyzing the sensor signal.

Inventive concept 10. The apparatus according to inventive concept 8, wherein the selected property is a phase-shift with respect to a signal selected from the group consisting of: a cardiac signal of the subject, and a respiratory signal of the subject, the control unit being configured to control the phase-shift with respect to the selected signal.

Inventive concept 11. Apparatus for use with an alerting device, the apparatus comprising:

at least one sensor configured to monitor a care-provider and a care-receiver, and to generate a signal in response thereto; and
a control unit configured to:
analyze the signal,
in response thereto, drive the alerting device to alert the care-provider to provide care for the care-receiver.

Inventive concept 12. The apparatus according to inventive concept 11, wherein the at least one sensor is configured to monitor the care-provider and the care-receiver without contacting or viewing the care-provider, without contacting or viewing clothes the care-provider is wearing, without contacting or viewing the care-receiver, and without contacting or viewing clothes the care-receiver is wearing.

Inventive concept 13. The apparatus according to inventive concept 11 or 12, wherein the control unit is configured to drive the alerting device to alert the care-provider in response to ascertaining, by analyzing the signal, (a) a sleep stage of the care-provider, and (b) a sleep stage of the care-receiver.

Inventive concept 14. The apparatus according to inventive concept 11 or 12, wherein the control unit is configured to drive the alerting device to alert the care-provider in response to historical sleep-related data of a person selected from the group consisting of: the care-provider, and the care-receiver.

Inventive concept 15. Apparatus for use with a mechanism selected from the group consisting of: a vibrating mechanism, and a rocking mechanism, the apparatus comprising:
a sensor configured to monitor a subject and to generate a sensor signal in response thereto; and
a control unit configured to:
analyze the sensor signal, and
control the selected mechanism in response thereto by sending a control signal to the selected mechanism.

Inventive concept 16. The apparatus according to inventive concept 15, wherein, in response to analyzing the sensor signal, the control unit is configured to:
ascertain that the subject is not sleeping, and
activate the selected mechanism in response thereto.

Inventive concept 17. The apparatus according to inventive concept 15, wherein the control unit is configured to control the selected mechanism, further in response to historical sleep-related data of the subject.

Inventive concept 18. The apparatus according to any one of inventive concepts 15-17, wherein the control unit is configured to:
at a first time:
vary a parameter of the selected mechanism, the parameter being selected from the group consisting of: a vibration frequency, a vibration amplitude, a rocking frequency, and a rocking amplitude, and
by analyzing the sensor signal, identify a value of the selected parameter that is more conducive to sleep of the subject, relative to other values, and
at a second time following the first time, set the selected parameter to the identified value.

Inventive concept 19. The apparatus according to any one of inventive concepts 15-17, wherein the control unit is configured to:
at a first time, set a parameter of the selected mechanism to a particular value by sending the control signal to the selected mechanism, and
at a second time following the first time, in response to (a) the sensor signal indicating that the subject has awakened prematurely, and (b) the subject having fallen asleep at the first time in response to the setting of the parameter to the particular value, set the parameter of the selected mechanism to the particular value.

Inventive concept 20. A method for use with a home appliance, the method comprising:
using a sensor to monitor sleep of a subject and to generate a signal in response thereto; and
using a control unit:
analyzing the signal,
in response thereto, ascertaining a sleep stage of the subject, and
in response thereto, controlling the home appliance.

Inventive concept 21. The method according to inventive concept 20, wherein using the sensor comprises using a motion sensor.

Inventive concept 22. The method according to inventive concept 20, wherein using the sensor to monitor the sleep of the subject comprises using the sensor to monitor the sleep of the subject without contacting or viewing the subject, and without contacting or viewing clothes the subject is wearing.

Inventive concept 23. The method according to inventive concept 20, wherein controlling the home appliance comprises controlling the home appliance in response to historical sleep-related data of the subject.

Inventive concept 24. The method according to any one of inventive concepts 20-23, wherein the home appliance is selected from the group consisting of: a washing machine, a dryer, an air conditioner, a heater, a refrigerator, a freezer, and a dishwasher, the method comprising controlling the selected home appliance.

Inventive concept 25. The method according to any one of inventive concepts 20-23, wherein controlling the home appliance comprises inhibiting activation of the home appliance, in response to ascertaining that the sleep stage of the subject is a light-sleep stage.

Inventive concept 26. The method according to any one of inventive concepts 20-23, wherein controlling the home appliance comprises activating the home appliance, in response to ascertaining that the sleep stage of the subject is a slow-wave sleep stage.

Inventive concept 27. Apparatus for use with a first noise-making device and a second noise-making device, the apparatus comprising:
a sensor configured to monitor sleep of a subject and to generate a sensor signal in response thereto; and
a control unit configured to:
analyze the sensor signal,
receive a device signal from the second noise-making device,
in response to (a) analyzing the sensor signal, and (b) the device signal, ascertain that the subject is likely to awaken due to an upcoming activation of the second noise-making device, and
in response thereto, activate the first noise-making device.

Inventive concept 28. Apparatus comprising:
a sensor configured to monitor sleep of a baby, and to generate a signal in response thereto;
an electromechanical arm; and
a control unit configured to:
analyze the signal, and
in response thereto, drive the electromechanical arm to deliver a comfort-inducing object to the baby.

Inventive concept 29. The apparatus according to inventive concept 28, wherein the sensor is configured to monitor the sleep of the baby without contacting or viewing the baby, and without contacting or viewing clothes the baby is wearing.

Inventive concept 30. Apparatus comprising:
  a sensor configured to monitor a baby, and to generate a signal in response thereto; and
  a control unit configured to:
    analyze the signal,
    in response thereto, ascertain that a mouth of the baby is performing a sucking motion, and
    in response thereto, generate an alert.

Inventive concept 31. The apparatus according to inventive concept 30, wherein the sensor is configured to monitor the sleep of the baby without contacting or viewing the baby, and without contacting or viewing clothes the baby is wearing.

Inventive concept 32. Apparatus comprising:
  a sensor configured to monitor a baby, and to generate a signal in response thereto;
  an electromechanical arm; and
  a control unit configured to:
    analyze the signal,
    in response thereto, ascertain that a mouth of the baby is performing a sucking motion, and
    in response thereto, drive the electromechanical arm to deliver a comfort-inducing object to the baby.

Inventive concept 33. The apparatus according to inventive concept 32, wherein the sensor is configured to monitor the baby without contacting or viewing the baby, and without contacting or viewing clothes the baby is wearing.

Inventive concept 34. A method comprising:
  using a sensor to monitor sleep of a subject, and to generate a signal in response thereto; and
  using a control unit:
    accepting an input indicative of a person desiring to perform an activity that is potentially disturbing to the sleep of the subject,
    analyzing the signal,
    in response to analyzing the signal, identifying a time during which the activity is likely to be less disturbing to the sleep of the subject, relative to another time, and
    generating a notification indicating a suitability of performing the activity at the identified time.

Inventive concept 35. The method according to inventive concept 34, wherein using the sensor comprises using a motion sensor.

Inventive concept 36. Apparatus for use with a plurality of patients requiring respective care-provision tasks, the apparatus comprising:
  a plurality of sensors configured to monitor sleep of the patients, and to generate a plurality of signals in response thereto; and
  a control unit configured to:
    analyze the signals,
    in response thereto, ascertain respective sleep stages of the patients,
    in response to the respective sleep stages, determine a prioritization of at least one of the care-provision tasks over at least one other of the care-provision tasks, and
    generate an output indicative of the prioritization.

Inventive concept 37. The apparatus according to inventive concept 36, further comprising a location sensing system that comprises a plurality of location sensors, the location sensing system being configured to:
  identify respective locations of a plurality of care-providers, and
  generate a location-sensing-system signal in response thereto,
  wherein the control unit is configured to determine the prioritization further in response to the location-sensing-system signal.

Inventive concept 38. Apparatus for ascertaining that a subject is likely to be resting on a resting surface, the apparatus comprising:
  a sensor configured to monitor a resting surface and to generate a sensor signal in response thereto; and
  a processor configured to:
    identify a level of correspondence between the sensor signal and a signal generated by a handheld telecommunications device of the subject, and
    in response to the level of correspondence, generate an output that is indicative of whether the subject is likely to be resting on the resting surface.

Inventive concept 39. The apparatus according to inventive concept 38,
  wherein the processor is configured to:
    ascertain, for a plurality of time periods, (a) a number N1 of the time periods during which the level of correspondence between the sensor signal and the signal generated by the handheld telecommunications device is greater than a correspondence threshold, and (b) a number N2 of the time periods during which the level of correspondence between the sensor signal and the signal generated by the handheld telecommunications device is not greater than the correspondence threshold, and
    generate the output in response to a relationship between N1 and N2.

Inventive concept 40. The apparatus according to inventive concept 39, wherein the processor is configured to generate the output in response to a ratio of N1 to N2.

Inventive concept 41. The apparatus according to any one of inventive concepts 38-40, wherein the processor is further configured to, by periodically analyzing the signal generated by the telecommunications device, ascertain that the telecommunications device is periodically used by the subject when the subject is not on the resting surface, and wherein the processor is configured to identify the level of correspondence at least partially in response thereto.

Inventive concept 42. The apparatus according to any one of inventive concepts 38-40, wherein the telecommunications device includes a device-movement sensor configured to detect movement of the telecommunications device and to generate a device-movement signal in response thereto, and wherein the processor is configured to:
  identify the level of correspondence between the sensor signal and the signal generated by the handheld telecommunications device of the subject by identifying a level of correspondence between the sensor signal and the device-movement signal, and
  in response to the level of correspondence between the sensor signal and the device-movement signal, generate the output.

Inventive concept 43. The apparatus according to inventive concept 42, wherein the processor is configured to:
  by analyzing the sensor signal, ascertain that a person is resting on the resting surface,
  by analyzing the device-movement signal, ascertain that the telecommunications device is not moving,
  in response thereto, ascertain that the subject is likely to be resting on the resting surface, and
  in response thereto, generate the output.

Inventive concept 44. The apparatus according to inventive concept 42, wherein the processor is configured to:

by analyzing the sensor signal, ascertain that a person is resting on the resting surface,
by analyzing the device-movement signal, ascertain that the telecommunications device is moving,
in response thereto, ascertain that the subject is not likely to be resting on the resting surface, and
in response thereto, generate the output.

Inventive concept 45. The apparatus according to any one of inventive concepts 38-40, wherein the signal generated by the handheld telecommunications device includes a usage signal indicative of whether the telecommunications device is being used, and wherein the processor is configured to:
identify the level of correspondence between the sensor signal and the signal generated by the handheld telecommunications device of the subject by identifying a correspondence between the sensor signal and the usage signal, and
in response to the correspondence between the sensor signal and the usage signal, generate the output.

Inventive concept 46. The apparatus according to inventive concept 45, wherein the processor is configured to:
by analyzing the sensor signal, ascertain that a person is resting on the resting surface,
by analyzing the usage signal, ascertain that the telecommunications device is not being used,
in response thereto, ascertain that the subject is likely to be resting on the resting surface, and
in response thereto, generate the output.

Inventive concept 47. The apparatus according to inventive concept 45, wherein the processor is configured to:
by analyzing the sensor signal, ascertain that a person is on the resting surface,
by analyzing the usage signal, ascertain that the telecommunications device is being used,
in response thereto, ascertain that the subject is not likely to be resting on the resting surface, and
in response thereto, generate the output.

Inventive concept 48. Apparatus for ascertaining that a subject is likely to be resting on a resting surface, the apparatus comprising:
a sensor configured to monitor a resting surface and to generate a sensor signal in response thereto; and
a processor configured to:
by analyzing the sensor signal, ascertain that a person is resting on the resting surface,
in response to a signal generated by a telecommunications device of the subject, ascertain that the telecommunications device is within a given distance of the resting surface,
in response thereto, ascertain that the subject is likely to be resting on the resting surface, and
in response thereto, generate an output indicating that the subject is likely to be resting on the resting surface.

Inventive concept 49. The apparatus according to inventive concept 48,
wherein the processor is further configured to receive an input indicative of coordinates of a location of the resting surface,
wherein the signal generated by the telecommunications device is indicative of coordinates of a location of the telecommunications device, and
wherein the processor is configured to ascertain that the telecommunications device is within the given distance of the resting surface by comparing the location of the telecommunications device with the location of the resting surface.

Inventive concept 50. Apparatus for controlling a room-climate-regulation device, the apparatus comprising:
a sensor, configured to monitor a subject and generate a sensor signal in response thereto; and
a control unit, configured to:
analyze the signal,
in response thereto, identify a sleep stage of the subject, and
in response to the identified sleep stage, control the room-climate-regulation device by sending a control signal to the room-climate-regulation device.

Inventive concept 51. The apparatus according to inventive concept 50, wherein the sensor comprises a motion sensor configured to sense motion of the subject.

Inventive concept 52. The apparatus according to inventive concept 50, wherein the sensor is configured to monitor the subject without contacting or viewing the subject, and without contacting or viewing clothes the subject is wearing.

Inventive concept 53. The apparatus according to inventive concept 51, wherein the sensor is configured to monitor the subject without contacting or viewing the subject, and without contacting or viewing clothes the subject is wearing.

Inventive concept 54. The apparatus according to any one of inventive concepts 50-53,
wherein the control unit is further configured to ascertain, in response to analyzing the sensor signal, that a sleep score of the subject is lower than a baseline value,
wherein the apparatus further comprises a user interface,
wherein the control unit is configured to drive the user interface to prompt the subject to use the user interface to enter an input that includes at least one factor that may have caused the sleep score to be lower than the baseline value, and
wherein the control unit is configured to control the room-climate-regulation device in response to the input.

Inventive concept 55. The apparatus according to any one of inventive concepts 50-53, wherein the control unit is configured to control the room-climate-regulation device by controlling a room-climate-regulation parameter selected from the group consisting of: temperature, humidity, and fan speed.

Inventive concept 56. The apparatus according to any one of inventive concepts 50-53, wherein the sensor is configured to monitor the subject by monitoring a parameter of the subject selected from the group consisting of: motion, heart rate, heart rate variability, heartbeat amplitude, respiration rate, respiration amplitude, respiration-cycle variability, tremor, and left ventricular ejection time.

Inventive concept 57. The apparatus according to any one of inventive concepts 50-53, wherein the control unit is further configured to:
ascertain, in response to analyzing the sensor signal, a sleep score of the subject, and,
in response to the sleep score, control the room-climate-regulation device.

Inventive concept 58. The apparatus according to any one of inventive concepts 50-53, wherein the control unit is further configured to:
ascertain, in response to analyzing the sensor signal, a sleep score of the subject, and,
in response to the sleep score, generate an output that includes a suggested setting for the room-climate-regulation device.

Inventive concept 59. The apparatus according to any one of inventive concepts 50-53, wherein the control unit is configured to change a setting of the room-climate-regulation device in response to a premature awakening of the subject.

Inventive concept 60. The apparatus according to any one of inventive concepts 50-53, wherein the control unit is configured to:
differentially identify at least two sleep stages selected from the group consisting of: a falling-asleep stage, a beginning-sleep stage, a mid-sleep stage, a premature-awakening stage, an awakening stage, a light sleep stage, a slow-wave sleep stage, and a rapid-eye-movement sleep stage, and
in response to the differentially identified sleep stages, control the room-climate-regulation device by sending the control signal to the room-climate-regulation device.

Inventive concept 61. The apparatus according to any one of inventive concepts 50-53, wherein the control unit is configured to, in response to the identified sleep stage, control a noise-emission of the room-climate-regulation device even without adjusting a temperature setting of the room-climate-regulation device.

Inventive concept 62. The apparatus according to inventive concept 61, wherein the room-climate-regulation device includes a fan, and wherein the control unit is configured to control the noise-emission of the room-climate-regulation device by controlling a rotating speed of the fan.

Inventive concept 63. The apparatus according to inventive concept 61, wherein the control unit is configured to control the noise-emission of the room-climate-regulation device further in response to an ambient noise level.

Inventive concept 64. The apparatus according to inventive concept 61, wherein the control unit is configured to reduce a noise level of the room-climate-regulation device in response to the identified sleep stage being a slow-wave sleep stage.

Inventive concept 65. The apparatus according to inventive concept 61, wherein the control unit is configured to increase a noise level of the room-climate-regulation device in response to the identified sleep stage being a slow-wave sleep stage.

Inventive concept 66. The apparatus according to inventive concept 61, wherein the control unit is configured to reduce a noise level of the room-climate-regulation device in response to the identified sleep stage not being a slow-wave sleep stage.

Inventive concept 67. The apparatus according to inventive concept 61, wherein the control unit is configured to increase a noise level of the room-climate-regulation device in response to the identified sleep stage not being a slow-wave sleep stage.

Inventive concept 68. The apparatus according to inventive concept 61, wherein the control unit is configured to control a frequency of emitted noise of the room-climate-regulation device in response to (a) the identified sleep stage, and (b) a rate selected from the group consisting of: a heart rate of the subject, and a respiratory rate of the subject.

Inventive concept 69. The apparatus according to any one of inventive concepts 50-53, wherein the control unit is configured to, in response to the identified sleep stage, control a temperature setting of the room-climate-regulation device.

Inventive concept 70. The apparatus according to inventive concept 69, wherein the control unit is configured to lower the temperature setting of the room-climate-regulation device in response to the identified sleep stage being a rapid-eye-movement sleep stage.

Inventive concept 71. The apparatus according to inventive concept 69, wherein the control unit is configured to:
by analyzing the signal, identify an indication of a body temperature of the subject, and
in response to the indication, control the temperature setting.

Inventive concept 72. The apparatus according to inventive concept 71, wherein the control unit is configured to:
by analyzing the signal, ascertain that the subject is uncomfortable with a current ambient temperature, and
in response to the ascertaining, control the temperature setting.

Inventive concept 73. The apparatus according to inventive concept 71, wherein the control unit is configured to ascertain that the subject is uncomfortable with the current ambient temperature by identifying a tremor component of the signal.

Inventive concept 74. The apparatus according to any one of inventive concepts 50-53, further comprising a user interface configured to accept an input from the subject, the input including at least two distinct settings for the room-climate-regulation device corresponding to respective different sleep stages,
wherein the control unit is configured to control the room-climate-regulation device in response to the input.

Inventive concept 75. The apparatus according to inventive concept 74, wherein the control unit is further configured to drive the user interface to prompt the subject to enter the input, in response to a change in a parameter selected from the group consisting of: a season, an ambient temperature, an ambient humidity, and a going-to-sleep time.

Inventive concept 76. The apparatus according to inventive concept 74, wherein the sensor is further configured to sense a weight of a blanket of the subject, and wherein the control unit is further configured to drive the user interface to prompt the subject to enter the input, in response to a change in the sensed weight.

Inventive concept 77. The apparatus according to inventive concept 74, wherein the control unit is further configured to:
ascertain, in response to analyzing the sensor signal, a sleep score of the subject, and
drive the user interface to prompt the subject to enter the input, in response to the ascertained sleep score being lower than a baseline value.

Inventive concept 78. The apparatus according to inventive concept 77, wherein the control unit is configured to ascertain the sleep score by computing a score from at least one parameter selected from the group consisting of: a time to fall asleep, a duration of sleep, a percentage of in-bed time during which the subject is sleeping, and a measure of relaxation of the subject.

Inventive concept 79. The apparatus according to any one of inventive concepts 50-53, wherein the control unit is configured to:
for each of a plurality of different settings of the room-climate-regulation device, ascertain, in response to analyzing the sensor signal, a sleep score of the subject; and
in response thereto, generate an output indicative of a setting that is conducive to a higher sleep score, relative to other settings.

Inventive concept 80. The apparatus according to inventive concept 79, further comprising a user interface configured to accept an input from the subject, wherein the control unit is configured to set the plurality of different settings in response to the input.

Inventive concept 81. The apparatus according to inventive concept 79, wherein the control unit is configured to set the plurality of different settings even without any deliberate input from the subject.

Inventive concept 82. The apparatus according to any one of inventive concepts 50-53,
- wherein the subject is a first subject who shares a room with a second subject,
- wherein the apparatus further comprises a second sensor, configured to monitor the second subject and generate a second sensor signal in response thereto, and
- wherein the control unit is configured to:
  - analyze the second sensor signal,
  - in response thereto, identify a sleep stage of the second subject, and
  - in response to the respective identified sleep stages of the subjects, control the room-climate-regulation device by sending a control signal to the room-climate-regulation device.

Inventive concept 83. The apparatus according to inventive concept 82,
- wherein the apparatus is for use with a room-climate-regulation device that can simultaneously maintain a first setting in a vicinity of the first subject, and a second setting, which is different from the first setting, in a vicinity of the second subject,
- the control unit being configured to control the room-climate-regulation device by communicating the first and second settings to the room-climate-regulation device.

Inventive concept 84. The apparatus according to inventive concept 82, wherein the control unit is further configured to:
- ascertain, in response to analyzing the sensor signals, respective sleep scores of the subjects, and
- in response to the respective sleep scores, control the room-climate-regulation device.

Inventive concept 85. The apparatus according to inventive concept 84, wherein the control unit is configured to:
- determine a setting of the room-climate-regulation device that facilitates respective sleep scores of the subjects being equal to one another, and
- control the room-climate-regulation device by communicating the setting to the room-climate-regulation device.

Inventive concept 86. The apparatus according to inventive concept 84, wherein the control unit is configured to:
- determine a setting of the room-climate-regulation device, in response to an average sleep score of the subjects, and
- control the room-climate-regulation device by communicating the setting to the room-climate-regulation device.

Inventive concept 87. The apparatus according to inventive concept 86, wherein the control unit is configured to:
- determine a setting of the room-climate-regulation device that maximizes the average sleep score of the subjects, a higher sleep score being indicative of a more restful sleeping session relative to a lower sleep score, and
- control the room-climate-regulation device by communicating the setting to the room-climate-regulation device.

Inventive concept 88. The apparatus according to inventive concept 86,
- wherein the setting is a first setting, and
- wherein, in response to one of the subjects having fallen asleep, the control unit is configured to communicate a second setting to the room-climate-regulation device, the second setting being different from the first setting.

Inventive concept 89. The apparatus according to inventive concept 82, wherein the control unit is configured to:
- communicate a first setting to the room-climate-regulation device in response to one of the sensor signals indicating that one of the subjects is trying to fall asleep, the first setting being more conducive to sleep of the one of the subjects, relative to other settings, and
- subsequently, in response to the sensor signals indicating that (a) the one of the subjects has fallen asleep, and (b) the other one of the subjects is trying to fall asleep, communicate a second setting to the room-climate-regulation device, the second setting being different from the first setting.

Inventive concept 90. The apparatus according to inventive concept 89, wherein the control unit is configured to generate an output to the other one of the subjects, the output indicating that the one of the subjects has fallen asleep.

Inventive concept 91. Apparatus for controlling a thermoregulation device, the apparatus comprising:
- a motion sensor, configured to monitor a subject and generate a motion signal in response thereto; and
- a control unit, configured to:
  - analyze the motion signal, and
  - in response thereto, control a temperature setting of the thermoregulation device.

Inventive concept 92. Apparatus for use with a room-climate-regulation device, the apparatus comprising:
- a sensor, configured to monitor a subject and to generate a sensor signal in response thereto; and
- a control unit, configured to:
  - analyze the sensor signal,
  - in response thereto, identify a rate selected from the group consisting of: a heart rate of the subject, and a respiratory rate of the subject, and
  - control a property of emitted noise of the room-climate-regulation device in response to the identified rate, the property being selected from the group consisting of: a frequency, and a phase-shift.

Inventive concept 93. Apparatus for use with a vibrating mechanism, the apparatus comprising:
- a sensor, configured to monitor a subject on a resting surface and generate a sensor signal in response thereto; and
- a control unit, configured to:
  - analyze the sensor signal,
  - in response thereto, identify a posture of the subject, and
  - in response to the identified posture, drive the vibrating mechanism to vibrate.

Inventive concept 94. The apparatus according to inventive concept 93, wherein the control unit is further configured to, in response to analyzing the sensor signal, identify a sleep stage of the subject, and wherein the control unit is configured to drive the vibrating mechanism to vibrate, further in response to the identified sleep stage.

Inventive concept 95. The apparatus according to inventive concept 94, wherein the control unit is configured to drive the vibrating mechanism to vibrate in response to the identified sleep stage being selected from the group consisting of: a sleep stage that is within 5 minutes of an onset of a rapid-eye-movement sleep stage, and a sleep stage that is within 5 minutes of an end of a rapid-eye-movement sleep stage.

Inventive concept 96. The apparatus according to any one of inventive concepts 93-95, wherein the sensor is a first sensor and the sensor signal is a first sensor signal, wherein the apparatus further comprises a second sensor configured to monitor a partner of the subject and generate a second sensor signal in response thereto, wherein the control unit is further configured to analyze the second sensor signal and, in response thereto, identify a sleep stage of the partner, and wherein the control unit is configured to drive the vibrating mechanism to vibrate, further in response to the identified sleep stage of the partner.

Inventive concept 97. The apparatus according to any one of inventive concepts 93-95, wherein the control unit is further configured to identify an episode of the subject selected from the group consisting of: a snoring episode, and an apnea episode, and wherein the control unit is configured to drive the vibrating mechanism to vibrate, further in response to the identified episode.

Inventive concept 98. The apparatus according to any one of inventive concepts 93-95, wherein the vibrating mechanism includes a vibrating wristwatch, and the control unit is configured to drive the vibrating mechanism to vibrate by driving the vibrating wristwatch to vibrate.

Inventive concept 99. Apparatus for use with an adjustable resting surface, the apparatus comprising:

a sensor, configured to monitor a subject on the resting surface and generate a sensor signal in response thereto; and a control unit, configured to:
analyze the sensor signal,
in response thereto, identify a posture of the subject, and
in response to the identified posture, adjust a parameter of the resting surface by communicating a signal to the resting surface.

Inventive concept 100. The apparatus according to inventive concept 99, wherein the control unit is configured to, in response to the identified posture, adjust an angle of the resting surface.

Inventive concept 101. The apparatus according to inventive concept 99, wherein the control unit is further configured to, in response to analyzing the sensor signal, identify a sleep stage of the subject, and wherein the control unit is configured to adjust the parameter of the resting surface, further in response to the identified sleep stage.

Inventive concept 102. The apparatus according to inventive concept 101, wherein the control unit is configured to adjust the parameter of the resting surface in response to the identified sleep stage being selected from the group consisting of: a sleep stage that is within 5 minutes of an onset of a rapid-eye-movement sleep stage, and a sleep stage that is within 5 minutes of an end of a rapid-eye-movement sleep stage.

Inventive concept 103. The apparatus according to any one of inventive concepts 99-102, wherein the sensor is a first sensor and the sensor signal is a first sensor signal, wherein the apparatus further comprises a second sensor configured to monitor a partner of the subject and generate a second sensor signal in response thereto, wherein the control unit is further configured to analyze the second sensor signal and, in response thereto, identify a sleep stage of the partner, and wherein the control unit is configured to adjust the parameter of the resting surface, further in response to the identified sleep stage of the partner.

Inventive concept 104. The apparatus according to any one of inventive concepts 99-102, wherein the control unit is further configured to identify an episode of the subject selected from the group consisting of: a snoring episode, and an apnea episode, and wherein the control unit is configured to adjust the parameter of the resting surface, further in response to the identified episode.

Inventive concept 105. The apparatus according to any one of inventive concepts 99-102, wherein the control unit is further configured to identify a coughing episode of the subject, and wherein the control unit is configured to adjust the parameter of the resting surface, further in response to the identified coughing episode.

Inventive concept 106. The apparatus according to inventive concept 105, wherein the adjustable resting surface includes an inflatable pillow, and the control unit is configured to adjust a parameter of the resting surface by adjusting a parameter of the inflatable pillow.

Inventive concept 107. A method for monitoring a subject, the method comprising:

using a motion sensor located in a vehicle, in a seat of the subject, sensing physiological activity of the subject, and generating a motion signal in response thereto; and using a control unit:
analyzing the motion signal; and
generating an output in response thereto.

Inventive concept 108. The method according to inventive concept 107, wherein the vehicle is an airplane, the method comprising using the motion sensor in the airplane.

Inventive concept 109. The method according to inventive concept 107 or 108, wherein analyzing the motion signal comprises identifying a likelihood of a clinical event of the subject, and wherein generating the output comprises generating an alert in response to the identified likelihood.

Inventive concept 110. The method according to inventive concept 107 or 108, wherein analyzing the motion signal comprises identifying a likelihood that the subject is a carrier of a disease, and wherein generating the output comprises generating an alert in response to the identified likelihood.

Inventive concept 111. The method according to inventive concept 107 or 108, wherein analyzing the motion signal comprises identifying that the subject is drowsy, and wherein generating the output comprises generating an alert in response to identifying that the subject is drowsy.

Inventive concept 112. The method according to inventive concept 107 or 108, wherein analyzing the motion signal comprises identifying that the subject is sleeping, and wherein generating the output comprises generating the output in response to identifying that the subject is sleeping.

Inventive concept 113. The method according to inventive concept 107 or 108, wherein analyzing the motion signal comprises identifying an elevated stress level of the subject, and wherein generating the output comprises generating an alert in response to the elevated stress level.

Inventive concept 114. The method according to inventive concept 113,
    wherein the vehicle includes a multi-person vehicle,
    the method further comprising:
        using at least one other motion sensor located in the vehicle, in a seat of another subject, sensing physiological activity of the other subject, and generating another motion signal in response thereto; and
        using the control unit, analyzing the other motion signal, and, in response thereto, identifying an elevated stress level of the other subject,
        wherein generating the output comprises generating an alert in response to each of the subjects having an elevated stress level.

Inventive concept 115. A method for monitoring a subject, the method comprising:
    using a motion sensor located in a casino, in a seat of the subject, sensing physiological activity of the subject, and generating a motion signal in response thereto; and
    using a control unit:
        analyzing the motion signal; and
        generating an alert in response thereto.

Inventive concept 116. The method according to inventive concept 115, wherein analyzing the motion signal comprises identifying an elevated stress level of the subject, and wherein generating the alert comprises generating an alert in response to the elevated stress level.

Inventive concept 117. The method according to inventive concept 116, further comprising:
    using at least one other motion sensor located in the casino, in a seat of another subject, sensing physiological activity of the other subject, and generating another motion signal in response thereto; and
    using the control unit, analyzing the other motion signal, and, in response thereto, identifying an elevated stress level of the other subject,
    wherein generating the alert comprises generating an alert in response to each of the subjects having an elevated stress level.

Inventive concept 118. Apparatus for use with (i) a plurality of subjects sharing a common area, and (ii) a controllable mechanism, the apparatus comprising:
    one or more physiological sensors configured to monitor conditions of the subjects and to generate, in response thereto, a respective sensor signal for each one of the subjects; and
    a control unit configured to:
        analyze the sensor signals,
        in response to analyzing the sensor signals, determine a prioritization of the condition of one of the subjects over the condition of another one of the subjects,
        in response to the prioritization, decide whether to control the controllable mechanism, and
        in response to (i) the prioritization, and (ii) deciding to control the controllable mechanism, control the controllable mechanism by communicating a control signal to the controllable mechanism.

Inventive concept 119. The apparatus according to inventive concept 118, wherein the controllable mechanism is a room-climate-regulation device, the control unit being configured to control the room-climate-regulation device.

Inventive concept 120. The apparatus according to inventive concept 118, wherein the controllable mechanism is an adjustable resting surface, the control unit being configured to control the adjustable resting surface.

Inventive concept 121. The apparatus according to inventive concept 118, wherein the controllable mechanism is a sound-playing device, the control unit being configured to control the sound-playing device.

Inventive concept 122. The apparatus according to inventive concept 118, wherein the controllable mechanism is an illumination device, the control unit being configured to control the illumination device.

Inventive concept 123. The apparatus according to inventive concept 118, wherein the control unit is configured to determine the prioritization in response to determining that (a) one of the subjects is sleeping, and (b) another one of the subjects is not sleeping.

Inventive concept 124. The apparatus according to inventive concept 118, further comprising a user interface configured to accept an input from a user, wherein the control unit is configured to determine the prioritization further in response to the input.

Inventive concept 125. The apparatus according to inventive concept 118, wherein the control unit is configured to determine the prioritization in response to a health condition of at least one of the subjects.

Inventive concept 126. The apparatus according to inventive concept 125, further comprising at least one body-temperature sensor configured to (i) detect a body temperature of the at least one of the subjects, and (ii) generate a body-temperature signal in response thereto, wherein the control unit is further configured to determine the health condition of the at least one of the subjects in response to the body-temperature signal.

Inventive concept 127. The apparatus according to any one of inventive concepts 118-126,
    wherein the physiological sensors are configured to monitor comfort of the subjects, and
    wherein the control unit is configured to determine the prioritization by determining a prioritization of comfort of one of the subjects over comfort of another one of the subjects.

Inventive concept 128. The apparatus according to any one of inventive concepts 118-126,
    wherein the physiological sensors are configured to monitor sleep of the subjects, and
    wherein the control unit is configured to determine the prioritization by determining a prioritization of sleep of one of the subjects over sleep of another one of the subjects.

Inventive concept 129. The apparatus according to inventive concept 128,
    wherein controlling the controllable mechanism in a particular manner is (i) facilitative to sleep of a first one of the subjects, and (ii) at least potentially detrimental to sleep of a second one of the subjects, and
    wherein the control unit is configured to control the controllable mechanism in the particular manner only if the prioritization indicates that the sleep of the first one of the subjects is to be prioritized over sleep of the second one of the subjects.

Inventive concept 130. The apparatus according to inventive concept 128, wherein the controllable mechanism is a vibrating mechanism, the control unit being configured to control the vibrating mechanism.

Inventive concept 131. The apparatus according to inventive concept 128,
    wherein the control unit is configured to, in response to analyzing the sensor signals, determine that (i) one of the subjects is snoring, and (ii) another one of the subjects may be disturbed by the snoring, wherein controlling the controllable mechanism includes activating a snoring-inhibition mechanism that is disruptive to sleep of the snoring subject, and wherein the control unit is configured to activate the snoring-inhibition mechanism, unless the prioritization indicates that sleep of the snoring subject is to be prioritized over sleep of the other one of the subjects.

Inventive concept 132. The apparatus according to inventive concept 128, wherein the control unit is configured to:
identify respective sleep stages of the subjects in response to analyzing the sensor signals, and
determine the prioritization in response to identifying the respective sleep stages.

Inventive concept 133. The apparatus according to inventive concept 132,
wherein controlling the controllable mechanism in a particular manner is (i) facilitative to sleep of a first one of the subjects, and (ii) at least potentially detrimental to sleep of a second one of the subjects, and
wherein the control unit is configured to control the controllable mechanism in the particular manner only if the second one of the subjects is not sleeping deeply.

Inventive concept 134. The apparatus according to inventive concept 132,
wherein each of the respective sleep stages is selected from the group consisting of: a slow-wave sleep stage, a rapid-eye-movement sleep stage, a light sleep stage, and an awake sleep stage,
wherein the control unit is configured to assign:
a first rank to a sleep stage selected from the group consisting of: a slow-wave sleep stage, and a rapid-eye-movement sleep stage,
a second rank, which is greater than the first rank, to a sleep stage that is not assigned the first rank and that is selected from the group consisting of: the slow-wave sleep stage, and the rapid-eye-movement sleep stage,
a third rank, which is greater than the second rank, to a light sleep stage, and
a fourth rank, which is greater than the third rank, to an awake sleep stage, and
wherein a likelihood of the control unit prioritizing the sleep of a first subject over the sleep of a second subject increases with the rank of the sleep stage of the first subject.

Inventive concept 135. The apparatus according to inventive concept 132,
wherein each of the respective sleep stages is selected from the group consisting of: a slow-wave sleep stage, a rapid-eye-movement sleep stage, a light sleep stage, and an awake sleep stage,
wherein the control unit is configured to assign:
a first rank to a sleep stage selected from the group consisting of: a slow-wave sleep stage, and a rapid-eye-movement sleep stage,
a second rank, which is greater than the first rank, to a sleep stage that is not assigned the first rank and that is selected from the group consisting of: the slow-wave sleep stage, and the rapid-eye-movement sleep stage,
a third rank, which is greater than the second rank, to a light sleep stage, and
a fourth rank, which is greater than the third rank, to an awake sleep stage, and
wherein a likelihood of the control unit prioritizing the sleep of a first subject over the sleep of a second subject decreases with the rank of the sleep stage of the first subject.

Inventive concept 136. The apparatus according to inventive concept 128, wherein the control unit is configured to:
in response to analyzing the sensor signals over a plurality of sleeping sessions, identify, for each of the subjects, a sleep-sensitivity of the subject to at least one phenomenon that is generally detrimental to sleep, and
determine the prioritization in response to the identified sleep-sensitivities.

Inventive concept 137. The apparatus according to inventive concept 136, wherein the control unit is configured to identify the sleep-sensitivity of each of the subjects by identifying an effect of the phenomenon on a parameter selected from the group consisting of: a duration of sleep of the subject, and a quality of sleep of the subject.

Inventive concept 138. The apparatus according to inventive concept 136, wherein the control unit is configured to be more likely to prioritize the sleep of a first one of the subjects over the sleep of a second one of the subjects if the sleep-sensitivity of the first subject is higher than the sleep-sensitivity of the second subject, relative to if the sleep-sensitivity of the first subject were not higher than the sleep-sensitivity of the second subject.

Inventive concept 139. The apparatus according to inventive concept 128, wherein the control unit is configured to:
in response to analyzing the sensor signals, calculate, at a particular time, a sleep score for each of the subjects, the sleep score being based on a parameter selected from the group consisting of: a duration of sleep during an interval preceding the particular time, and a quality of sleep during an interval preceding the particular time, and
determine the prioritization in response to the respective sleep scores.

Inventive concept 140. The apparatus according to inventive concept 139, wherein, at the particular time, the control unit is configured to be more likely to prioritize sleep of a first one of the subjects over sleep of a second one of the subjects if the sleep score of the first one of the subjects is lower than the sleep score of the second one of the subjects, relative to if the sleep score of the first one of the subjects were not lower than the sleep score of the second one of the subjects.

Inventive concept 141. The apparatus according to inventive concept 139, wherein controlling the controllable mechanism in a particular manner is (i) facilitative to sleep of a first one of the subjects, and (ii) at least potentially detrimental to sleep of a second one of the subjects, and
wherein the control unit is configured to control the controllable mechanism in the particular manner and at the particular time, in response to the sleep score of the first one of the subjects being lower than a threshold.

Inventive concept 142. The apparatus according to inventive concept 141, wherein the control unit is configured to:
identify respective sleep stages of the subjects in response to analyzing the sensor signals, and
control the controllable mechanism in the particular manner and at the particular time in response to the sleep score of the first one of the subjects being lower than the threshold, only if the first one of the subjects is not sleeping deeply.

Inventive concept 143. The apparatus according to inventive concept 142, wherein the control unit is configured to control the controllable mechanism in the particular manner and at the particular time in response to the sleep score of the first one of the subjects being lower than the threshold, only if (i) the first one of the subjects is not sleeping deeply, and (ii) the second one of the subjects is not sleeping deeply.

Inventive concept 144. Apparatus for use with an alarm clock for waking a subject, the apparatus comprising:
 a sensor configured to monitor a resting surface, and to generate a signal in response thereto; and
 a control unit configured to:
  analyze the signal,
  in response thereto, determine that, even if the resting surface is occupied by someone, the resting surface is likely not being occupied by the subject, and
  in response thereto, inhibit the alarm clock from generating an alarm.

Inventive concept 145. The apparatus according to inventive concept 144, wherein the control unit is further configured to stop inhibiting the alarm clock from generating an alarm, in response to determining that the resting surface is likely being occupied by the subject.

Inventive concept 146. Apparatus for use with an alarm clock for waking a subject, the apparatus comprising:
 a sensor configured to monitor a resting surface, and to generate a signal in response thereto; and
 a control unit, separate from the alarm clock, and configured, following a first alarm generated by the alarm clock, to:
  analyze the signal,
  in response to analyzing the signal, determine that the resting surface is likely being occupied by the subject, and
  in response thereto, drive the alarm clock to generate a second alarm.

Inventive concept 147. Apparatus for use with (i) a first subject and a second subject sharing a common sleep area, and (ii) an alarm clock, the apparatus comprising:
 a sensor configured to monitor the second subject and to generate a sensor signal in response thereto; and
 a control unit configured to:
  accept an input indicative of (i) an earliest desired awakening time, and (ii) a latest desired awakening time, for the first subject, and
  at a time between the earliest desired awakening time and the latest desired awakening time:
   analyze the sensor signal,
   in response thereto, determine a sleep stage of the second subject,
   in response to the sleep stage of the second subject, determine whether to drive the alarm clock to generate an alarm at the time, and
   in response to determining to drive the alarm clock to generate an alarm, drive the alarm clock to generate an alarm.

Inventive concept 148. The apparatus according to inventive concept 147, wherein the control unit is configured to:
 in response to analyzing the sensor signal over a plurality of sleeping sessions, identify a sleep-sensitivity of the second subject to at least one phenomenon that is generally detrimental to sleep, and
 in response to the identified sleep-sensitivity, determine whether to drive the alarm clock to generate the alarm.

Inventive concept 149. The apparatus according to inventive concept 148, wherein the control unit is configured to identify the sleep-sensitivity of the second subject by identifying an effect of the phenomenon on a parameter selected from the group consisting of: a duration of sleep of the second subject, and a quality of sleep of the second subject.

Inventive concept 150. The apparatus according to any one of inventive concepts 147-149, wherein the control unit is configured to:
 in response to analyzing the sensor signal, calculate a sleep score for the second subject, the sleep score being based on a parameter selected from the group consisting of: a duration of sleep during an interval preceding the particular time, and a quality of sleep during an interval preceding the particular time, and
 in response to the sleep score, determine whether to drive the alarm clock to generate the alarm.

Inventive concept 151. The apparatus according to any one of inventive concepts 147-149, wherein the control unit is configured to determine whether to drive the alarm clock to generate the alarm, in response to a health condition of the second subject.

Inventive concept 152. Apparatus comprising:
 a sensor configured to measure a clinical parameter of a patient, and to generate a signal in response thereto;
 a control unit configured to:
  receive the signal from the sensor,
  compare the clinical parameter to a threshold, and
  in response to the comparison, generate an alert to a clinician; and
 a user interface configured to receive an input from the clinician, the input indicating whether the clinician believes the alert to have been justified,
 the control unit being configured to adjust the threshold in response to the input.

Inventive concept 153. Apparatus for use with (i) a common area that is shared by a plurality of subjects, and (ii) a controllable mechanism, the apparatus comprising:
 at least one sensor configured to monitor the common area and to generate a sensor signal in response thereto; and
 a control unit configured to:
  analyze the sensor signal,
  in response to analyzing the sensor signal, determine which subjects of the plurality of subjects are present in the common area, and
  in response to the determining, control the controllable mechanism by communicating a control signal to the controllable mechanism.

Inventive concept 154. The apparatus according to inventive concept 153, wherein the controllable mechanism is a room-climate-regulation device, the control unit being configured to control the room-climate-regulation device.

Inventive concept 155. The apparatus according to inventive concept 153, wherein the common area is a common sleeping area, the control unit being configured, in response to analyzing the sensor signal, to determine which subjects of the plurality of subjects are present in the common sleeping area.

Inventive concept 156. The apparatus according to any one of inventive concepts 153-155,
 wherein the plurality of subjects consists of a first subject and a second subject,
 wherein the controllable mechanism has at least three settings that are distinct from one another, and
 wherein the control unit is configured to:
  in response to determining that the first subject, but not the second subject, is present in the common area, set the controllable mechanism to a first of the settings by communicating the control signal to the controllable mechanism,
  in response to determining that the second subject, but not the first subject, is present in the common area, set the controllable mechanism to a second of the settings by communicating the control signal to the controllable mechanism, and in response to determining that the first and second subjects are present in the common area, set the controllable mechanism to a third of the settings by communicating the control signal to the controllable mechanism.

Inventive concept 157. The apparatus according to inventive concept 156, wherein the third of the settings is an intermediate setting between the first and second settings, the control unit being configured to set the controllable mechanism to the intermediate setting in response to determining that the first and second subjects are present in the common area.

Inventive concept 158. The apparatus according to inventive concept 156, wherein the control unit is further configured to establish the first of the distinct settings, the second of the distinct settings, and the third of the distinct settings, in response to analyzing the sensor signal.

Inventive concept 159. Apparatus for monitoring a subject, the apparatus comprising:
  a sensor, configured to monitor the subject during a sleeping session of the subject, and to generate a sensor signal in response to the monitoring; and
  a control unit, configured to:
    analyze the sensor signal,
    in response to analyzing the sensor signal, identify an end of a chronologically-first sleep cycle of the subject during the sleeping session,
    in response to analyzing the sensor signal, identify an aspect of the sensor signal exhibited following the end of the chronologically-first sleep cycle,
    identify a physiological condition of the subject (i) in response to the aspect of the sensor signal that is exhibited following the end of the chronologically-first sleep cycle, and (ii) substantially not in response to any aspect of the sensor signal that is exhibited before the end of the chronologically-first sleep cycle, and
    generate an output indicative of the physiological condition.

Inventive concept 160. The apparatus according to inventive concept 159, wherein the control unit is configured to:
  in response to analyzing the sensor signal, identify an end of a chronologically-second sleep cycle of the subject during the sleeping session,
  in response to analyzing the sensor signal, identify an aspect of the sensor signal exhibited following the end of the chronologically-second sleep cycle, and
  identify the physiological condition of the subject (i) in response to the aspect of the sensor signal that is exhibited following the end of the chronologically-second sleep cycle, and (ii) substantially not in response to any aspect of the sensor signal that is exhibited before the end of the chronologically-second sleep cycle.

Techniques described herein may be practiced in combination with techniques described in one or more of the following patents and patent applications, which are incorporated herein by reference. In some applications, techniques and apparatus described in one or more of the following applications are combined with techniques and apparatus described herein:

U.S. patent application Ser. No. 11/048,100, filed Jan. 31, 2005, which issued as U.S. Pat. No. 7,077,810;

U.S. patent application Ser. No. 11/197,786, filed Aug. 3, 2005, which issued as U.S. Pat. No. 7,314,451;

U.S. patent application Ser. No. 11/446,281, filed Jun. 2, 2006, which issued as U.S. Pat. No. 8,376,954;

U.S. patent application Ser. No. 11/552,872, filed Oct. 25, 2006, now abandoned, which published as US 2007/0118054;

U.S. patent application Ser. No. 11/755,066, filed May 30, 2007, now abandoned, which published as US 2008/0114260;

U.S. patent application Ser. No. 11/782,750, filed Jul. 25, 2007, which issued as U.S. Pat. No. 8,403,865;

U.S. patent application Ser. No. 12/113,680, filed May 1, 2008, now abandoned, which published as US 2008/0275349;

U.S. patent application Ser. No. 12/842,634, filed Jul. 23, 2010, which issued as U.S. Pat. No. 8,517,953;

U.S. patent application Ser. No. 12/938,421, filed Nov. 3, 2010, which issued as U.S. Pat. No. 8,585,607;

U.S. patent application Ser. No. 12/991,749, filed Nov. 9, 2010, which issued as U.S. Pat. No. 8,821,418;

U.S. patent application Ser. No. 13/107,772, filed May 13, 2011, which issued as U.S. Pat. No. 8,491,492;

U.S. patent application Ser. No. 13/305,618, filed Nov. 28, 2011, now abandoned, which published as US 2012/0132211;

U.S. patent application Ser. No. 13/389,200, filed Jun. 13, 2012, now abandoned, which published as US 2012/0253142;

U.S. patent application Ser. No. 13/750,957, filed Jan. 25, 2013, which issued as U.S. Pat. No. 8,603,010;

U.S. patent application Ser. No. 13/750,962, filed Jan. 25, 2013, which issued as U.S. Pat. No. 8,679,034;

U.S. patent application Ser. No. 13/863,293, filed Mar. 15, 2013, now abandoned, which published as US 2013/0245502;

U.S. patent application Ser. No. 13/906,325, filed May 30, 2013, which issued as U.S. Pat. No. 8,882,684;

U.S. patent application Ser. No. 13/921,915, filed Jun. 19, 2013, which issued as U.S. Pat. No. 8,679,030;

U.S. patent application Ser. No. 14/019,371, filed Sep. 5, 2013, which issued as U.S. Pat. No. 9,883,809;

U.S. patent application Ser. No. 14/020,574, filed Sep. 6, 2013, which issued as U.S. Pat. No. 8,731,646;

U.S. patent application Ser. No. 14/054,280, filed Oct. 15, 2013, which issued as U.S. Pat. No. 8,734,360;

U.S. patent application Ser. No. 14/150,115, filed Jan. 8, 2014, which issued as U.S. Pat. No. 8,840,564;

U.S. patent application Ser. No. 14/231,855, filed Apr. 1, 2014, which issued as U.S. Pat. No. 8,992,434;

U.S. patent application Ser. No. 14/454,300, filed Aug. 7, 2014, which issued as U.S. Pat. No. 8,942,779;

U.S. patent application Ser. No. 14/458,399, filed Aug. 13, 2014, which issued as U.S. Pat. No. 8,998,830;

U.S. patent application Ser. No. 14/474,357, filed Sep. 2, 2014, which published as US 2014/0371635;

U.S. patent application Ser. No. 14/557,654, filed Dec. 2, 2014, issued as U.S. Pat. No. 9,026,199;

U.S. patent application Ser. No. 14/631,978, filed Feb. 26, 2015, published as US 2015/0164438;

U.S. patent application Ser. No. 14/624,904, filed Feb. 18, 2015, which issued as U.S. Pat. No. 9,131,902;

U.S. patent application Ser. No. 14/663,835, filed Mar. 20, 2015, which issued as U.S. Pat. No. 9,131,891;

U.S. patent application Ser. No. 14/726,706, filed Jun. 1, 2015, which published as US 2016/0058428;

U.S. patent application Ser. No. 14/810,814, filed Jul. 28, 2015, which issued as U.S. Pat. No. 9,265,445;

U.S. Provisional Application 62/045,237, filed Sep. 3, 2014;

U.S. Provisional Application 62/057,250, filed Sep. 30, 2014;
U.S. Provisional Application 62/088,697, filed Dec. 8, 2014;
U.S. Provisional Application 62/102,031, filed Jan. 11, 2015;
U.S. Provisional Application 62/152,902, filed Apr. 26, 2015;
International Patent Application PCT/IL2005/000113, which published as WO 2005/074361;
International Patent Application PCT/IL2006/000727, which published as WO 2006/137067;
International Patent Application PCT/IB2006/002998, which published as WO 2007/052108;
International Patent Application PCT/IL2008/000601, which published as WO 2008/135985;
International Patent Application PCT/IL2009/000473, which published as WO 2009/138976;
International Patent Application PCT/IL2011/050045, which published as WO 2012/077113;
International Patent Application PCT/IL2013/050283, which published as WO 2013/150523; and
International Patent Application PCT/IL2014/050644, which published as WO 2015/008285.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. An apparatus for use with a plurality of patients requiring respective care-provision tasks, the apparatus comprising:
    a plurality of sleep sensors automatically monitoring a plurality of patients and generating a plurality of signals in response thereto, without contacting the respective patients;
    a plurality of location sensors identifying respective locations of a plurality of care-providers, and generating location-sensing signals in response thereto;
    a controllable mechanism adjustable to alter a patient's environment to improve the a sleep quality of at least one of the plurality of patients;
    a user interface, and
    a care-provision prioritization control unit receiving the signals from the plurality of sleep sensors, receiving location-sensing signals from the plurality of location sensors, and providing control signals to control the operation of the controllable mechanism, the care-provision prioritization control unit analyzing the signals from the sleep sensors to ascertain respective sleep stages of the patients, controlling the controllable mechanism to alter a patient's environment to improve the sleep quality for at least a first patient of the plurality of patients if the care-provision prioritization control unit determines that the sleep of the first patient of the plurality of patients is to be prioritized over sleep of a second patient of the plurality of patients, analyzing the location-sensing signals to determine a prioritization of at least one of the care-provision tasks of the first patient of the plurality of patients over at least one other of the care-provision tasks of the second patient of the plurality of patients based on the sleep stage of each of the respective patients and the respective locations of the plurality of care-providers, and generating an output to a care-giver indicating the prioritization of the care-provision tasks,
    wherein the output is communicated to the user interface.

2. The apparatus according to claim 1, wherein the plurality of sleep sensors comprises a plurality of motion sensors.

3. The apparatus according to claim 1, wherein:
    the plurality of sleep sensors are configured to monitor a respective heart rate of each of the patients and to generate a plurality of heart rate signals in response thereto, and
    the care-provision prioritization control unit ascertains the respective sleep stages of the patients by (i) analyzing the heart rate signals generated in response to the respective heart rate of each of the patients, and (ii) identifying the respective sleep stages of the patients in response to analyzing the heart rate signals.

4. The apparatus according to claim 1, wherein:
    the plurality of sleep sensors monitor a respective breathing rate of each of the patients and generate a plurality of breathing rate signals in response thereto, and the care-provision prioritization control unit ascertains the respective sleep stages of the patients by (i) analyzing the breathing rate signals generated in response to the respective breathing rate of each of the patients, and (ii) identifying the respective sleep stages of the patients in response to analyzing the breathing rate signals.

5. The apparatus according to claim 1, wherein:
    each of the respective sleep stages is selected from the group consisting of: a slow-wave sleep stage, a rapid-eye-movement sleep stage, a light sleep stage, and an awake sleep stage, and wherein the care-provision prioritization control unit is determines the prioritization by:
    assigning a first prioritization level to a sleep stage selected from the group consisting of: a slow-wave sleep stage, and a rapid-eye-movement sleep stage,
    assigning a second prioritization level to a sleep stage selected from the group consisting of: a light sleep stage, and an awake sleep stage, and
    determining the prioritization of the at least one of the care-provision tasks over the at least one other of the care-provision tasks comprises prioritizing (i) at least one of the care provision tasks required by a patient whose sleep stage prioritization level is the second prioritization level, over (ii) the at least one other of the care-provision tasks required by a patient whose sleep stage prioritization level is the first prioritization level.

6. The apparatus according to claim 1, wherein:
    each of the respective sleep stages is selected from the group consisting of: a slow-wave sleep stage, a rapid-eye-movement sleep stage, a light sleep stage, and an awake sleep stage, and wherein the care-provision prioritization control unit determines the prioritization by:
    assigning a first rank to a sleep stage selected from the group consisting of: a slow-wave sleep stage, and a rapid-eye-movement sleep stage,
    assigning a second rank, which is greater than the first rank, to a sleep stage that is not assigned the first rank and that is selected from the group consisting of: the slow-wave sleep stage, and the rapid-eye-movement sleep stage,
    assigning a third rank, which is greater than the second rank, to a light sleep stage,
    assigning a fourth rank, which is greater than the third rank, to an awake sleep stage, and determining the prioritization of the at least one of the care-provision tasks over the at least one other of the care-provision tasks comprises prioritizing (i) at least one of the care-provision tasks required by a patient whose sleep stage rank is higher than the sleep stage rank of a patient requiring the at last one other of the care-provision tasks, over (ii) the at least one other of the care-provision tasks.

7. The apparatus according to claim 1, wherein the care-provision prioritization control unit prioritizes (i) at least one of the care-provision tasks required by a patient who is sleeping more heavily than a patient requiring the at least one other of the care-provision tasks, over (ii) the at least one other of the care-provision tasks.

8. The apparatus according to claim 7, wherein:
the plurality of sleep sensors:
monitor respective time-sensitive factors for the patients derived from the signals, and
generate time-sensitive signals in response thereto; and
the care-provision prioritization control unit:
analyzes the time-sensitive signals, and
determines the prioritization further in response to analyzing the time-sensitive signals.

9. The apparatus according to claim 8, wherein the plurality of sleep sensors (i) monitor respective heartbeats of the patients, and (ii) generate respective heartbeat signals for the patients, and wherein the care-provision prioritization control unit (i) analyzes the respective heartbeat signals and (ii) determines the prioritization further in response to analyzing the respective heartbeat signals.

10. The apparatus according to claim 8, wherein the plurality of sleep sensors (i) monitor respective respiratory rates for the patients and (ii) generate respective respiratory signals for the patients, and wherein the care-provision prioritization control unit (i) analyzes the respective respiratory signals and (ii) determines the prioritization further in response to analyzing the respective respiratory signals.

11. The apparatus according to claim 1, wherein the care-provision prioritization control unit prioritizes (i) at least one of the care-provision tasks over (ii) at least one other of the care-provision tasks wherein the at least one of the care-provision tasks is required by a first patient and the at least one other of the care-provision tasks is required by a second patient, and wherein the first patient is located farther away from a care-provider than the second patient.

12. The apparatus according to claim 1, wherein the controllable mechanism comprises a snoring inhibition mechanism.

13. The apparatus according to claim 1, wherein the controllable mechanism comprises a vibrating mechanism.

14. The apparatus according to claim 1, wherein the controllable mechanism comprises an adjustable resting surface.

15. The apparatus according to claim 1, wherein the controllable mechanism comprises a sound-playing device.

16. The apparatus according to claim 1, wherein the controllable mechanism comprises a room-climate regulation device.

17. The apparatus according to claim 1, wherein the controllable mechanism comprises an illumination device.

18. The apparatus according to claim 1, wherein the controllable mechanism comprises an adjustable pillow.

19. The apparatus according to claim 9, wherein the controllable mechanism comprises an adjustable resting surface.

20. The apparatus according to claim 10, wherein the controllable mechanism comprises an adjustable resting surface.

* * * * *